US011112232B2

(12) United States Patent
Tearney et al.

(10) Patent No.: US 11,112,232 B2
(45) Date of Patent: *Sep. 7, 2021

(54) APPARATUS AND METHODS FOR MIRROR TUNNEL IMAGING DEVICE AND FOR PROVIDING PSEUDOBESSEL BEAMS IN A MINIATURIZED OPTICAL SYSTEM FOR IMAGING

(71) Applicant: The General Hospital Corporation, Boston, MA (US)

(72) Inventors: Guillermo J. Tearney, Cambridge, MA (US); Biwei Yin, Arlington, MA (US); Kengyeh K. Chu, Cary, NC (US); Barry Vuong, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 8 days.

This patent is subject to a terminal disclaimer.

(21) Appl. No.: 16/796,103

(22) Filed: Feb. 20, 2020

(65) Prior Publication Data

US 2020/0217642 A1 Jul. 9, 2020

Related U.S. Application Data

(63) Continuation of application No. 15/760,910, filed as application No. PCT/US2016/052137 on Sep. 16, 2016, now Pat. No. 10,584,954.

(Continued)

(51) Int. Cl.
*G01B 9/02* (2006.01)
*G02B 6/26* (2006.01)
*A61B 5/00* (2006.01)

(52) U.S. Cl.
CPC ........ *G01B 9/02035* (2013.01); *A61B 5/0066* (2013.01); *A61B 5/0084* (2013.01);
(Continued)

(58) Field of Classification Search
CPC ............... G02B 6/262; G01B 9/02038; G01B 9/02091; G01B 9/02035; A61B 5/0066; A61B 5/0084
See application file for complete search history.

(56) References Cited

U.S. PATENT DOCUMENTS

| 3,721,965 A | 3/1973 | Morgan-Voyce |
| 5,484,994 A | 1/1996 | Roustaei |

(Continued)

FOREIGN PATENT DOCUMENTS

| WO | 2005047813 A1 | 5/2005 |
| WO | 2013109883 A1 | 7/2013 |
| WO | 2013177154 A1 | 11/2013 |

OTHER PUBLICATIONS

International Search Report and Written Opinion for international application PCT/US2016/052137 dated Jan. 9, 2017, 9 pages.

*Primary Examiner* — Seung C Sohn
(74) *Attorney, Agent, or Firm* — Quarles & Brady LLP

(57) ABSTRACT

Exemplary apparatus and method are provided for illuminating a sample. With such exemplary apparatus and/or method, it is possible to, using at least one source arrangement, provide at least one first electro-magnetic radiation. Using an optical system of an optics arrangement, it is possible to receive the first electro-magnetic radiation(s), and modifying the at least one first electro-magnetic radiation to be at least one second electro-magnetic radiation so as to be forwarded to the sample. Further, with the optical system, it is possible to extend the at least one second electro-magnetic radiation into or across the sample for a distance of at least 2 times the Raleigh range of a Gaussian beam when the optics arrangement and the sample are stationary with respect to one another. Additionally, using the optical system, it is possible to control a placement of a focus of the at least one second electro-magnetic radiation on or in the sample.

24 Claims, 48 Drawing Sheets

Related U.S. Application Data

(60) Provisional application No. 62/332,240, filed on May 5, 2016, provisional application No. 62/219,228, filed on Sep. 16, 2015.

(52) U.S. Cl.
CPC ..... *G01B 9/02038* (2013.01); *G01B 9/02091* (2013.01); *G02B 6/262* (2013.01)

(56) References Cited

U.S. PATENT DOCUMENTS

| | | | |
|---|---|---|---|
| 8,558,998 B2 | 10/2013 | Feldkhun et al. | |
| 8,848,200 B2 * | 9/2014 | Feldkhun | G01B 9/02041 356/521 |
| 9,058,652 B2 * | 6/2015 | Hanebuchi | G01B 9/02004 |
| 10,584,954 B2 * | 3/2020 | Tearney | G01B 9/02038 |
| 2002/0122246 A1 | 9/2002 | Tearney | |
| 2005/0018201 A1 | 1/2005 | De Boer | |
| 2006/0093276 A1 | 5/2006 | Bouma | |
| 2007/0171430 A1 | 7/2007 | Tearney et al. | |
| 2008/0021275 A1 | 1/2008 | Tearney | |
| 2011/0176142 A1 | 7/2011 | Hacker et al. | |
| 2011/0202044 A1 | 8/2011 | Goldshleger et al. | |
| 2013/0190565 A1 | 7/2013 | Gora | |
| 2013/0310643 A1 | 11/2013 | Gora | |
| 2014/0153864 A1 * | 6/2014 | Sinclair | G02B 23/26 385/12 |
| 2014/0218744 A1 | 8/2014 | De Boer et al. | |
| 2016/0265899 A1 | 9/2016 | Minemura et al. | |
| 2019/0261840 A1 | 8/2019 | Gora | |

\* cited by examiner

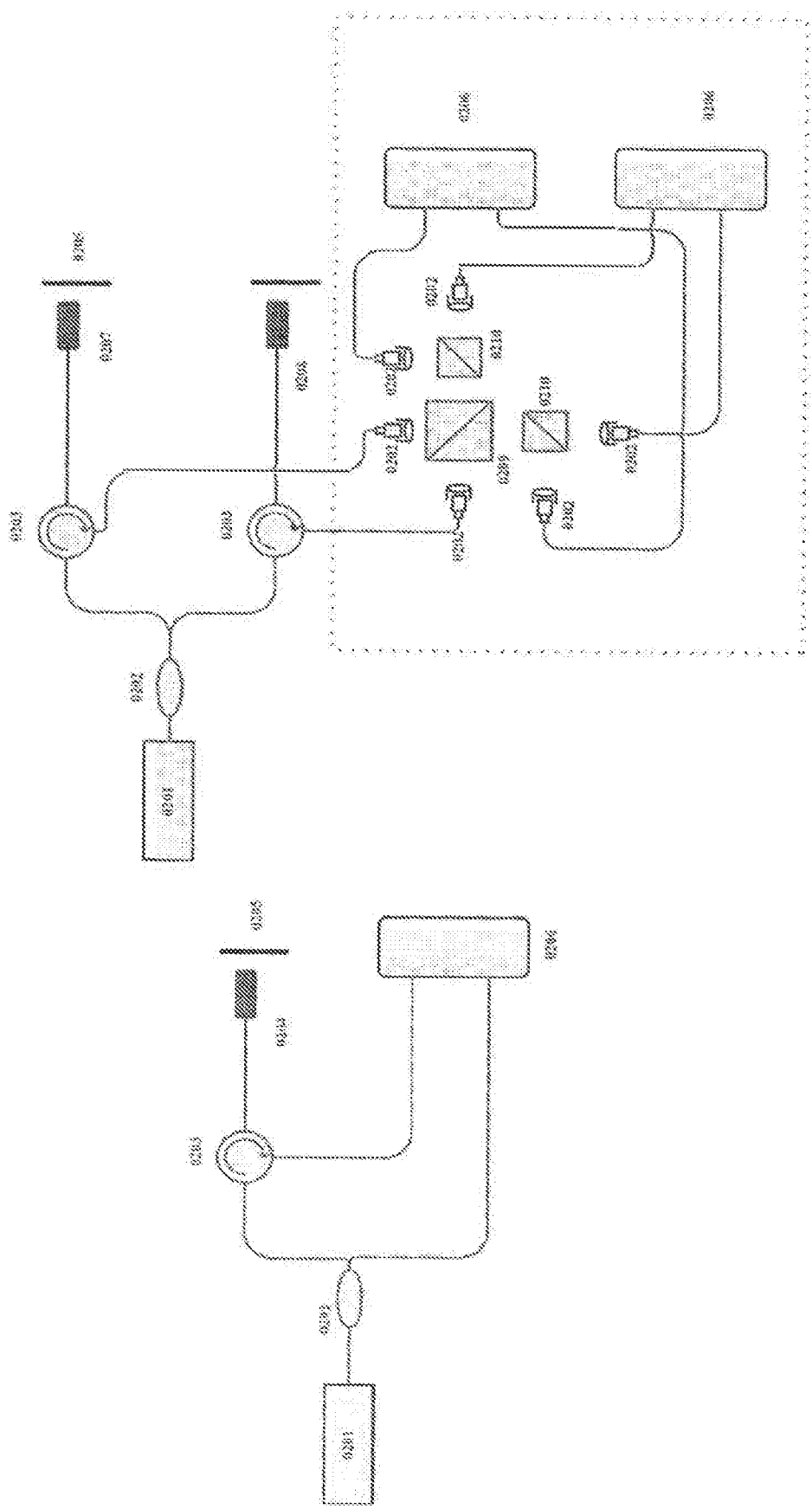

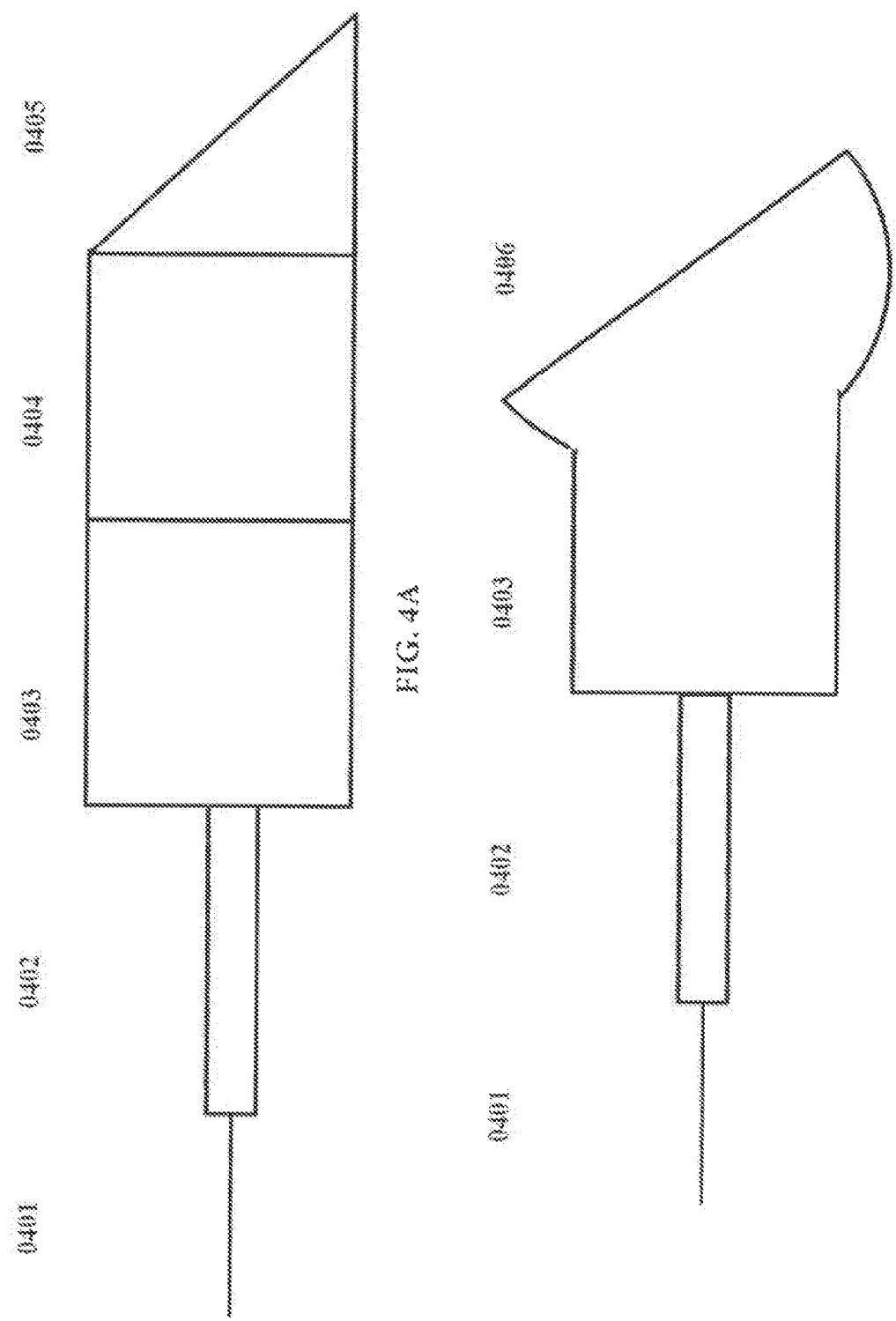

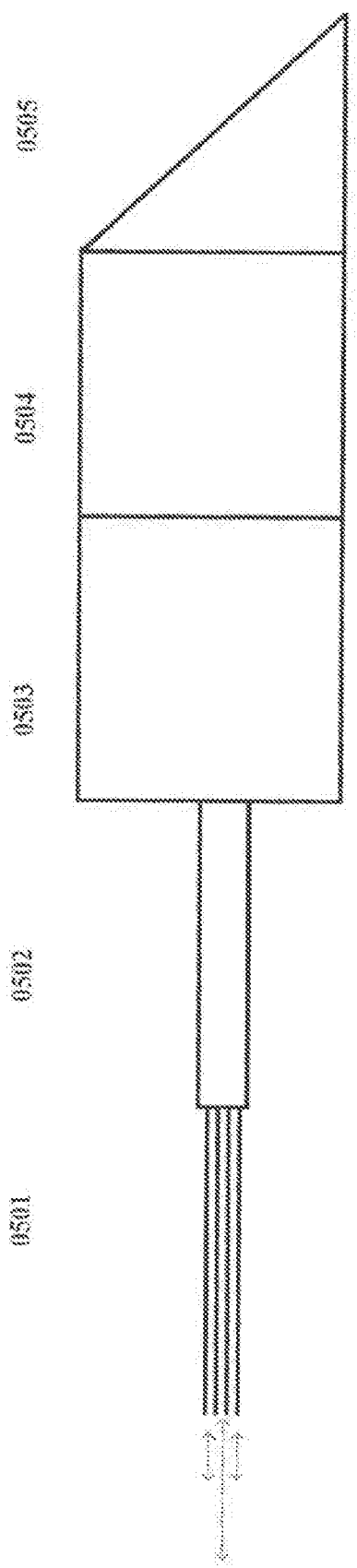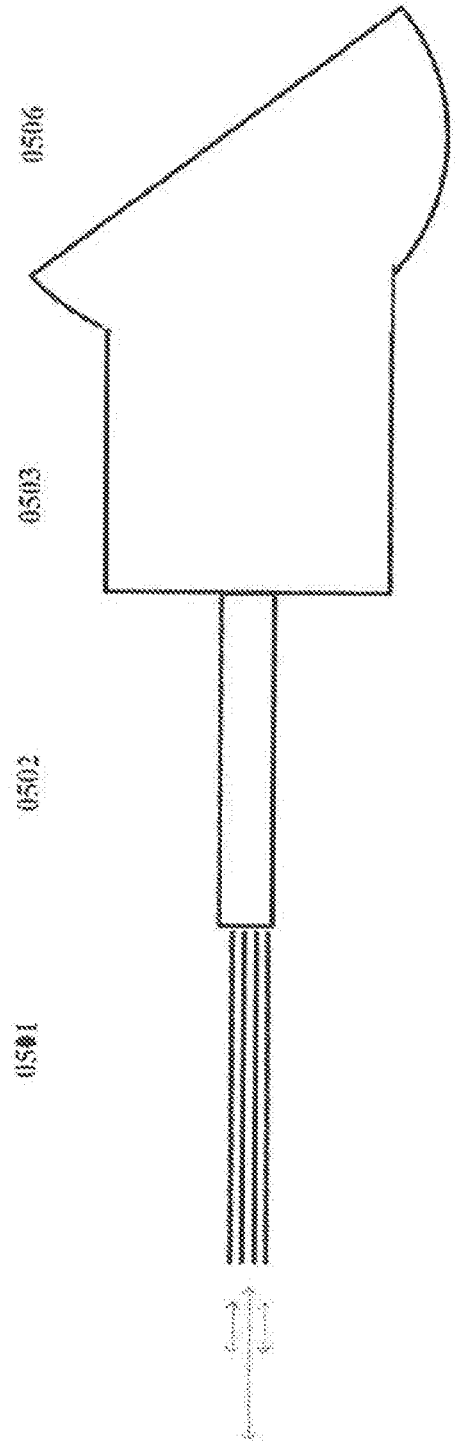
FIG. 5A
FIG. 5B

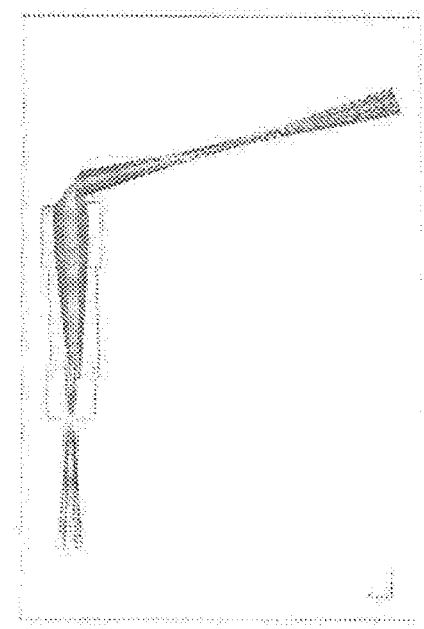
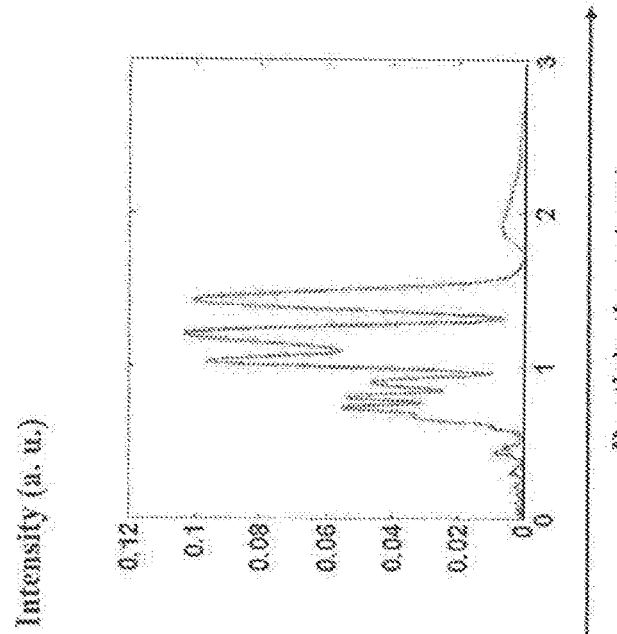
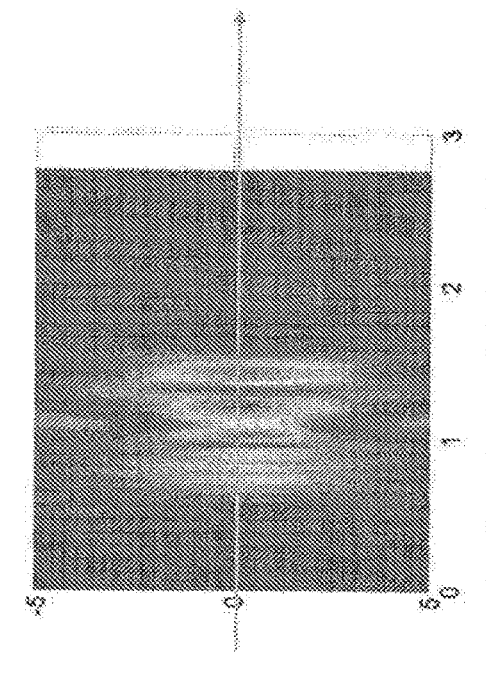
FIG. 8A
FIG. 8B
FIG. 8C

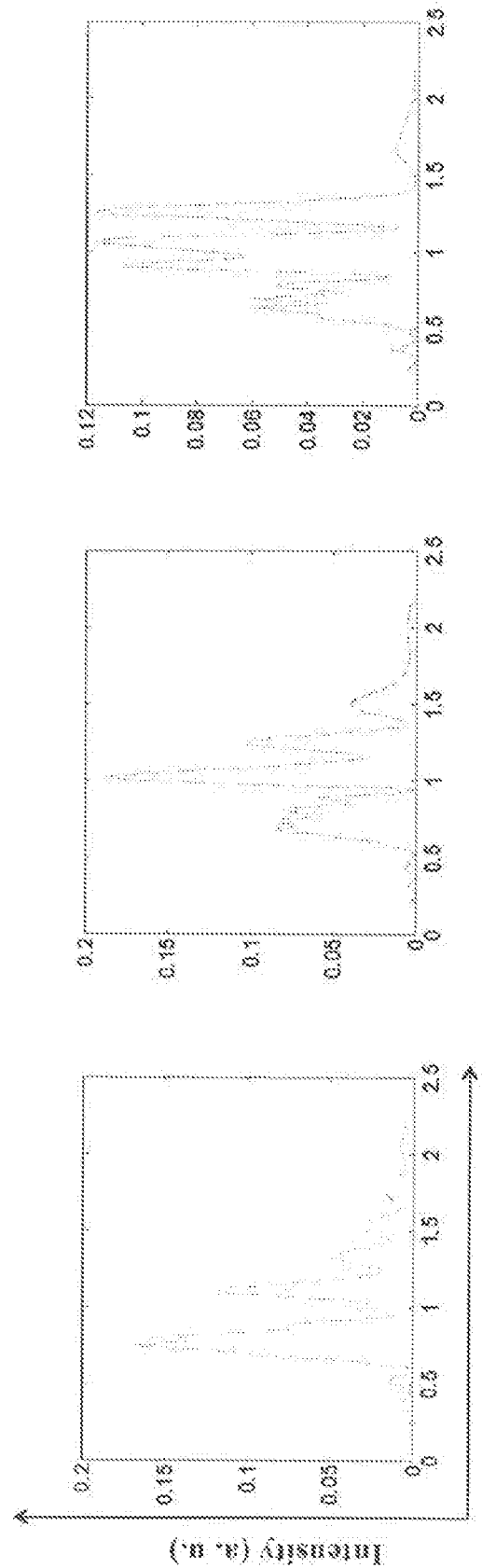

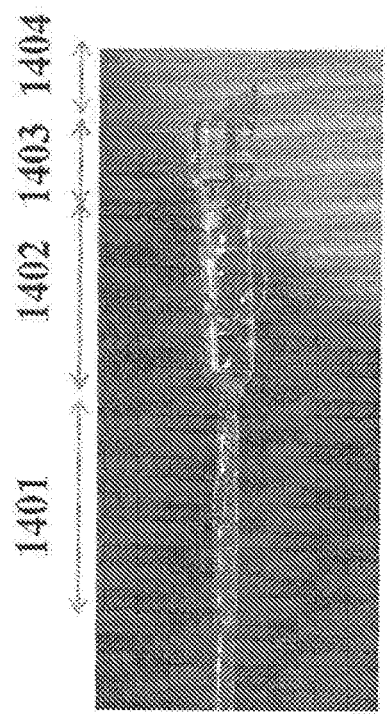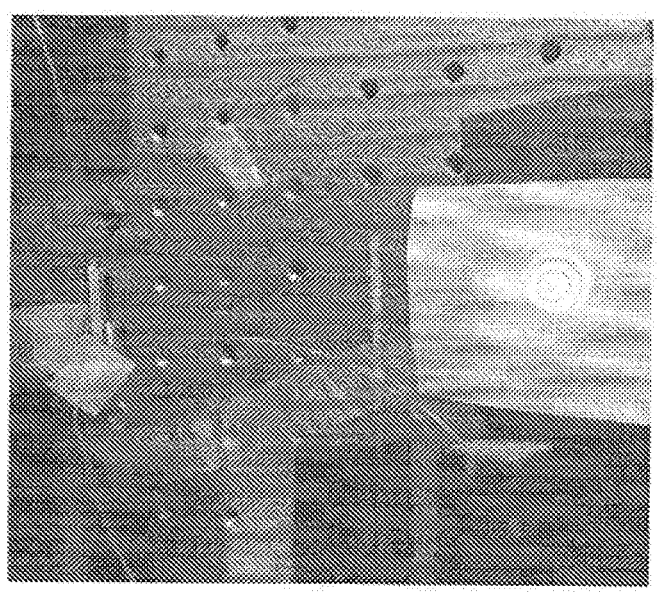
Fig. 14

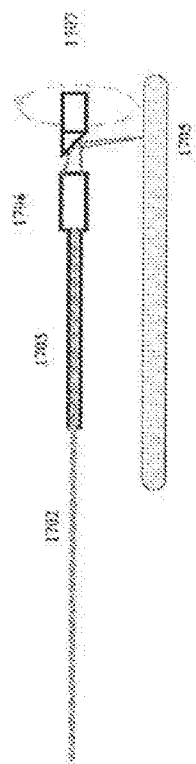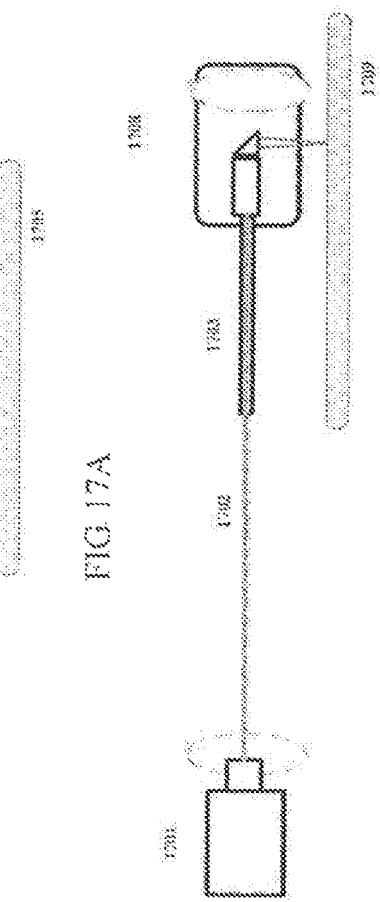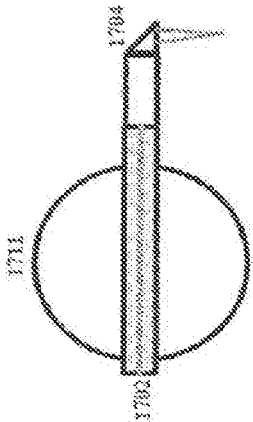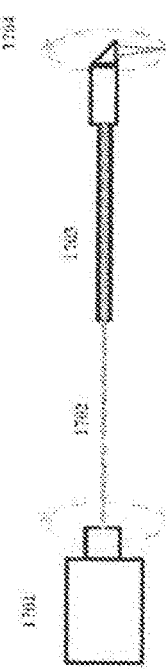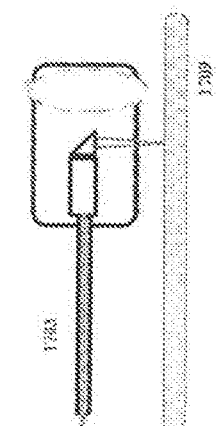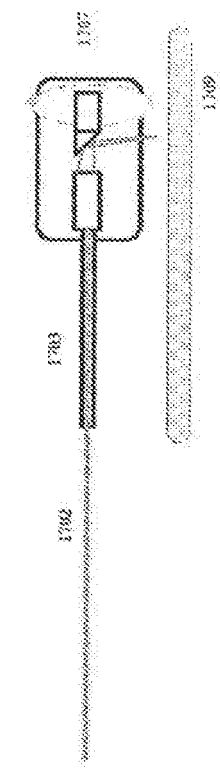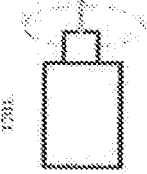
FIG. 17A  FIG. 17B  FIG. 17C  FIG. 17D  FIG. 17E  FIG. 17F

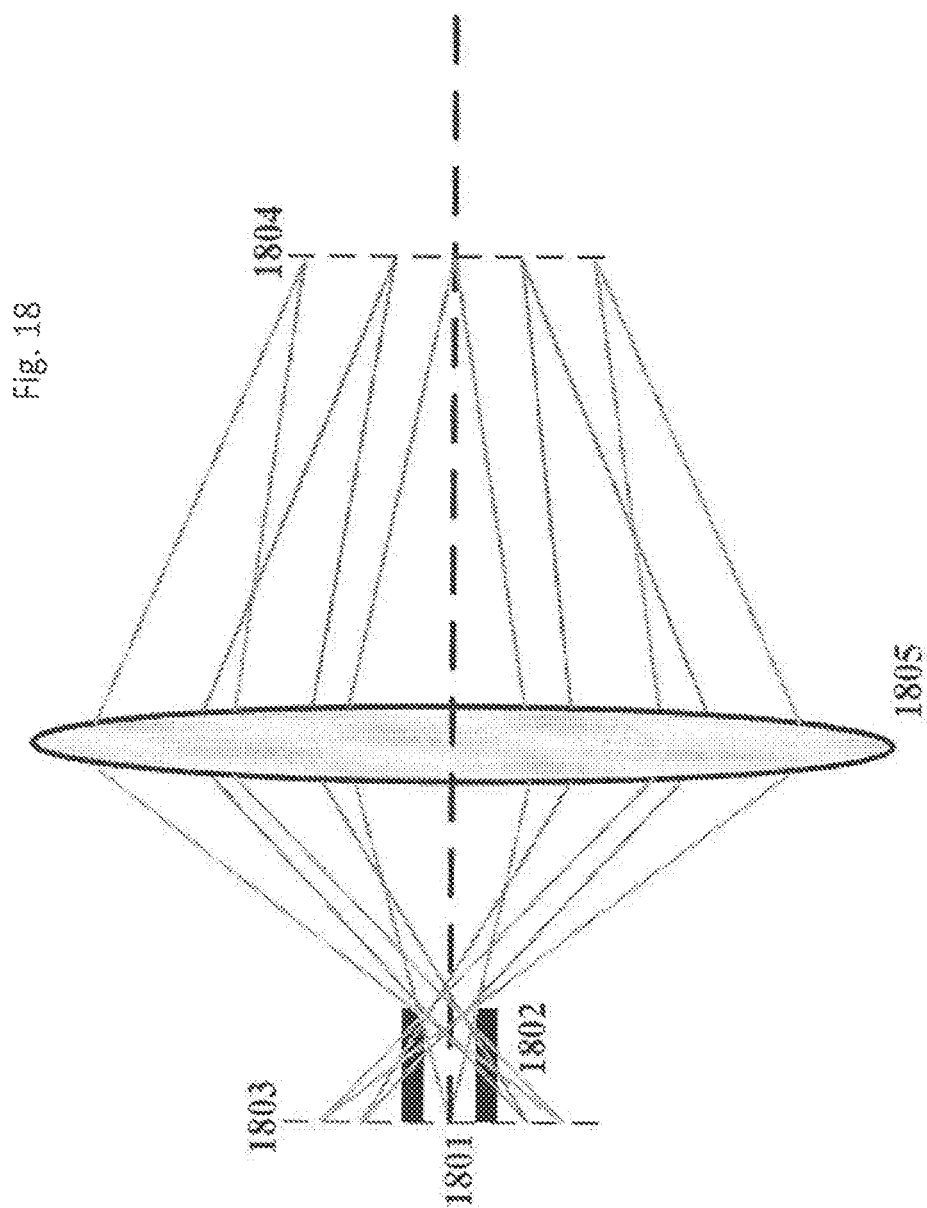

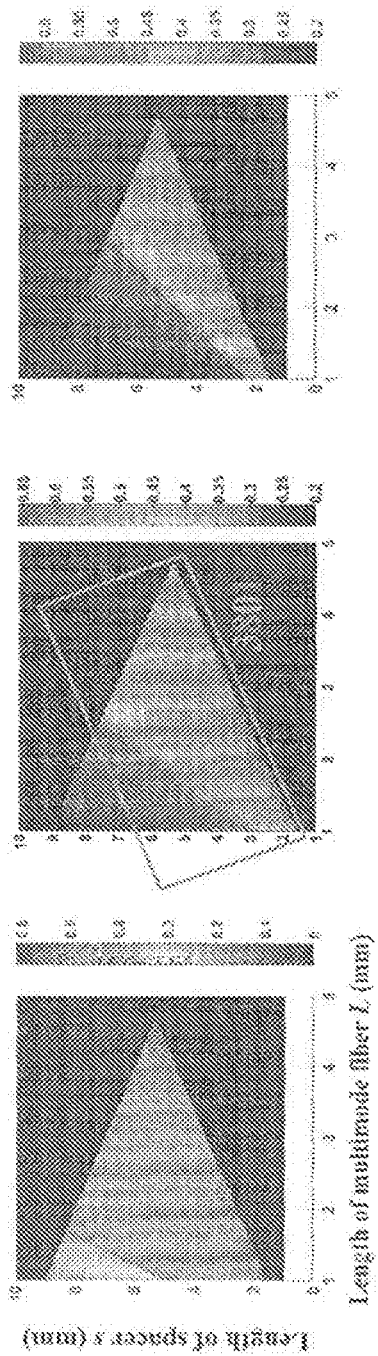
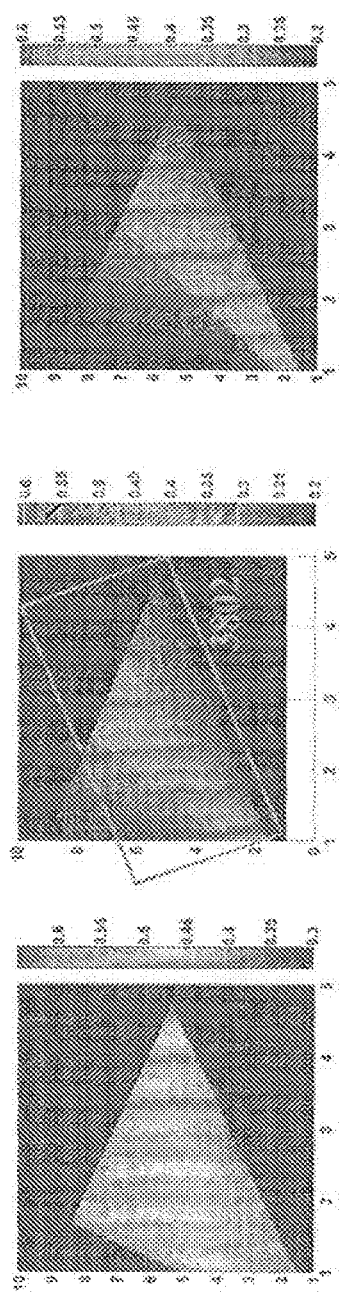
FIG. 38(a) FIG. 38(b) FIG. 38(c) FIG. 38(d) FIG. 38(e) FIG. 38(f)

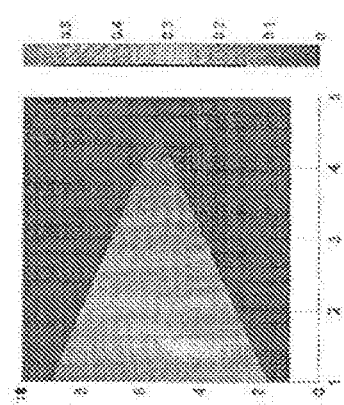
FIG. 39(c)
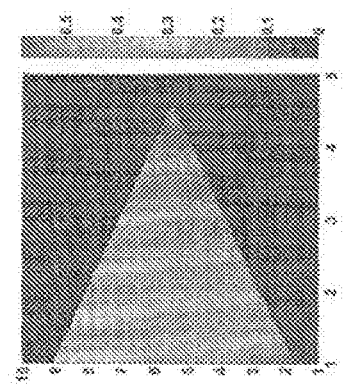
FIG. 39(b)
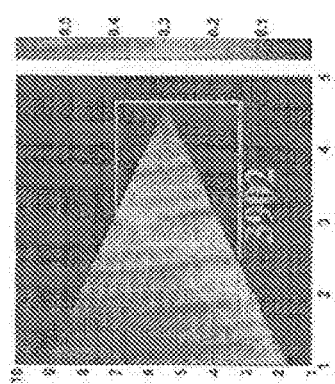
FIG. 39(e)
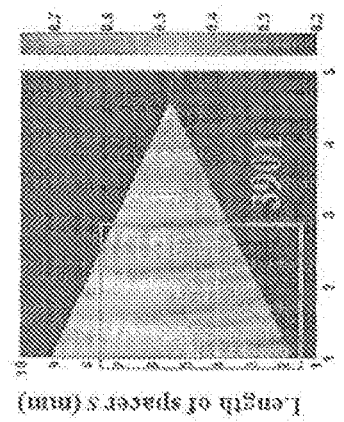
FIG. 39(a)
FIG. 39(d)

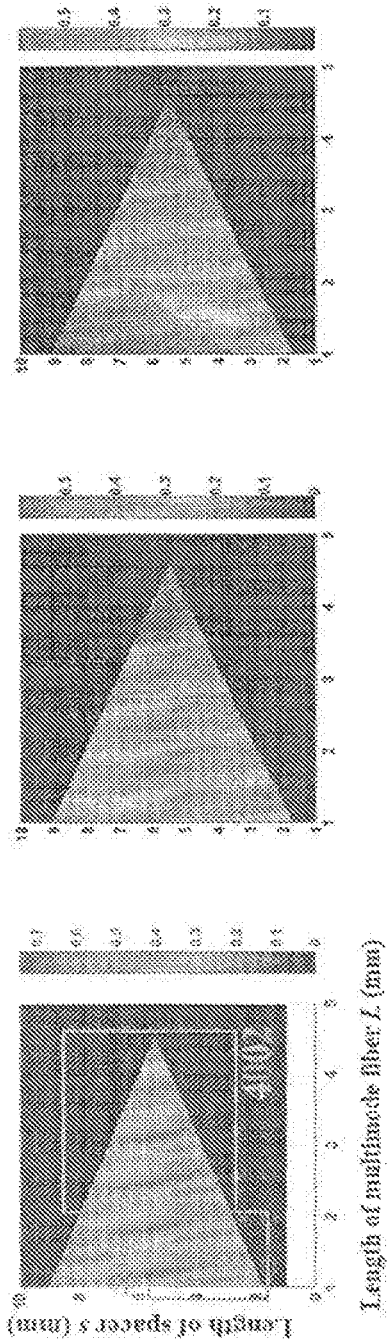
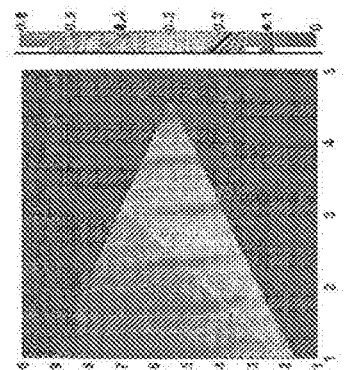
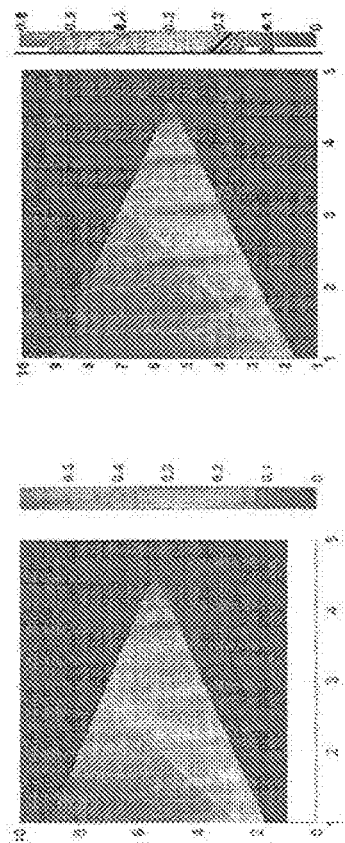
FIG. 40(a) FIG. 40(b) FIG. 40(c)
FIG. 40(d) FIG. 40(e)

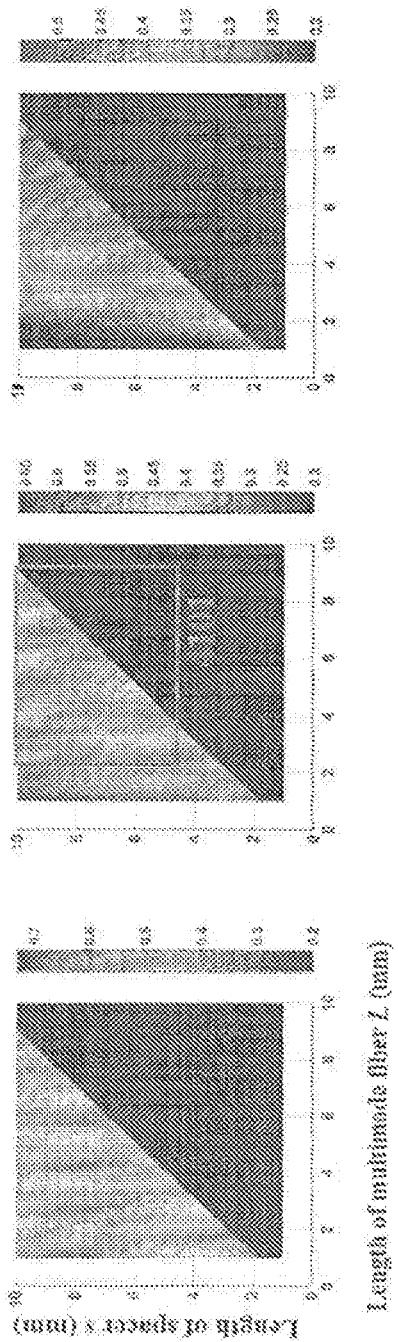
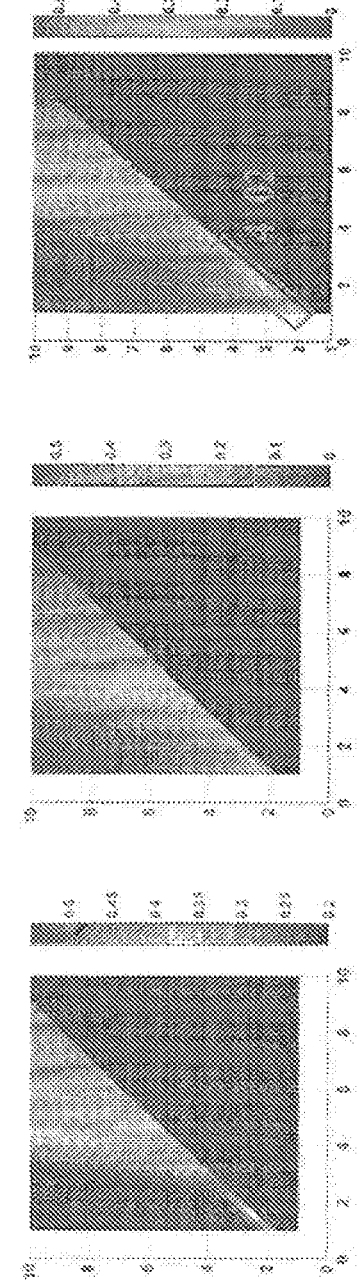
FIG. 41(a)  FIG. 41(b)  FIG. 41(c)
FIG. 41(d)  FIG. 41(e)  FIG. 41(f)

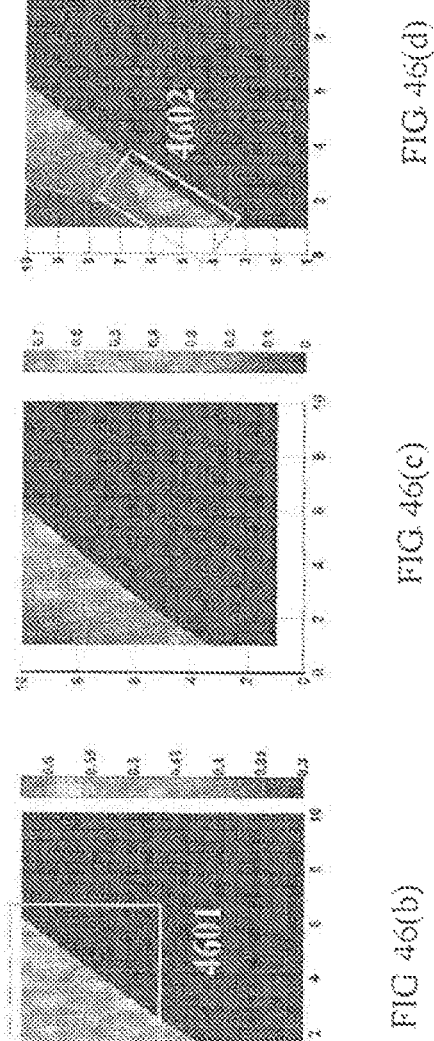
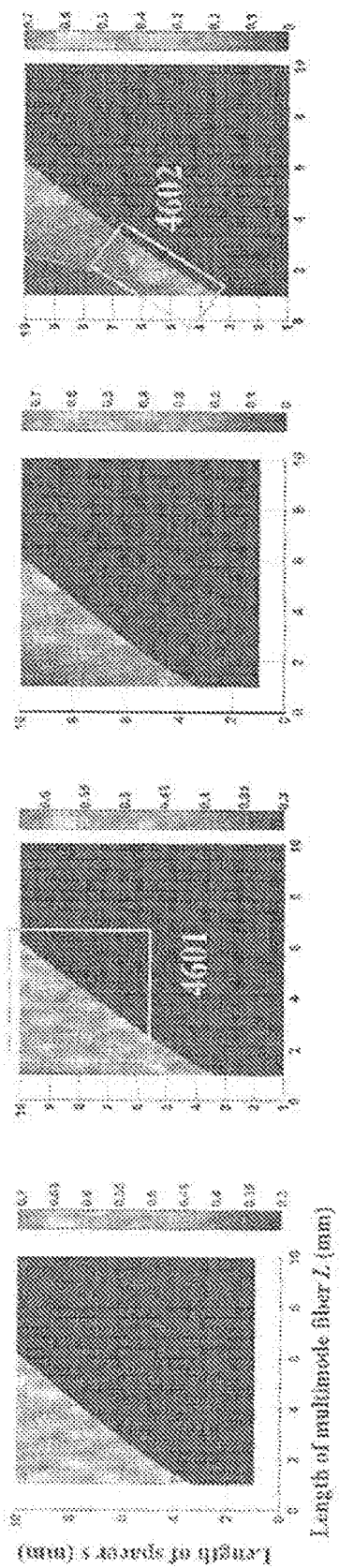
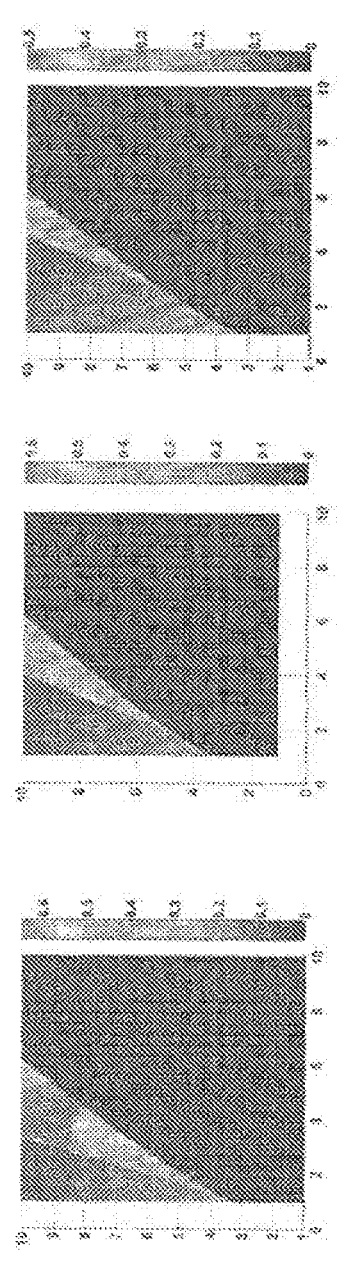
FIG. 46(a) FIG. 46(b) FIG. 46(c) FIG. 46(d)
FIG. 46(e) FIG. 46(f) FIG. 46(g)

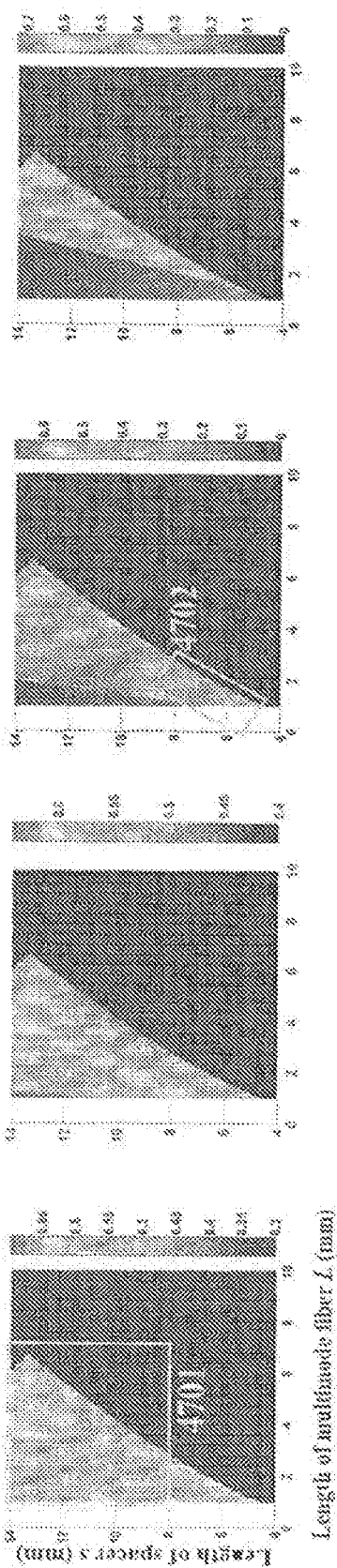
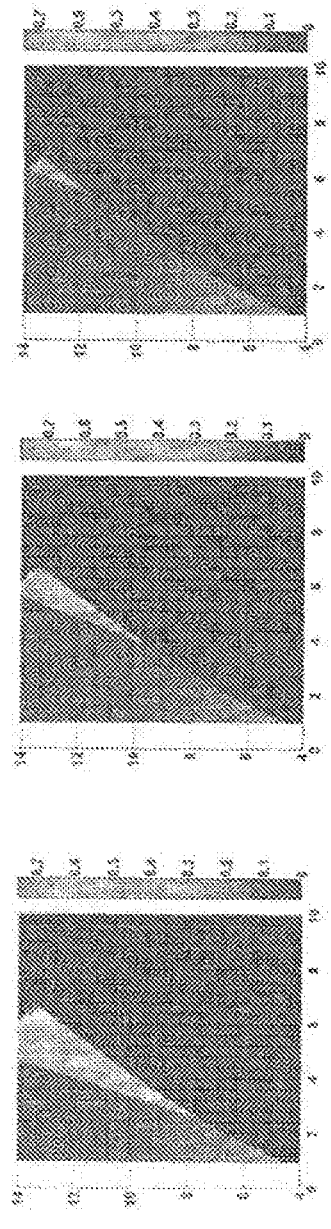
FIG. 47(a) FIG. 47(b) FIG. 47(c) FIG. 47(d)
FIG. 47(e) FIG. 47(f) FIG. 47(g)

APPARATUS AND METHODS FOR MIRROR TUNNEL IMAGING DEVICE AND FOR PROVIDING PSEUDOBESSEL BEAMS IN A MINIATURIZED OPTICAL SYSTEM FOR IMAGING

CROSS REFERENCE TO RELATED APPLICATIONS

The present application is a continuation of U.S. patent application Ser. No. 15/760,910 filed on Mar. 16, 2018 which is a U.S. National Stage of PCT Application No. PCT/US2016/052137 filed on Sep. 16, 2016 which relates to and claims priority from U.S. Patent Application Ser. No. 62/219,228 filed Sep. 16, 2015 and U.S. Patent Application Ser. No. 62/332,240 filed May 5, 2016, the entire disclosures of which are incorporated herein by reference.

FIELD OF THE DISCLOSURE

The present disclosure relates to imaging apparatus and device, and more particularly to exemplary embodiments of an intravascular optical coherence tomography (IV-OCT) imaging system, as well as to generating multiple pseudo-Bessel beams with coaxial foci for image depth of focus extension in a compact fiber probing optical system.

BACKGROUND INFORMATION

Optical Coherence Tomography (OCT) is a depth-resolved high-resolution imaging technique. For a typical OCT system, a low-coherence light is illuminated on the sample, the backscattered light from sample is interfered with a reference light, depth-resolved image can be reconstructed based on the interference fringe signal. So far, OCT has been applied mostly for ophthalmology, cardiology, and gastrointestinal (GI) tract imaging. It was first introduced as a time-domain system, which has a mechanically scanning reference mirror to acquire depth reflectivity information of sample, later spectrometer based spectral-domain OCT was invented, fringe signal is acquired from line-scan camera after grating spreads the spectrum, and more recently, swept-source laser based OCT has been developed, spectrum signal is encoded in time series, which substantially increases the acquisition speed.

The OCT systems and methods provide a high-resolution real-time imaging technique: the axial resolution can be around 10 µm or 1 µm in tissue depending on the bandwidth of light source. By applying a 2-dimensional (2D) galvanometer scanning system or rotation-pullback scheme, 3D image can be constructed. Lateral resolution of the image depends on objective optics. The resolution and depth of focus of a conventional objective obeys Rayleigh criteria, for example, using an objective with 0.02 numerical aperture (NA) imaging at 1.3 µm center wavelength, its lateral resolution is approximately 40 µm, and depth of focus 2.0 mm; increasing objective NA leads to higher resolution, but reduces the depth of focus (depth of focus is proportional to the square of the resolution). Therefore, there is always a trade-off between lateral resolution and depth-of-focus.

For cellular or sub-cellular level imaging, the resolution of imaging system requires to be better than 5 µm, less than 2 µm or even less than 1 µm in tissue. By applying an ultra-broad band light source (300 nm spectrum bandwidth), the axial resolution of OCT system can be less than 2 µm in tissue; combined with a 0.1 NA objective imaging at 800 nm wavelength region, the lateral resolution can achieve 5 µm, but with depth-of-focus only 50 µm. So limitation on depth-of-focus prevents the application of high-resolution OCT when long ranging depth or imaging depth is required such as in-vivo cardiology imaging, which requires ranging depths longer than 500 µm, and preferably longer than 1.0 mm, and in best cases, longer than 1.5 mm. In addition, for many arterial applications, it cannot be assured that the catheter is in the center of the vessel, which places the desired specifications to be at least greater than 2.0 mm and preferably greater than 3.0 mm and in the best case, greater than 5.0 mm. Previously, techniques such as aperture apodization and synthesized aperture have been developed to increase the depth of focus, but application of these techniques for in-vivo imaging still presents difficulty due to limited performance and implementation complexity.

In a depth-resolved imaging system (such as optical coherence tomography (OCT)), trade-off usually exists between lateral resolution and depth of focus (DOF). For instance, the DOF of a Gaussian beam is proportional to the square of the size of the focal spot, therefore using a Gaussian beam to acquire images that can maintain a high lateral resolution over a long axial field of view is challenging. To overcome this obstacle, various techniques have been proposed, and can be divided into four categories: 1. numerical refocusing-a method that digitally compensates the defocus aberration of the beam according to beam diffraction and sample scattering, which presents difficulty in real-time imaging due to computational intensive processing and phase-stable acquisition; 2. multi-beam acquisition scheme-a technique that applies multiple beams to acquire in-focus images from different depth regions of the sample, which substantially increases the complexity of the imaging system; 3. pupil apodization and phase mask-methods that modify the optical system pupil to extend the DOF of a standard beam, which provides limited improvement while the signal loss is critical; 4. application of a Bessel beam-one type of the beam that has depth-invariant Bessel profile on the transverse plane able to provide an extremely long DOF.

In a coherent light based optical system, the most common form of beam is a Gaussian beam as it is the output of a single-mode fiber, and after transmitted by the standard optical components such as spherical lenses, reflective mirrors, and spacers, it remains as a Gaussian beam, so we define this type of optical system as a Gaussian beam optical system. A Bessel beam can be generated in a Gaussian beam optical system by using an axicon lens. If a Gaussian beam is focused by an axicon lens, the energy of the focused field is concentrated at the tip of the axicon lens, and falls off quickly in the axial direction in response to transverse Gaussian intensity distribution of the input beam. Extension of the working distance requires more complicated optical setup such as introducing a hollow beam that has a lower intensity distribution in the center of the beam, which unavoidably leads to increased system complexity and makes the design not suitable for implementation in a compact imaging device such as a catheter or an endoscope, of which working distance is an important parameter that needs to meet specific application specification, such as 300-500 µm for human coronary artery catheter and 6-7 mm for human gastrointestinal (GI) tract capsule. Thus, the application of a Bessel beam for DOF extension in a catheter or endoscope optical system is greatly limited.

Accordingly, there is a need to address and/or overcome at least some of the deficiencies described herein above.

SUMMARY OF EXEMPLARY EMBODIMENTS

To that end, to solve the problem of limited depth of focus of high-resolution objective optics in OCT imaging, according to an exemplary embodiment of the present disclosure, it is possible to provide a mirror tunnel based focusing optical system that can significantly increase focusing range. According to certain exemplary embodiment of the present disclosure, term mirror tunnel can be referred to as, e.g., a cylindrical waveguide that transmits light of different propagation modes; after focusing, multiple on-axis foci are introduced to extend the depth of focus. The self-imaging effect of cylindrical waveguide can divide the wavefront into multiple annular zones, collinear beams are generated and focused onto different depth region in image space. Therefore, this can be referred to as, e.g., a self-imaging wavefront division technique. In other exemplary embodiments of the present disclosure, the exemplary mirror tunnel can have other geometries, such as an elliptical waveguide, and/or comprise at least one planar surface, a triangular (prism-shaped) waveguide, rectangular waveguide, square waveguide, hexagonal waveguide or the like.

In one exemplary embodiment of the present disclosure, the mirror tunnel configuration can provide more than one focused spot along the axis of the optical beam that impacts the sample. In so doing, e.g., the focal range can be extended. In yet another exemplary embodiment, the mirror tunnel configuration can provide more than one focused spot at least partially along the axis of the optical beam that impinges the sample.

One of the exemplary embodiments of the present disclosure can include a common-path mirror tunnel fiber probe for spectral-domain OCT system. It consists of a single mode fiber for system light transmission, a multimode fiber as the mirror tunnel, a spacer for beam propagation, a grin lens for beam focusing and a prism for side-view imaging. The designed common-path mirror tunnel fiber probe can provide a lateral resolution better than about 5 µm and depth of focus more than about 1.5 mm. To reduce the dispersion due to optical fiber pathlength mismatch between sample and reference arms and polarization mode dispersion due to uneven twisting and bending between two arms, one of the prism surface can provide a back-reflection, and may be used as the reference. For cellular or sub-cellular level tissue imaging, a spectral-domain OCT system using a broadband light source is designed and constructed to provide axial resolution higher than 2 µm in tissue.

Compared with conventional probing OCT system with 10-15 µm axial resolution, 30-40 µm lateral resolution, 2 mm depth of focus, the exemplary technique according to an exemplary embodiment of the present disclosure can provide a more than 10-fold improvement in resolution, while maintaining similar depth of focus as a conventional OCT system. In-vivo cardiology OCT imaging generally requires a ranging depth of at least 500 µm, prefers 1 mm, and even 1.5 mm when catheter is centered inside the vessel, to ensure a good sampling on the vessel wall, greater than 2 mm ranging depth is preferred, or even 3 mm, and greater than 5 mm for the best case; to achieve this, greater number of propagation modes need to be introduced by mirror tunnel.

In one exemplary embodiment, the mirror tunnel based focusing optical system can be designed and fabricated as a flexible fiber probe, which guarantees the feasibility for in-vivo imaging such as cardiology and GI tract imaging. For in-vivo imaging, mirror tunnel fiber probe is connected to OCT system through a single-mode single-channel rotary junction. A pullback stage together with the rotary junction provides circumferential scan for in-vivo cardiology and GI tract imaging. Micro-motor can also be used for circumferential scan. For ex-vivo imaging, fiber probe can be attached to a high-accuracy high-speed 2D translational stage, by synchronizing camera data acquisition and translational stage controller, 3D volume image can be acquired. This scanning setup provides field-aberration free images compared with galvanometer based 2D scanning system.

The exemplary mirror tunnel based focusing optical system can be used with, e.g., a spectral-domain OCT system with fiber probe as sample arm optics, as well as for imaging systems that use an extended depth-of-focus.

First, the exemplary mirror tunnel fiber probe does not have to be a common-path fiber probe. For example, a non-common-path OCT fiber probe can be used with a dispersion matched reference arm, numerical dispersion compensation algorithm can be applied to improve system axial resolution.

Secondly, mirror tunnel fiber probe can be combined with other imaging techniques for multi-modality imaging, such as fluorescence, autofluorescence, Raman, spectroscopy, and corresponding modification on the fiber would be performed. For example, replacing single mode fiber with a double-cladding fiber enables dual-modality imaging: the core transmits OCT light and the inner cladding is used for delivery and detection of the other imaging modes.

Thirdly, the exemplary mirror tunnel based focusing optical system can be a free space 2D scanning system, where two galvanometers can be used to steer the beam to scan across the sample. Other exemplary focusing optics can be used to replace graded-index lens (GRIN), such as, e.g., ball lens and/or achromatic lens.

Fourthly, an exemplary mirror tunnel fiber probe can be used for a swept-source based OCT or optical frequency domain imaging (OFDI) system. A spectral-domain system uses a low-coherence light source emitting a broad spectrum of light, acquires spectrum fringe signal by spreading spectrum in one dimension, then collects A-scan signal through a line-scan camera, and frame grabber digitizes the analog signal. The swept-source or OFDI system can deliver a series of narrow linewidth light onto reference and sample, receives time-encoded fringe signal through photodetectors, and then analog-digital-convertor (ADC) card can digitize the signal. Balance detection can be used to reduce common mode noise, and polarization-diversity detection can be used to reduce the effect of polarization mode dispersion (PMD). The exemplary mirror tunnel fiber probe can be adapted for both schemes, with the difference being in system configuration and data acquisition.

Fifthly, in general, the exemplary technique according to the exemplary embodiment of the present disclosure can be applied to overcome the depth of focus limitation presented in most of high-resolution imaging system, for example a high NA camera. Mirror tunnel focusing optical system can be applied to introduce multiple foci along the optical axis and extend the depth of focus. Original Gaussian beam can be divided into multiple annular zone corresponding to each propagation mode, after focusing, each mode covers a certain bandwidth of the entire spatial frequency band of original Gaussian beam. Therefore, modes higher than zero order are not Gaussian beam as they are not able to cover a complete spatial frequency band, nor Bessel beam as they cover a much broader bandwidth than Bessel beam which only has one spatial frequency component, and all modes together cover a similar bandwidth of original Gaussian Beam.

Sixthly, the exemplary mirror tunnel focusing optical system can transmit light consisting of multiple spatial frequency bands, therefore multiple spatial frequency bands of information can be delivered or acquired simultaneously through this compact design. Longer pathlength difference between spatial frequency bands can be realized by properly designing mirror tunnel's aspect ratio, which facilitates pathlength encoded multi-band spatial frequency imaging.

Seventhly, the exemplary mirror tunnel is not limited to a cylindrical waveguide, as it can also be implemented as a 2D rectangular waveguide or 1D planar waveguide. Mirror images of the source introduced by different dimension or geometric shape of the waveguide can behave as additional light sources to the optical system and introduce different propagation modes. For example, a 1D planar waveguide can introduce additional focal points on the image plane in one dimension, which enables multi-focus imaging in lateral dimension.

Eighthly, different propagation modes of light emitting from mirror tunnel can spatially interfere and generate interference pattern in lateral or axial dimension. In transverse plane, annular wavefront distribution is similar to the effect of an annular phase mask, applications of phase mask such as beam shaping can be realized by mirror tunnel in a similar way.

Ninthly, the exemplary mirror tunnel based focusing optics can be applied for any depth-resolved imaging technique that requires extended depth-of-focus.

According to yet another exemplary embodiment of the present disclosure, an imaging method and design configuration can be provided to generate and provide pseudo-Bessel beams in a Gaussian beam optical system without increasing system complexity. The exemplary optical configuration can include a single-mode fiber that emits a Gaussian beam, a multimode fiber that generates multiple propagation modes, a glass spacer or free space that propagates the beam, and/or a focusing lens. The pseudo-Bessel beam generated in this manner can have Bessel profile on transverse plane with a radius linearly proportional to the depth.

This exemplary linear expansion coefficient can be governed by the aspect ratio of the multimode fiber and the length of spacer. Therefore, with exemplary optics according to an exemplary embodiment of the present disclosure, the pseudo-Bessel beam can provide an extended DOF for imaging. Additionally, this exemplary optical configuration can provide multiple pseudo-Bessel beams to image at different coaxial depth regions that further extend the effective imaging range.

To that end, according to other exemplary embodiments of the present disclosure, which can be operable and/or interconnected with the exemplary embodiments described herein above, a self-imaging wavefront division fiber optic probe for capsule based human GI tract OCT imaging can be provided. Such exemplary fiber optic probe can include a single-mode fiber for system light transmission, a cylindrical waveguide for generation of multiple propagation modes, a spacer for beam expansion, and a GRIN lens for beam focusing. A Gaussian beam can be emitted from the core of the single-mode fiber distal end, and due to self-imaging of the multi-mode fiber, the beam emitted from the single-mode fiber distal end can include ring-shaped images on the transverse plane. Each ring can be the virtual source of the corresponding high order mode (order higher than $0^{th}$). After propagating in a spacer, each of the high order mode can be incident on the pupil with a tilted wavefront due to off-axis illumination, and the energy can be concentrated within an annular zone projected by the cylindrical waveguide aperture. The focused field of each high order mode can be a pseudo-Bessel beam and the coaxial foci of all modes significantly extend the effective imaging range.

According to another exemplary embodiment of the present disclosure, which can be operable and/or interconnected with the exemplary embodiments described herein above, an exemplary design process can be provided to generate multiple pseudo-Bessel beams with coaxial foci and the physical properties of the beams. For example, a number (e.g., three) basic variables should be determined for the exemplary design: the diameter and length of the waveguide, and the length of the spacer. The length of the waveguide and the length of the spacer can be used to determine the pseudo-Bessel beam quality relating to the diffraction property of the beam. The aspect ratio of waveguide can be used to determine the number of modes and consequently number of pseudo-Bessel beams relating to the effective imaging range. In such exemplary self-imaging wavefront division optical system, the imaging range may be related to DOF determine by beam diffraction, as well as to the intensity distribution. This is because the energy distribution of each pseudo-Bessel beam can be concentrated within a certain region that limits the effective imaging range. Therefore, additional modes are preferable for use.

For example, to design a self-imaging wavefront division optical system so as to achieve a high resolution and long DOF at a specific working distance generally utilizes an optimization of several parameters. Such exemplary parameters can be but not limited to, e.g., diameter and length of cylindrical waveguide, and the length of spacer according to the system single-mode fiber mode field diameter, wavelength, and/or refractive indices. The optimization merit function includes, e.g., four or more parameters: (a) percentage of the energy contained in high order modes; (b) the linear expansion coefficient of the pseudo-Bessel beams; (c) focal spot size; and (d) the intensity distribution uniformity in axial direction. Parameter (a) can be aimed for increasing the energy contained in pseudo-Bessel beams. Parameter (b) can be aimed for reducing the effect of diffraction of the beams. Parameter (c) can be aimed for improving the resolution. Parameter (d) can be aimed for mitigating the intensity gaps between modes. Different weight can be setup for these exemplary criteria for optimization towards the specific design requirement.

To that end, exemplary apparatus and method can be provided for illuminating a sample according to an exemplary embodiment of the present disclosure. With such exemplary apparatus and/or method, it is possible to, using at least one source arrangement, provide at least one first electro-magnetic radiation. Using an optical system of an optics arrangement, it is possible to receive the first electro-magnetic radiation(s), and modifying the at least one first electro-magnetic radiation to be at least one second electro-magnetic radiation so as to be forwarded to the sample. Further, with the optical system, it is possible to extend the second electro-magnetic radiation(s) into or across the sample for a distance of at least 2 times the Raleigh range of a Gaussian with equal spot size when the optics arrangement and the sample are stationary with respect to one another. Additionally, using the optical system, it is possible to control a placement of a focus of the second electro-magnetic radiation(s) on or in the sample. The distance can be provided from a surface of and through the sample, or across a surface of the sample. The control system can include a set of optical components in an optical path of the first electro-magnetic radiation(s).

According to another exemplary embodiment of the present disclosure, the optical components can include a multi-mode optical waveguide which can be used to convert the first electro-magnetic radiation(s) into multiple propagation modes which are part of the second electro-magnetic radiation(s). The optical components can modify a phase and/or an amplitude of a wavefront of the first electro-magnetic radiation(s). The optical components can include at least one objective lens which, when impacted by the at least one first converted electro-magnetic radiation, can provide the second electro-magnetic radiation(s) at multiple foci n a lateral direction and/or an axial direction. At least one imaging system can be provided which generates at least one image of at least one portion of the sample based on a third radiation which is a return radiation of the second electro-magnetic radiation(s). The multi-mode optical waveguide can be selected to have characteristics which modify the at least one second electro-magnetic radiation so that the imaging system is capable of generating the at least one image. Characteristics and sizes of the optical components can be dependent on and/or relevant to (i) depth of focus of the at least one second electro-magnetic radiation into the sample, (ii) a resolution of an image of at least one portion of the sample, and/or (iii) an imaging range of the optical components.

According to a still another exemplary embodiment of the present disclosure, method and computer-accessible medium (with software thereon) can be provided for generating a specific design of an optical system. For example, the software can be used to modify a computer to perform various specialized computer-executed instructions, including receiving information regarding a design specification of the optical system; evaluating the design specification to determine whether at least one predetermined condition is met; using a computer-based procedure, generating a simulated design based on the design specification; and generating the specific design based on an evaluation of the simulated design. The computer can also be modified to evaluate at least one electro-magnetic radiation provided to at least one sample by the optical system, whereas results of the evaluation can be used by the computer to generate the simulated design and/or the specific design. The evaluation by the computer can include analyzing (i) resolution, (ii) depth of focus, (iii) foci, (iv) intensity distribution uniformity, and/or (v) penetration depth of the electro-magnetic radiation(s).

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIGS. 2A and 2B are schematic diagrams of swept-source OCT or OFDI systems with mirror tunnel fiber probe according to exemplary embodiments of the present disclosure;

FIG. 4A is a diagram of grin lens based mirror tunnel fiber probe according to exemplary embodiments of the present disclosure;

FIG. 4B is a diagram of ball lens based mirror tunnel fiber probe according to exemplary embodiments of the present disclosure;

FIGS. 5A and 5B are diagrams of double-cladding fiber based mirror tunnel fiber probe according to exemplary embodiments of the present disclosure;

FIGS. 8A-8C are a set of illustrations of an exemplary simulation of beam propagation scheme of mirror tunnel fiber probe in geometric optics domain and intensity distribution analysis in image space in wave optics diffraction domain according to exemplary embodiments of the present disclosure;

FIGS. 11A-11C are charts illustrating modifying mirror tunnel's aspect ratio (length/diameter) to increase the energy in higher order mode according to exemplary embodiments of the preset disclosure;

FIG. 14 is a photograph of an exemplary mirror tunnel fiber probe and a ring pattern on a transverse plane introduced by a multi-mode propagation according to exemplary embodiments of the present disclosure;

FIG. 17A is a diagram of a catheter with mirror tunnel fiber probe and rotary junction used for circumferential scan on coronary artery wall according to exemplary embodiments of the present disclosure;

FIG. 17B is a diagram of a catheter with the exemplary mirror tunnel fiber probe and the exemplary micro-motor used for circumferential scan on a coronary artery wall according to exemplary embodiments of the present disclosure;

FIG. 17C is a diagram of a tethered swallowable capsule with the exemplary mirror tunnel fiber probe for the GI tract imaging according to exemplary embodiments of the present disclosure;

FIG. 17D is a diagram of a swallowable capsule with the exemplary mirror tunnel fiber probe and the exemplary micro-motor used for circumferential scan for the GI tract imaging according to exemplary embodiments of the present disclosure;

FIG. 17E is a diagram of a needle probe with the exemplary mirror tunnel according to exemplary embodiments of the present disclosure;

FIG. 17F is a diagram of a balloon probe with the exemplary mirror tunnel according to exemplary embodiments of the present disclosure;

FIG. 18 is a schematic illustration of a 1D planar mirror tunnel based focusing optics system for multi-focus imaging in lateral dimension according to exemplary embodiments of the present disclosure;

FIGS. 38(a)-38(f) are illustrations of exemplary optimal design parameter ranges for probes with imaging range 0.5-2.5 mm, rigid length less than 10 mm and aperture diameter less than 0.2 mm operated at wavelength 800 nm and 1300 nm, respectively, according to another exemplary embodiment of the present disclosure which can be implemented with any one of the exemplary embodiments of the present disclosure described herein;

FIGS. 39(a)-39(e) are illustrations of exemplary optimal design parameter ranges for the exemplary probes with imaging range 0.5-2.5 mm, rigid length less than 10 mm and aperture diameter less than 0.5 mm operated at wavelength 800 nm.

FIGS. 40(a)-40(e) are illustrations of the exemplary optimal design parameter ranges for the exemplary probes with imaging range 0.5-2.5 mm, rigid length less than 10 mm and aperture diameter less than 0.5 mm operated at wavelength 1300 nm, according to another exemplary embodiment of the present disclosure which can be implemented with any one of the exemplary embodiments of the present disclosure described herein;

FIGS. 41(a)-41(f) are illustrations of the exemplary optimal design parameter ranges for exemplary catheter and needle probes with imaging range 0.5-2.5 mm, rigid length less than 20 mm and aperture diameter less than 1 mm operated at wavelength 800 nm, according to another exemplary embodiment of the present disclosure which can be implemented with any one of the exemplary embodiments of the present disclosure described herein;

FIGS. 46(a)-46(g) are illustrations of the exemplary optimal design parameter ranges for the exemplary optimal design parameter ranges for the exemplary capsule probes with imaging range 4.5-7 mm, rigid length less than 20 mm and aperture diameter less than 3 mm operated at wavelength 1300 nm, according to another exemplary embodiment of the present disclosure which can be implemented with any one of the exemplary embodiments of the present disclosure described herein;

FIGS. 47(a)-47(g) are illustrations of the exemplary design parameter ranges for balloon probes with imaging range 9-12 mm, rigid length less than 20 mm and aperture diameter less than 3 mm operated at wavelength 800 nm, according to another exemplary embodiment of the present disclosure which can be implemented with any one of the exemplary embodiments of the present disclosure described herein.

Figure 1B:
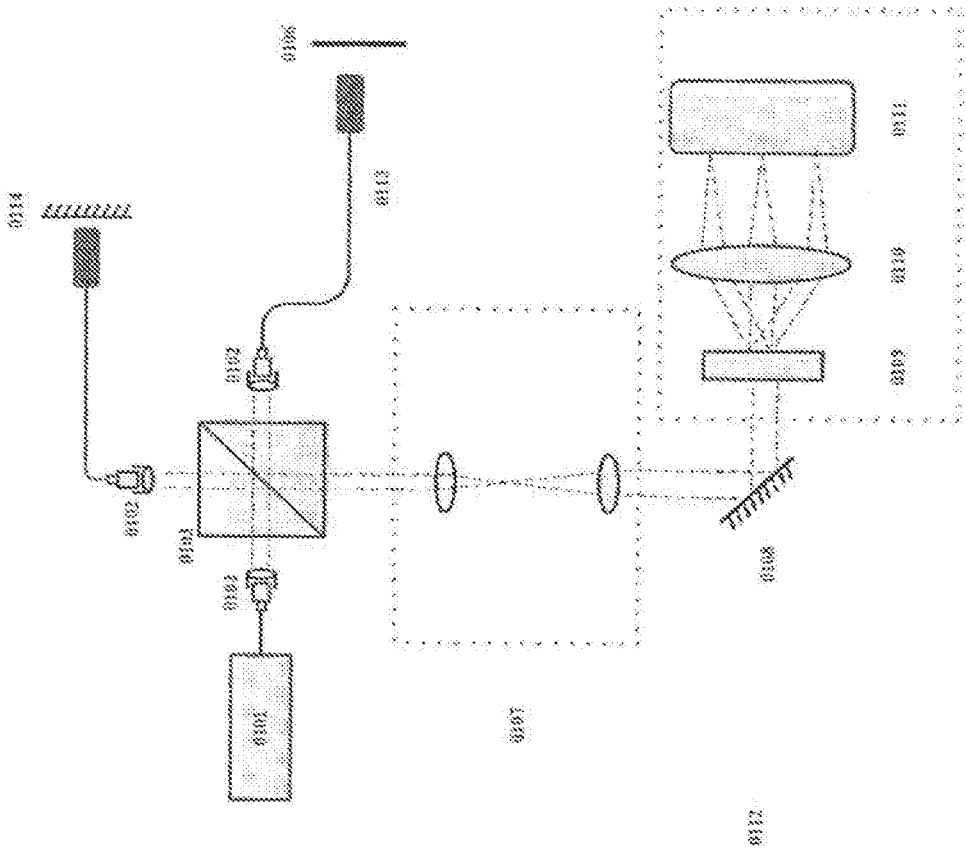
FIGS. 1A and 1B are schematic diagrams of spectrometer based spectral-domain OCT systems with mirror tunnel fiber probe according to exemplary embodiments of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure and the appended claims.

DETAILED DESCRIPTION OF EXEMPLARY EMBODIMENTS

Various certain embodiments presented in the present disclosure can be based on exemplary optical designs and configurations that incorporate, e.g., a mirror tunnel into conventional lens system for depth-of-focus extension. It is particularly useful for high-resolution optical imaging system that benefits from an extended depth-of-focus. The exemplary embodiments of the present disclosure include a mirror tunnel fiber probe and an OCT system with cellular level resolution, the mirror tunnel fiber probe can be used for probing techniques such as needle probe, balloon probe, GI tract capsule, and intravascular catheter. With the help of mirror tunnel based focusing optics, probing OCT system maintains same depth-of-focus as a conventional OCT system but more than 10-fold improvement in resolution, which enables in-vivo cellular level imaging, and makes the detection and monitoring of disease that is caused by cells and subcellular structures that are irresolvable by conventional OCT possible.

Further, various embodiments presented in the present disclosure can be based on an optical design that is able to generate multiple pseudo-Bessel beams with a configurable working distance suitable for implementation in a miniaturized catheter or endoscope optical system for DOF extension. Coaxial foci of pseudo-Bessel beams in response to different propagation modes (coaxially focused multi-mode (CAFM) beam) originated from one single input Gaussian beam significantly extend the effective imaging range of a Gaussian beam optical system without increasing system complexity, which facilitates the clinical translation of this technique for in-vivo cellular-level imaging of human internal organ. The design process and optimization method of this self-imaging wavefront division optical system and the physical properties of the pseudo-Bessel beams are also included in this disclosure.

Figure 1A:
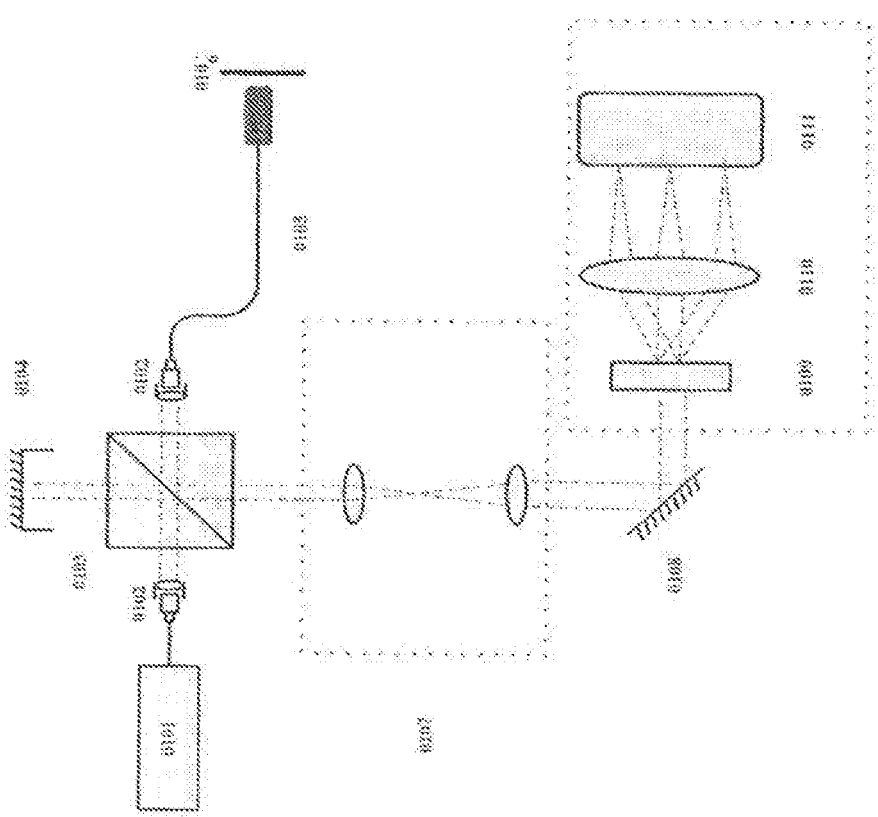

Exemplary schematics of spectral-domain OCT system are shown in FIGS. 1A and 1B. FIG. 1A illustrates an exemplary system for a common-path mirror tunnel fiber probe according to certain exemplary embodiments of the present disclosure. For example, light is emitted from a broadband light source (0101), split by beam splitter (0103), portion of the light is coupled into common-path mirror tunnel fiber probe (0105) through fiber port collimator (0102), illuminates the sample (0106), the rest of the light is absorbed by beam dumper (0104). Collimated beam that carries interference signal is expanded by a telescope (0107), reflected by mirror (0108), coupled into spectrometer detection arm (0112), which consists of grating (109), focusing lens set (0110) and a line-scan camera (0111). Dispersion is minimized as sample and reference light go through the same path. 1B is the system for non-common-path mirror tunnel fiber probe (0113), a separate reference arm (0114) is required to provide the reference signal, dispersion due to fiber length mismatch between sample and reference arm needs to be compensated either numerically or by hardware dispersion compensation.

An exemplary schematic diagram of swept-source OCT or OFDI systems are illustrated in FIGS. 2A and 2B according to certain exemplary embodiments of the present disclosure. In particular, FIG. 2A shows the exemplary system for common-path mirror tunnel fiber probe (0204). Light emitted by a broadband swept-source laser (0201) is split by a fiber coupler (0202), one portion of the light goes through optical circulator (0203), illuminates the sample (0205); the other portion of the light is input into balanced photodetector (0206) to reduce spectrum DC noise. FIG. 2B shows the system for non-common-path mirror tunnel fiber probe (0207), a separate reference arm (0208) is required. Polarization mode dispersion (PMD) may degrade image quality for non-common-path design due to uneven bending and twisting of the fiber between sample and reference arms, and it is minimized by applying polarization-diversity detection module (0211) consisting of one non-polarizing beam splitter (0209), two polarizing beam splitters (0210) and two balanced photodetectors (0206). Balanced detection is implemented to reduce common mode noise, after subtracting signals of two channels, spectrum DC are cancelled, but fringe signals are doubled due to pi phase shift.

Figure 3:
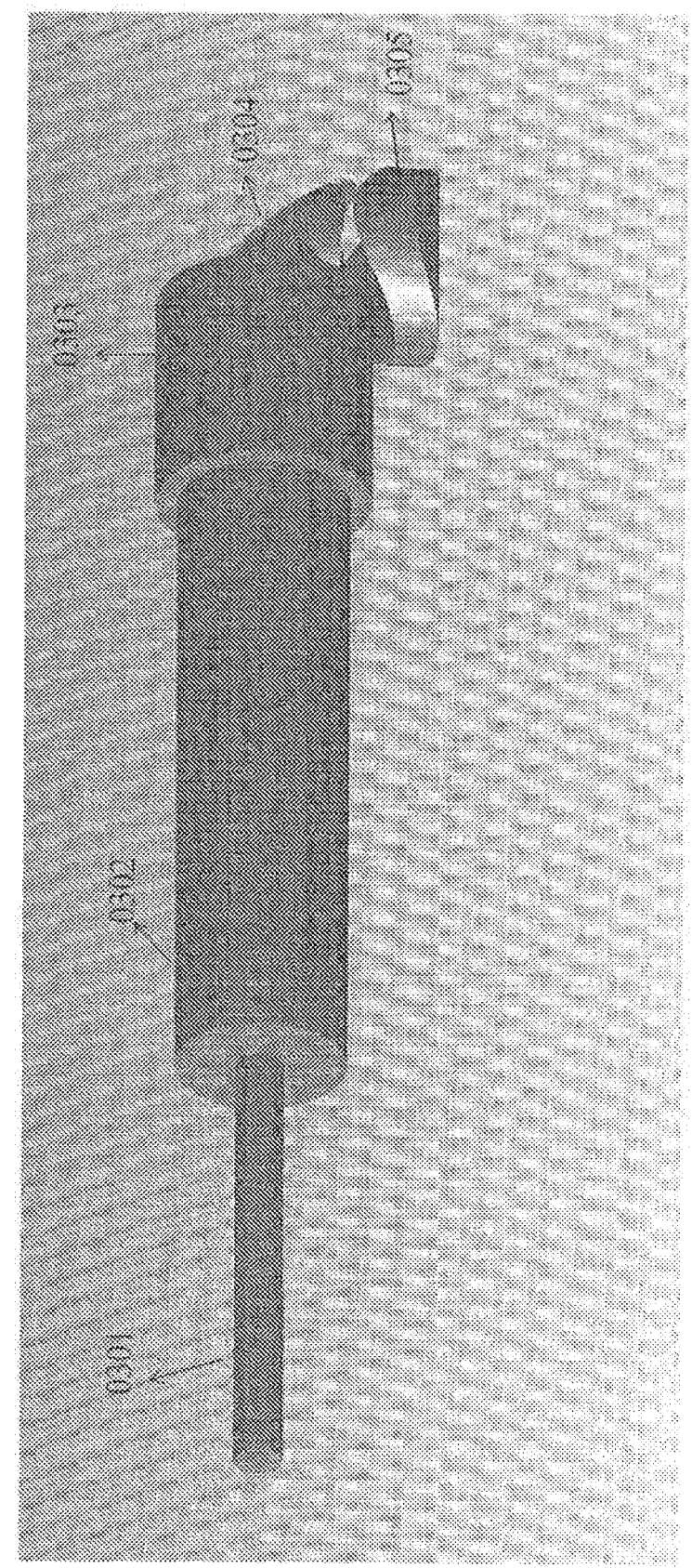
FIG. 3 is a diagram of mirror tunnel fiber probe according to exemplary embodiments of the present disclosure.

An exemplary mirror tunnel fiber probe is shown in FIG. 3. For example, a single mode fiber (0301) guides the input. Multiple propagation modes are generated by mirror tunnel (0302), and expanded in spacer (0303). Grin lens (0304) focuses the beam, followed by a right-angle prism (0305) for side-view imaging. A sheath (0306) is used to protect the fiber probe. The aspect ratio of mirror tunnel determines number of modes generated and the energy distribution between modes. The length of spacer determines the size of aperture for each mode, and together with the focusing power of grin lens determines the effective NA of each mode. The fabrication process of this mirror tunnel fiber probe includes:

(a) the input single mode fiber distal end is spliced with a multimode fiber, which is used as a mirror tunnel in this miniaturized fiber probe;
(b) cleave the multimode fiber according to designed length;
(c) splice a large core multimode fiber to distal end, the large core multimode fiber is used as a spacer, so its core size determines the maximum available aperture size;
(d) polish the spacer to designed length;
(e) attach grin lens to distal end, use five-axis stage to ensure a good alignment and minimize the back reflection from grin lens-air interface by slightly misaligning the optics; and
(f) attach right-angle prism to grin lens, use five-axis stage to maximize the back reflection from prism leg-air interface as this back reflection is used as reference in a common-path fiber probe.

Refractive index matched UV epoxy is applied for attaching optics, and in order to reduce unnecessary back reflection and optimize reference power, real-time monitoring is required for this process, typically the fiber probe being fabricated is connected to an OCT system sample arm, the spectrum signal is displayed in real time during alignment process.

FIG. 4A shows an exemplary mirror tunnel fiber probe of single mode fiber (0401), mirror tunnel (0402), spacer (0403), grin lens (0404), and right-angle prism (0405) according to an exemplary embodiment of the present disclosure. FIG. 4B shows an exemplary mirror tunnel fiber probe using ball lens (0406) instead of grin lens for focusing, and the ball lens is polished for side-view imaging according to another exemplary embodiment of the present disclosure.

Figure 6:
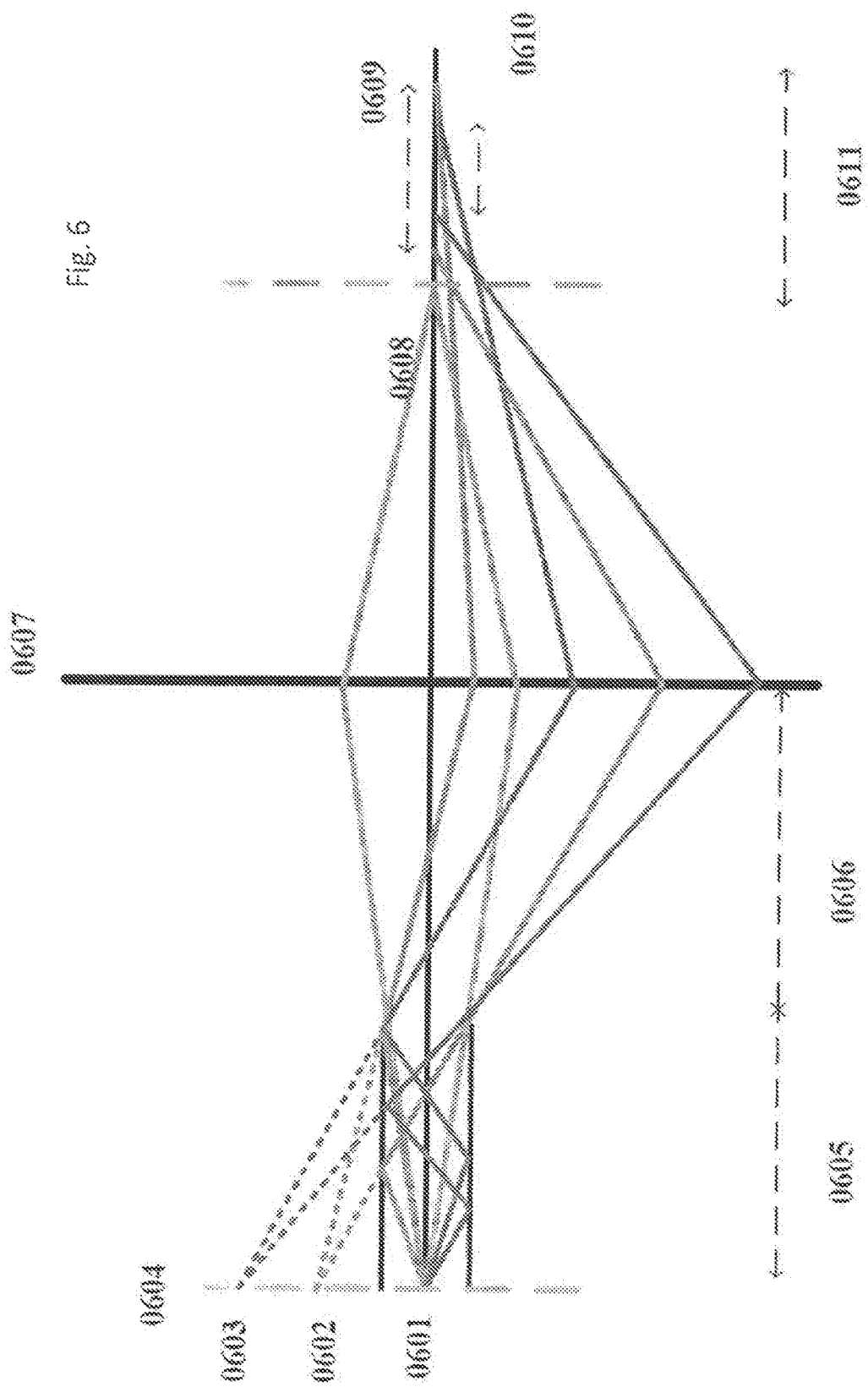
FIG. 6 is an illustration of mirror tunnel fiber probe in geometric optics domain according to exemplary embodiments of the present disclosure.

FIG. 5A shows an exemplary mirror tunnel fiber probe including of double-cladding fiber (0501), mirror tunnel (0502), spacer (0503), grin lens (0504), and right-angle prism (0505) according to an exemplary embodiment of the present disclosure. FIG. 5B illustrates an exemplar mirror tunnel fiber probe using ball lens (0506) as focusing optics and double-cladding fiber for multi-modality imaging according to another exemplary embodiment of the present disclosure. For example, the core of double-cladding fiber is used to transmit OCT signal, inner cladding can be used for delivery and detection of fluorescence, autofluorescence, Raman and spectroscopy signal. This enables the application of mirror tunnel fiber probe in multi-modality imaging FIG. 6 illustrates multiple modes propagation in the exemplary mirror tunnel fiber probe according to an exemplary embodiment of the present disclosure. For example, the original point source (0601) is the source for zero order mode, mirror tunnel (0605) introduces multiple propagation modes by internal reflection. $1^{st}$ order mode is introduced by internal reflection once, and the mirror image of original point source is considered as the virtual source (0602) for $1^{st}$ order mode; $2^{nd}$ order mode is introduced by internal reflection twice, double reflection mirror image of original point source is considered as the virtual source (0603) for $2^{nd}$ order mode. Original point source and higher order mode virtual source are all or mostly located on the object plane (0604). As mirror tunnel is a radial-symmetric system, mode order higher than zero can be originated from a virtual ring source instead of a point source. After spacer (0606), different propagation modes of beam can be focused by a focusing optics (0607). Higher order modes can be focused onto a deeper region than zero order mode focus (0608). First order mode focusing region (0609), second order mode focusing region (0610), and even higher order mode focusing region together can extend the depth of focus of the optical system (0611).

Figure 7:
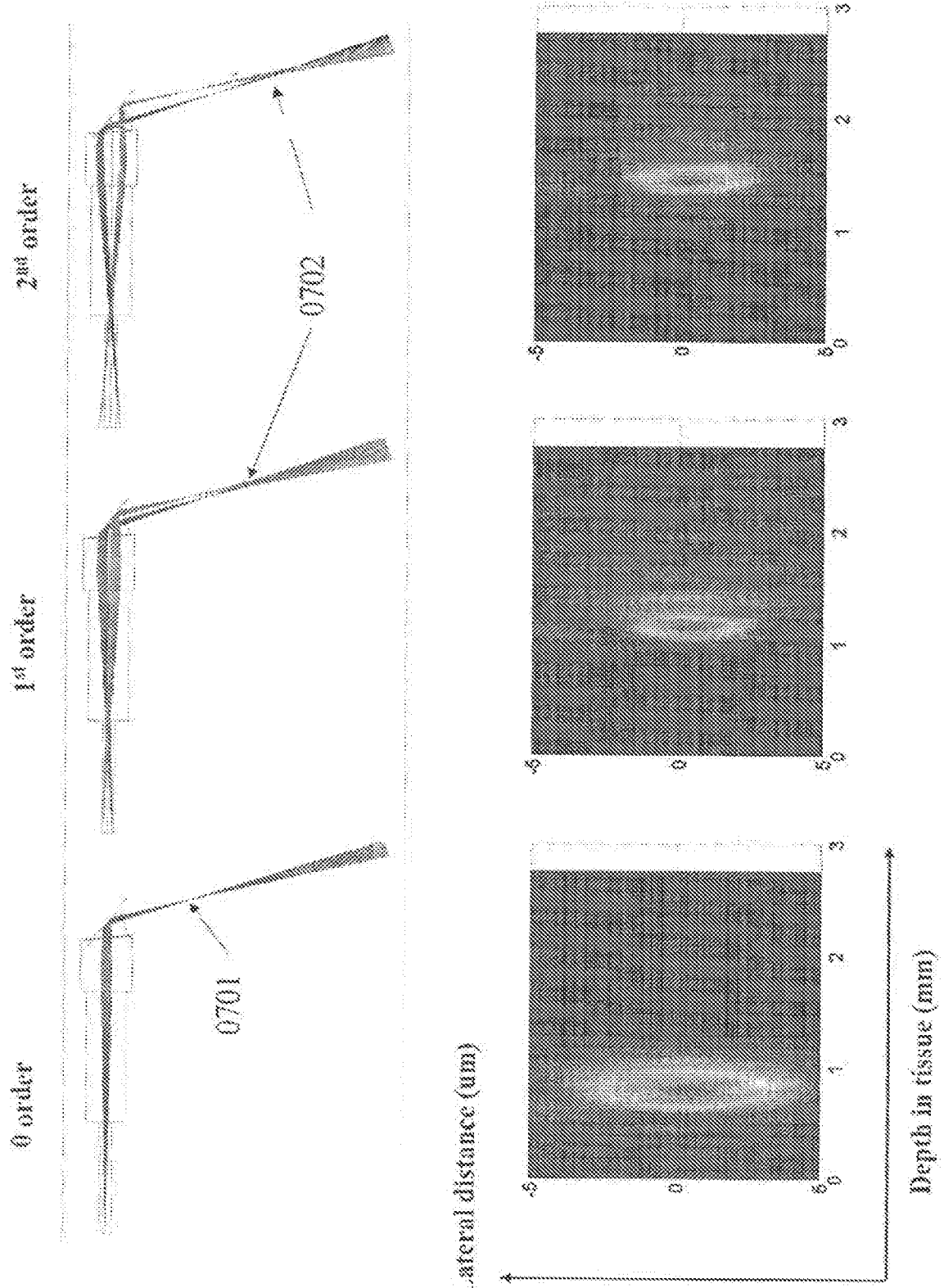
FIG. 7 is a set of illustrations of an exemplary simulation of multi-mode propagation scheme of mirror tunnel fiber probe in geometric optics domain and intensity distribution analysis in image space in wave optics diffraction domain according to exemplary embodiments of the present disclosure.

FIG. 7 shows an exemplary ray tracing simulation and diffraction field simulation according to exemplary embodiments of the present disclosure. The top row is the ray tracing simulation, second row is the field distribution calculated according to Fresnel diffraction. Columns from left to right are 0 order mode, $1^{st}$ order mode, and $2^{nd}$ order mode respectively. The zero order mode focus is similar to a Gaussian beam focus (0701), the $1^{st}$ order and $2^{nd}$ order mode foci can be considered as foci generated by corresponding annular rings of original Gaussian beam (0702).

FIGS. 8A-8C illustrate the exemplary simulation of propagation of multiple modes according to exemplary embodiments of the present disclosure. In particular, FIG. 8A shows the exemplary ray tracing simulation of multiple propagation modes in mirror tunnel fiber probe. FIG. 8B shows the exemplary simulated intensity distribution in image space according to Fresnel diffraction, and FIG. 8C shows the exemplary simulated on-axis intensity distribution in image space. According to the exemplary simulation, multiple on-axis foci can be introduced in image space. Higher order mode of beam is focused through a larger aperture, and its intensity is concentrated on a deeper region, therefore the effective NA is maintained. Different modes may interfere, which generates local intensity peak.

Figure 9:
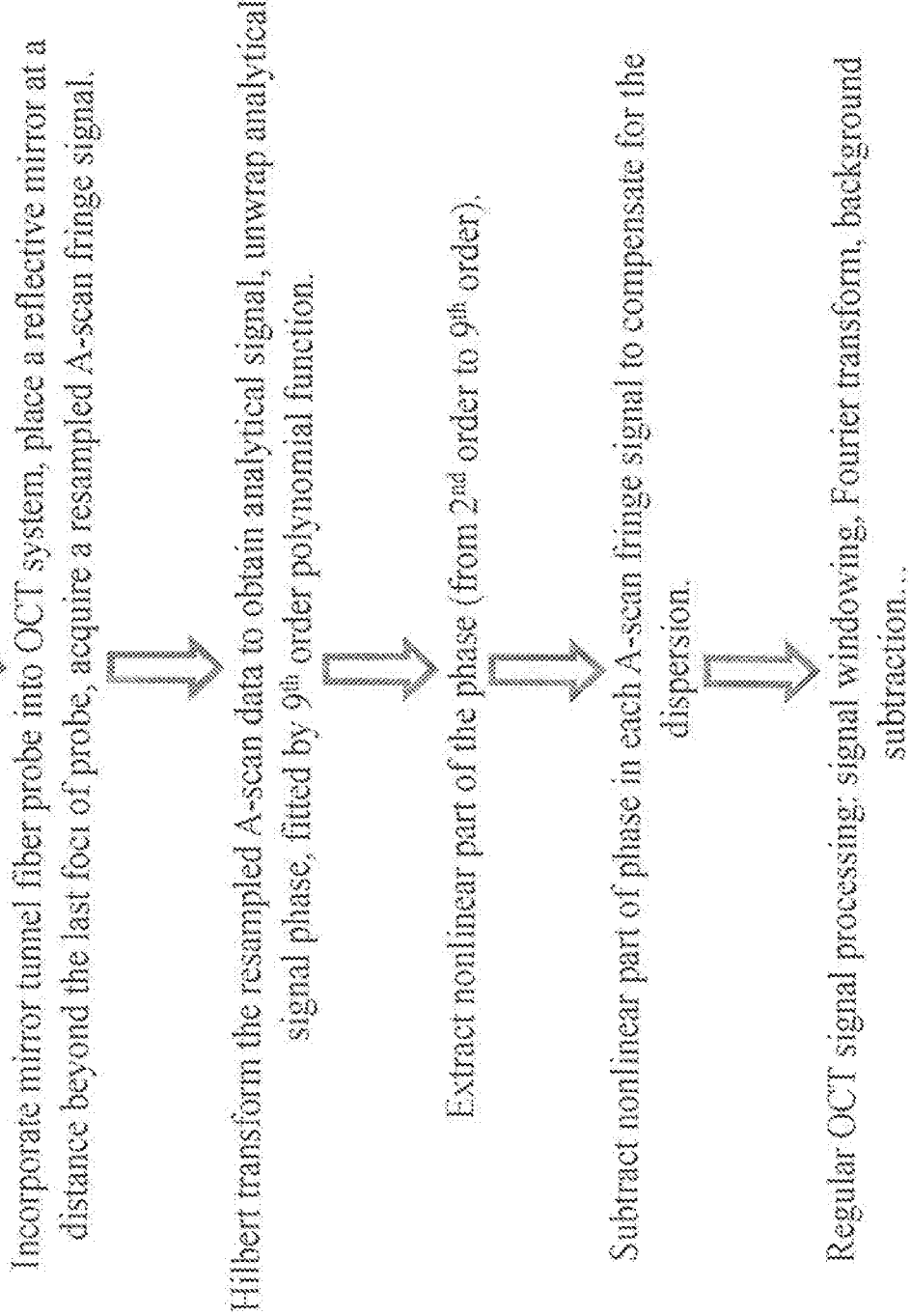
FIG. 9 is a procedure flow diagram for numerical dispersion compensation according to exemplary embodiments of the present disclosure.

FIG. 9 shows a diagram of an exemplary procedure for numerical dispersion compensation. In order to achieve high axial resolution in OCT image, dispersion is to be corrected when necessary, according to exemplary embodiments of the present disclosure. For a spectrometer based spectral-domain OCT system, first the spectrometer needs to be calibrated, acquired A-scan fringe signal can be converted to uniform wavenumber sampling space. Acquire one A-scan fringe signal of a point reflector such as a mirror, use Hilbert transform to calculate the phase of the fringe signal. According to the phase evolution with respect to wavenumber of this point reflector, the intrinsic dispersion of the system can be calculated, which is the nonlinear part of the phase. By subtracting this nonlinearity from sample A-scan signal phase, the dispersion introduced by the system can be minimized.

Figures 10A, 10B, 10C:
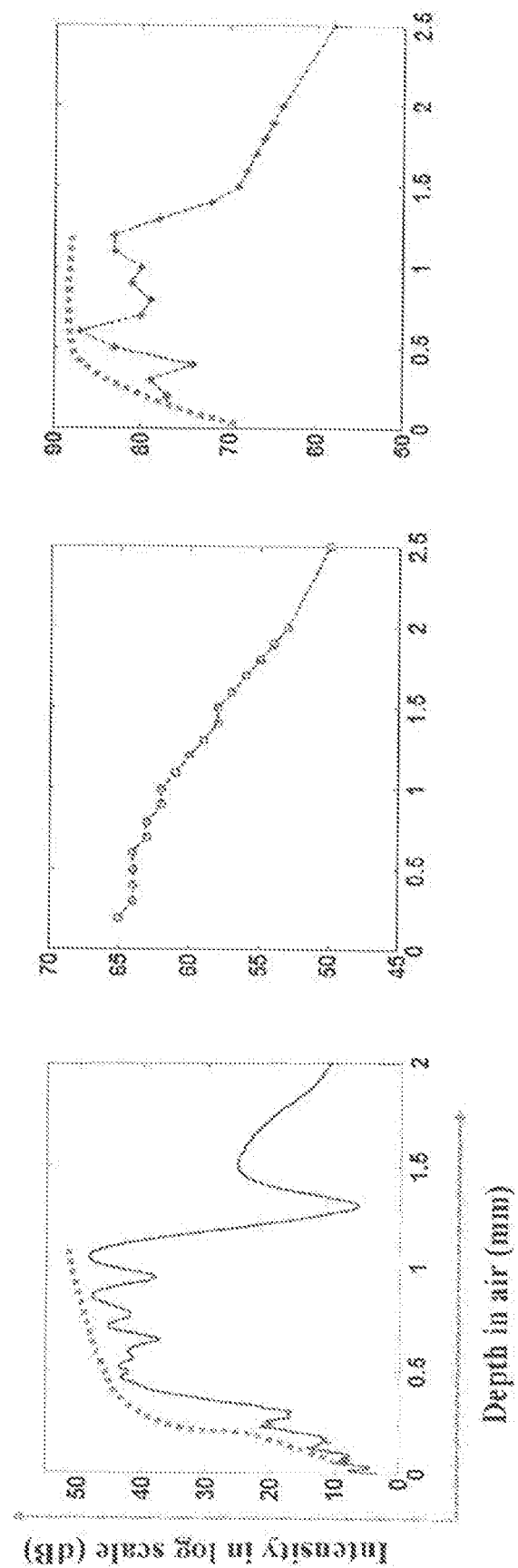
FIGS. 10A-10C are charts illustrating modifying intensity distribution among foci for system sensitivity roll-off and tissue attenuation compensation according to exemplary embodiments of the present disclosure.

FIGS. 10A-10C show graphs indicating how to modify the intensity distribution between modes to compensate for OCT system sensitivity roll-off or tissue attenuation according to exemplary embodiments of the present disclosure. In particular, FIG. 10A shows the exemplary simulated on-axis intensity distribution in image space in logarithm scale, intensity of the focus increases as increasing the order of mode to compensate for tissue attenuation and system sensitivity roll-off since higher order mode is focused deeper and has a longer optical pathlength to reference surface. FIG. 10B shows the exemplary measured sensitivity roll-off of the system. FIG. 10C shows the exemplary measured sensitivity at each depth position (Z-scan), from which we see a more uniform distribution of intensity along depth than the simulated intensity along depth when no system sensitivity roll-off is considered. Further, the higher order mode can be designed to contain more energy to increase imaging depth of the system, which can be done by modifying the aspect ratio of mirror tunnel's length to diameter.

FIGS. 11A-11C illustrate graphs indicating a modification of the mirror tunnel's aspect ratio to increase the energy in high order mode. In particular, FIG. 11A shows the exemplary simulated on-axis intensity distribution when the ratio of mirror's length to diameter is 16. FIGS. 11B and 11C illustrate the exemplary simulations for ratio of 20 and 24 respectively. It shows that by increasing the ratio of length to diameter, more energy is distributed into high order mode, which can be used to compensate for tissue attenuation since higher order mode is focused into a deeper region in tissue.

Figure 12:
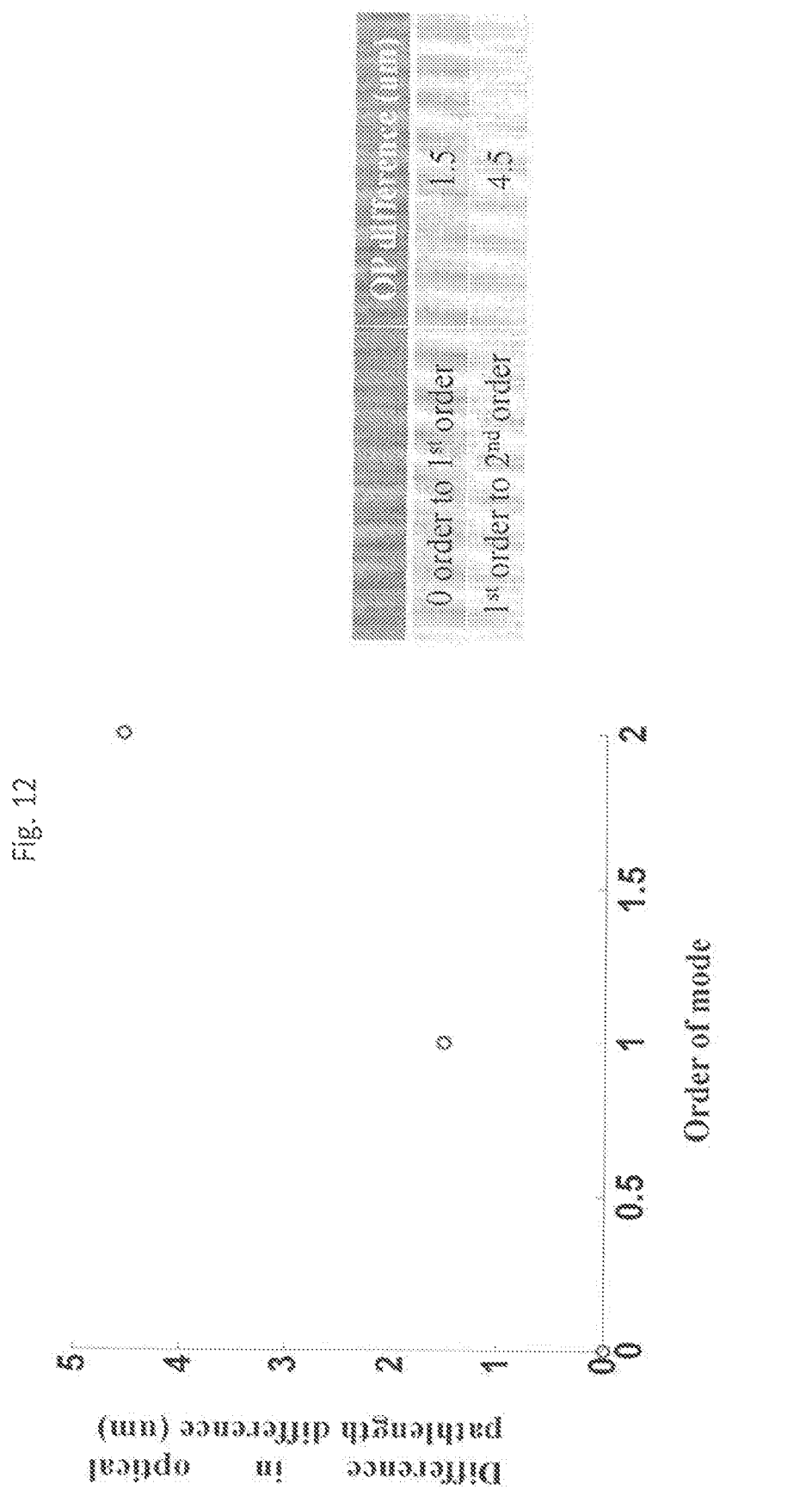
FIG. 12 is an illustration of optical pathlength (op) difference between neighboring modes introduced by mirror tunnel according to exemplary embodiments of the present disclosure.

FIG. 12 illustrates optical pathlength (op) difference between neighboring modes introduced by mirror tunnel according to exemplary embodiments of the present disclosure. The op difference between 0 order and $1^{st}$ order modes is estimated to be 1.5 µm, and the op difference between $1^{st}$ and $2^{nd}$ order modes is estimated to be 4.5 µm. As the op difference between neighboring modes are comparable to OCT system axial resolution and image pixel distance, no noticeable gap is observed in the acquired image. For future exemplary embodiments of the present disclosure, op difference between neighboring modes can be increased for applications that need to distinguish signal acquired from different spatial frequency bands or from different annular apertures.

Figure 13A:
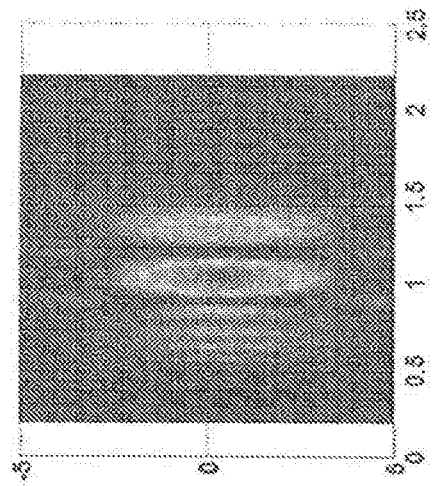
FIGS. 13A-13D are illustrations of simulated wavelength dependent field intensity distributions on an image space to show the effect of chromatic focal shift according to exemplary embodiments of the present disclosure.
Figure 13B:
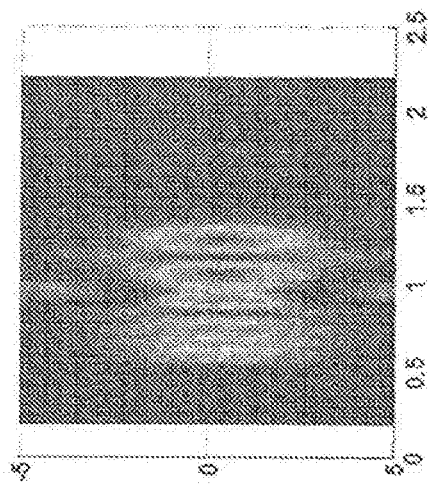
Figure 13C:
Figure 13D:
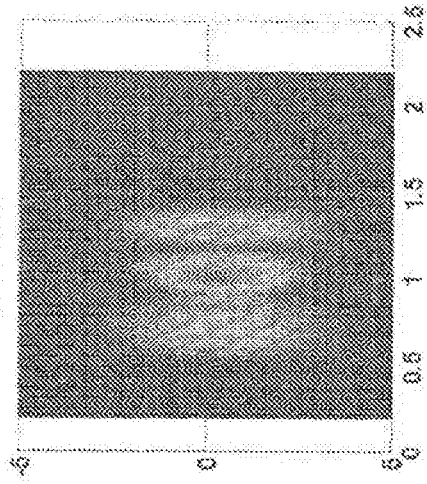

FIGS. 13A-13D illustrate exemplary intensity maps indicating chromatic focal shift effect of a broadband light source based OCT system according to an exemplary embodiment of the present disclosure. The simulated field intensity distributions on image space at center wavelength 800 nm (FIG. 13B) and two ends of the spectrum 650 nm (FIG. 13A) and 950 nm (FIG. 13C) are presented, the focal depth shifts slightly between wavelengths, and this chromatic focal shift effect becomes more obvious as the spectrum of light source broadens. This effect can degrade the actual axial resolution of OCT as the effective spectrum narrows at each depth, but it also reduces the gap between neighboring foci as shown in FIG. 13D that illustrates overlapped field of three wavelengths. The exemplary mirror tunnel multi-focus imaging technique benefits from this effect since the overall spectrum intensity distribution along depth becomes more uniform.

FIG. 14 shows a photograph of exemplary embodiments of the present disclosure. In particular, a single mode fiber is spliced with a multimode fiber, which is used as mirror tunnel (1401). A spacer (1402) is attached to the mirror tunnel, followed by a grin lens (1403) and prism (1404). The rigid length of the optics is less than 4 mm, and the maximum diameter is 500 µm. On the transverse plane of the beam emitted from the probe, concentric ring pattern is observed as multiple modes of light coexist.

Figure 15:
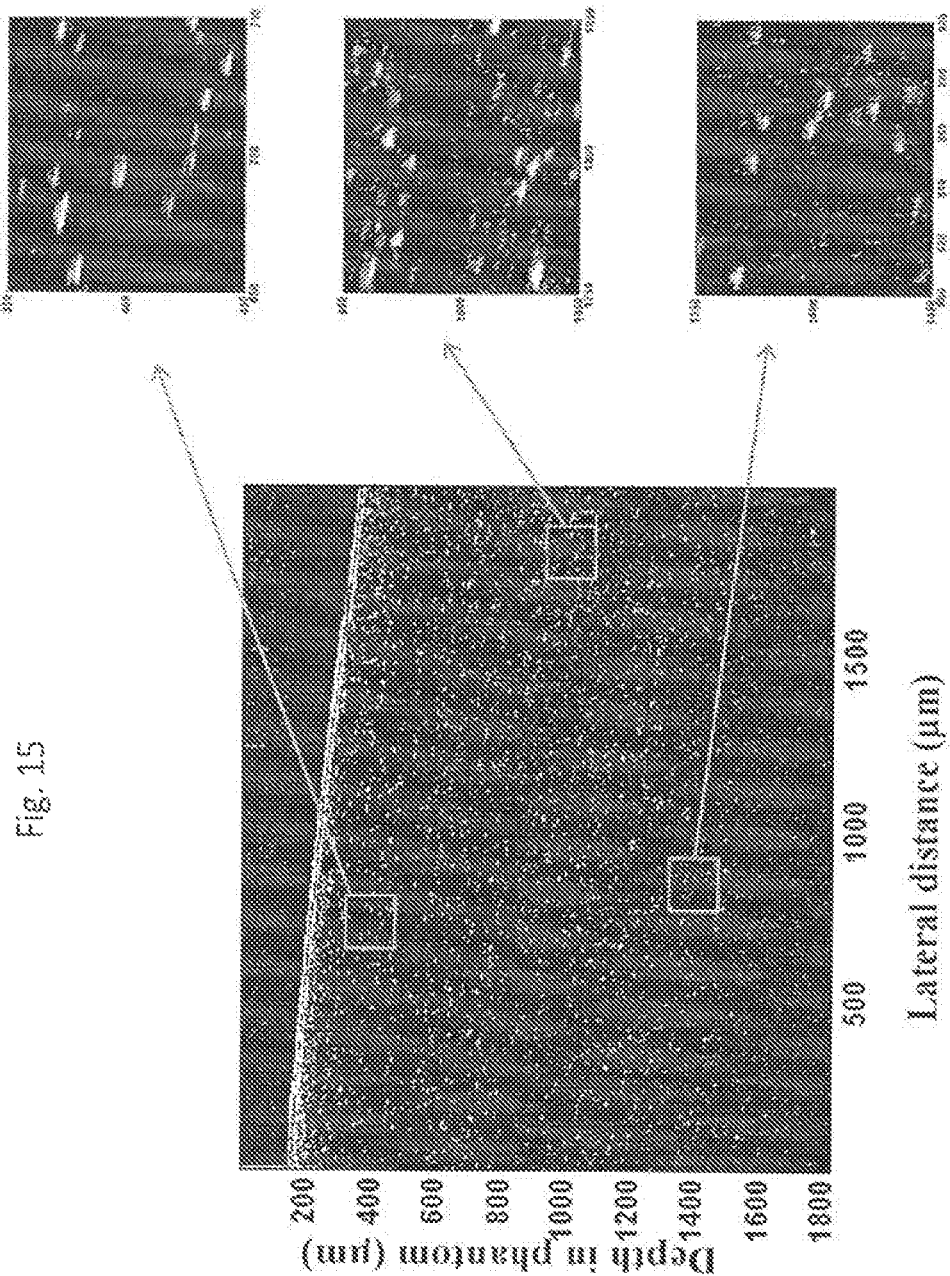
FIG. 15 is an exemplary B-scan image of a scattering phantom with 2-μm micro-sphere, which demonstrates a depth-of-focus extension introduced by the exemplary mirror tunnel fiber probe according to exemplary embodiments of the present disclosure.

FIG. 15 shows an exemplary B-scan image of scattering phantom that contains 2 µm micro-sphere acquired by mirror tunnel fiber probe and a high-resolution spectrometer based spectral-domain OCT system according to an exemplary embodiment of the present disclosure. For example, the exemplary mirror tunnel fiber probe is attached to a translational stage, and the movement of the stage is synchronized with the OCT system data acquisition. Scattering particles can be clearly seen throughout more than 1.6 mm depth in the phantom. No noticeable defocus aberration is observed in the image. According to Rayleigh criteria, 5 µm resolution objective provides a depth of focus of 50 µm at 800 nm wavelength, therefore a more than 20-fold improvement is achieved according to the technique provided by the present disclosure.

Figure 16:
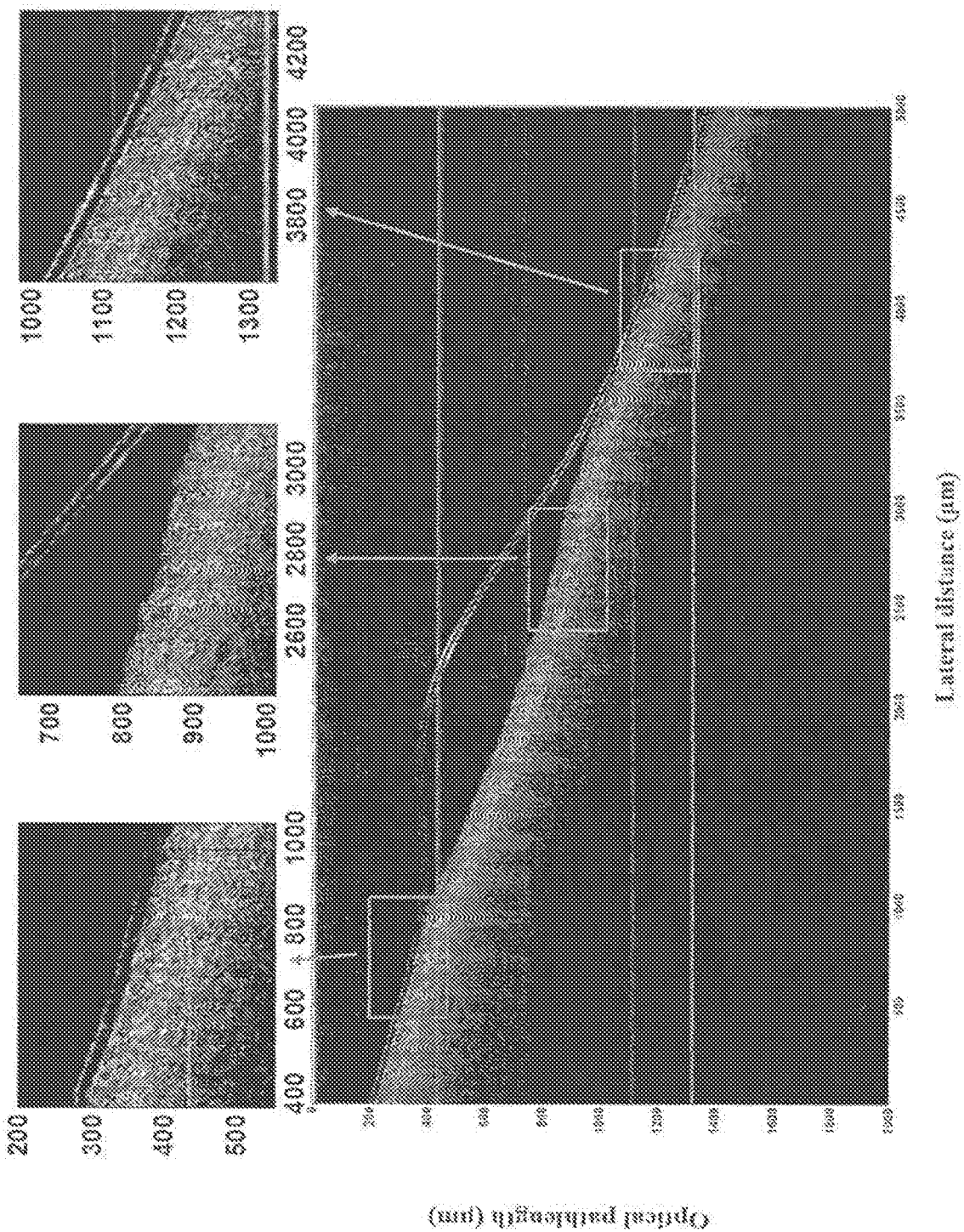
FIG. 16 is an exemplary B-scan image of an ex-vivo swine aorta tissue acquired by exemplary embodiments of the present disclosure.

FIG. 16 shows an exemplary B-scan image of swine aorta tissue acquired by exemplary embodiments of the present disclosure. Image is acquired at 24 us integration time and 35 mW fiber probe output power. Cellular level image is obtained with more than 1.5 mm ranging depth, which demonstrates mirror tunnel fiber probe's long depth of focus, cellular level resolution, and real-time tissue imaging capability.

FIGS. 17A-17F show schematic diagrams of the in-vivo catheter, swallowable capsule, needle probe and balloon probe design of mirror tunnel fiber probe according to exemplary embodiments of the present disclosure. As illustrated in FIG. 17A, a rotary junction (1701) is used for circumferential scan on coronary artery wall (1705), side-view mirror tunnel fiber probe (1704) is connected to a rotary junction through a single mode fiber (1702) inside drive shaft (1703). As shown in FIG. 17B, a forward-looking mirror tunnel fiber probe (1706) stays stationary when imaging, a right-angle prism is attached to a micro-motor (1707), circumferential scan is enabled by rotation of the micro-motor. FIG. 17C shows a tethered swallowable capsule (1708) for GI tract (1709) imaging. FIG. 17D shows a micro-motor based swallowable capsule for GI tract imaging. FIG. 17E illustrates a mirror tunnel needle probe (1710), and FIG. 17F shows a mirror tunnel balloon probe (1711).

FIG. 18 illustrates a 1D planar mirror tunnel based lateral dimension multi-focus imaging system according to an exemplary embodiment of the present disclosure. The input point source or single mode fiber tip (1801) is placed at the center of two parallel planar mirrors (1802). Virtual point sources are generated on the object plane (1803), and line up in one dimension. Each propagation mode is originated from the corresponding virtual source, and then focused (1805) onto image plane (1804). All or most propagation modes form a foci array on image plane in response to the virtual source array on object plane, which has unique illumination and detection properties.

Figure 19:
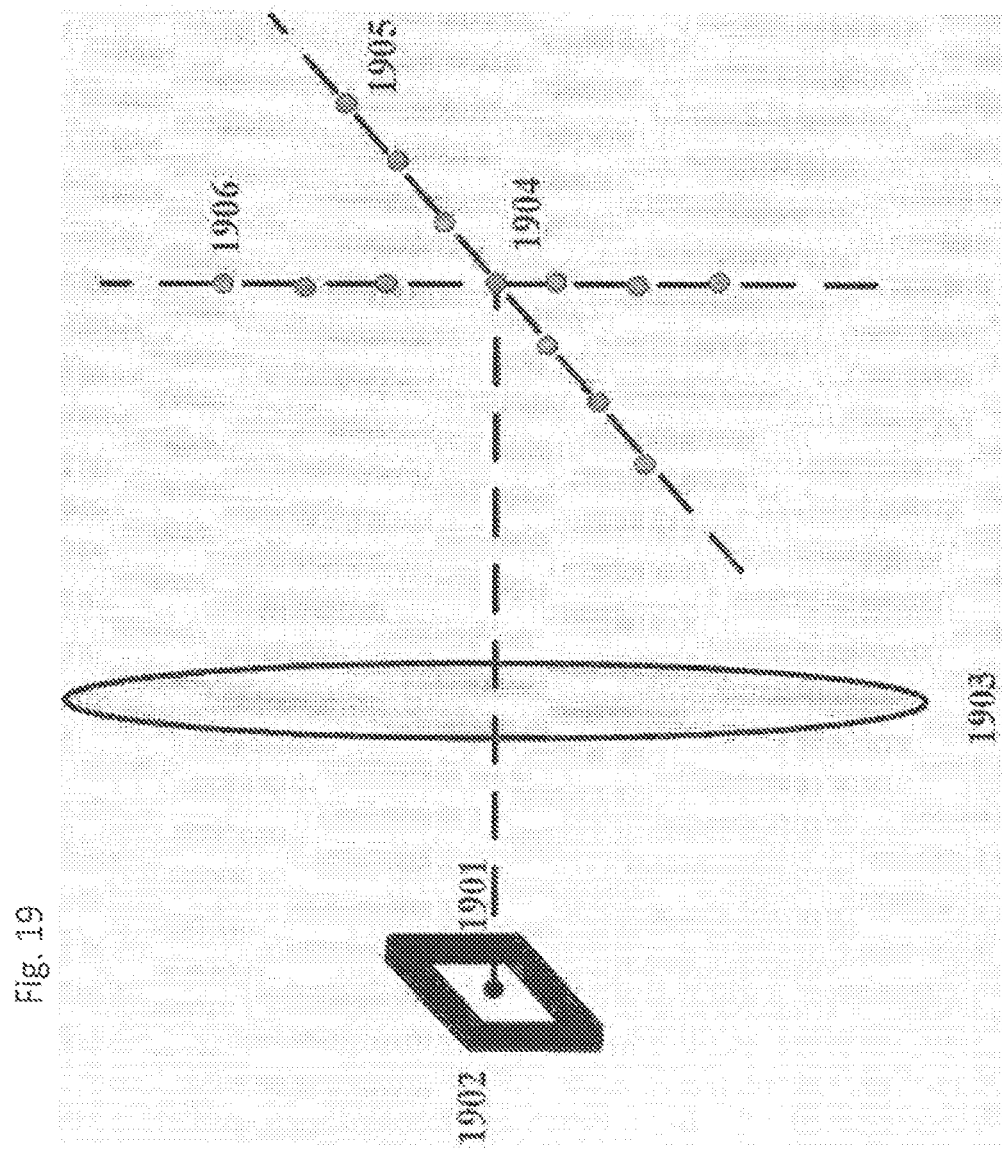
FIG. 19 is a schematic illustration of a rectangular mirror tunnel based focusing optics system for two-axis multi-focus imaging according to exemplary embodiments of the present closure.

FIG. 19 illustrates a rectangular mirror tunnel based two-axis multi-focus imaging system according to an exemplary embodiment of the present disclosure. Similar to the 1D planar mirror tunnel focusing system described in FIG. 18, the input point source or single mode fiber tip (1901) is placed at the center of rectangular mirror tunnel (1902). After focusing (1903), on image plane (1904), two foci arrays are formed along horizontal axis (1905) and vertical axis (1906) respectively in response to the virtual sources generated by rectangular mirror tunnel.

Figure 20:
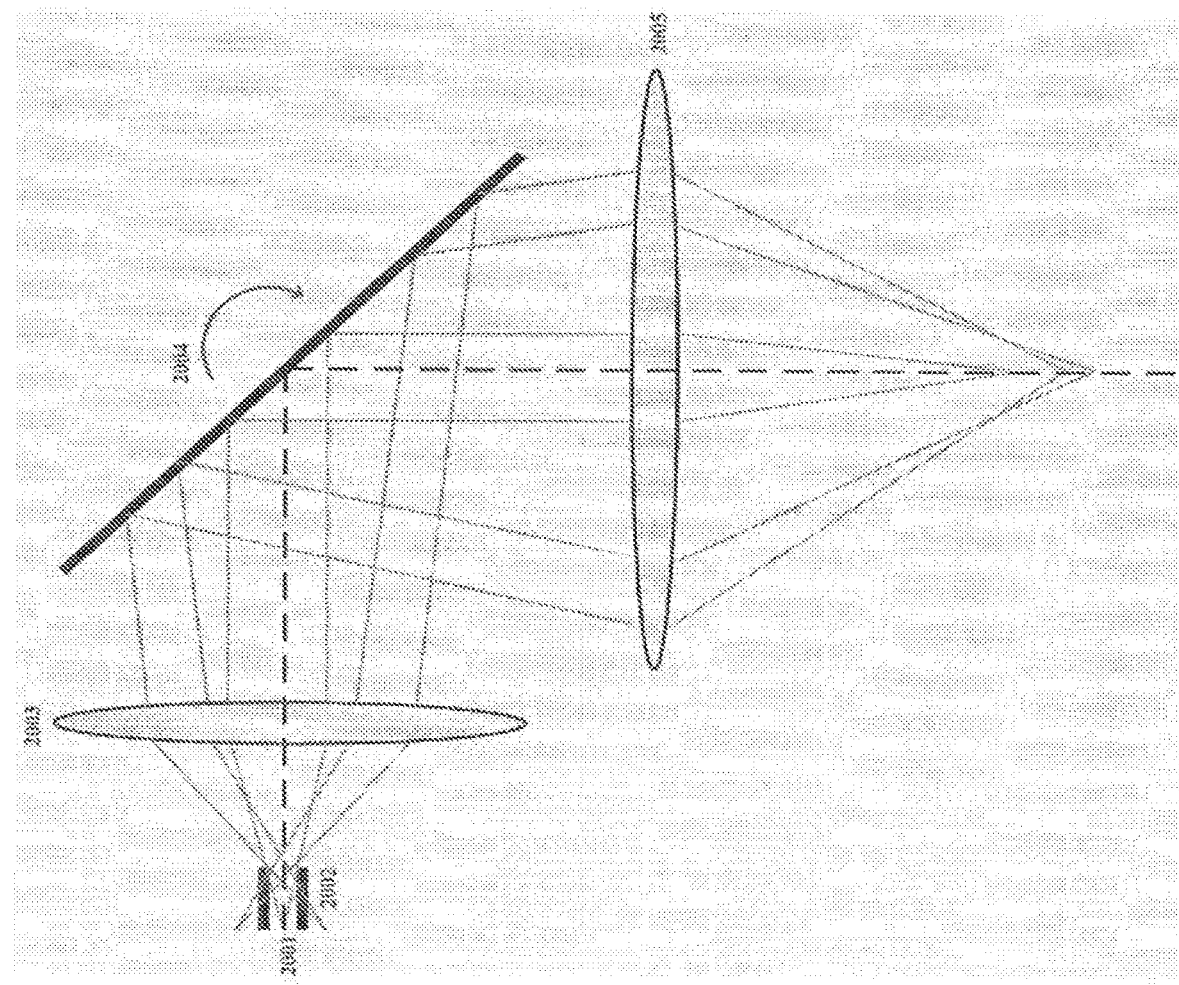
FIG. 20 is a schematic illustration of a mirror tunnel based free space scanning system according to exemplary embodiments of the present disclosure.

FIG. 20 shows an exemplary mirror tunnel based free space scanning system for a benchtop OCT system according to an exemplary embodiment of the present disclosure. The input point source or single mode fiber tip (2001) is placed at the center of mirror tunnel (2002), after a collimator (2003), a 2D or 1D galvanometer system (2004) steers the beam, with objective (2005) focusing, 2D or 1D scanning can be done on the sample. Mirror tunnel helps to extend the depth of focus of this scanning optical system.

Figure 21:
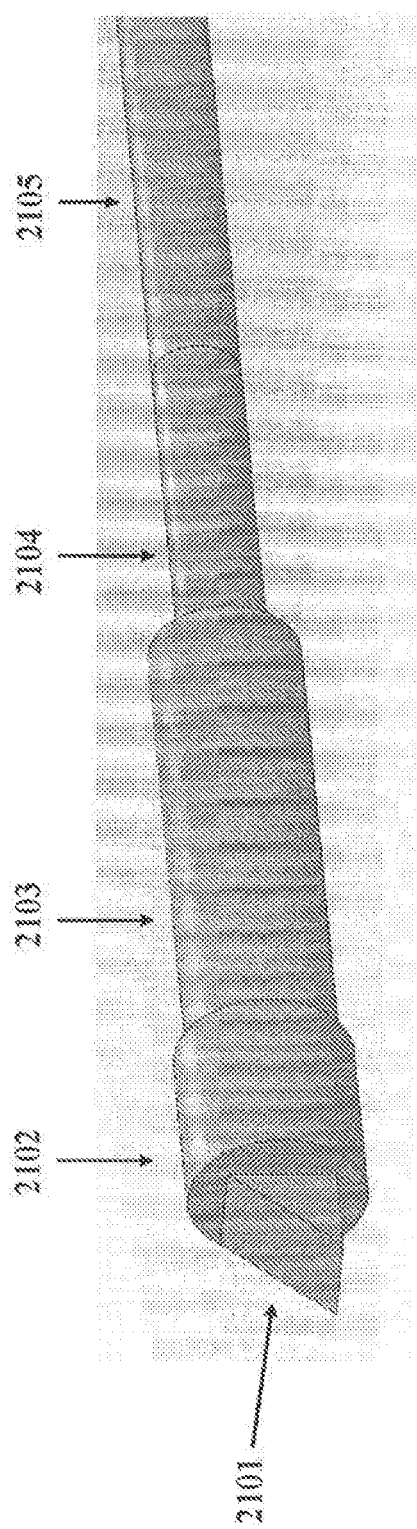
FIG. 21 is a schematic diagram of a side-view of an exemplary self-imaging wavefront division fiber optic probe according to another exemplary embodiment of the present disclosure which can be usable and/or incorporated into any and all other exemplary embodiments described herein.

FIG. 21 shows a schematic diagram of a side-view self-imaging wavefront division fiber optic probe according to another exemplary embodiment of the present disclosure, and can be implemented, incorporated and/or used with the other exemplary embodiments described herein. The exemplary probe shown in FIG. 21 includes, e.g., a right-angle prism (2101), a GRIN lens (2102), a spacer with a length of s (2103), a cylindrical waveguide with a length of L and a core diameter of d (2104) and a single-mode fiber (2105).

Figure 22:
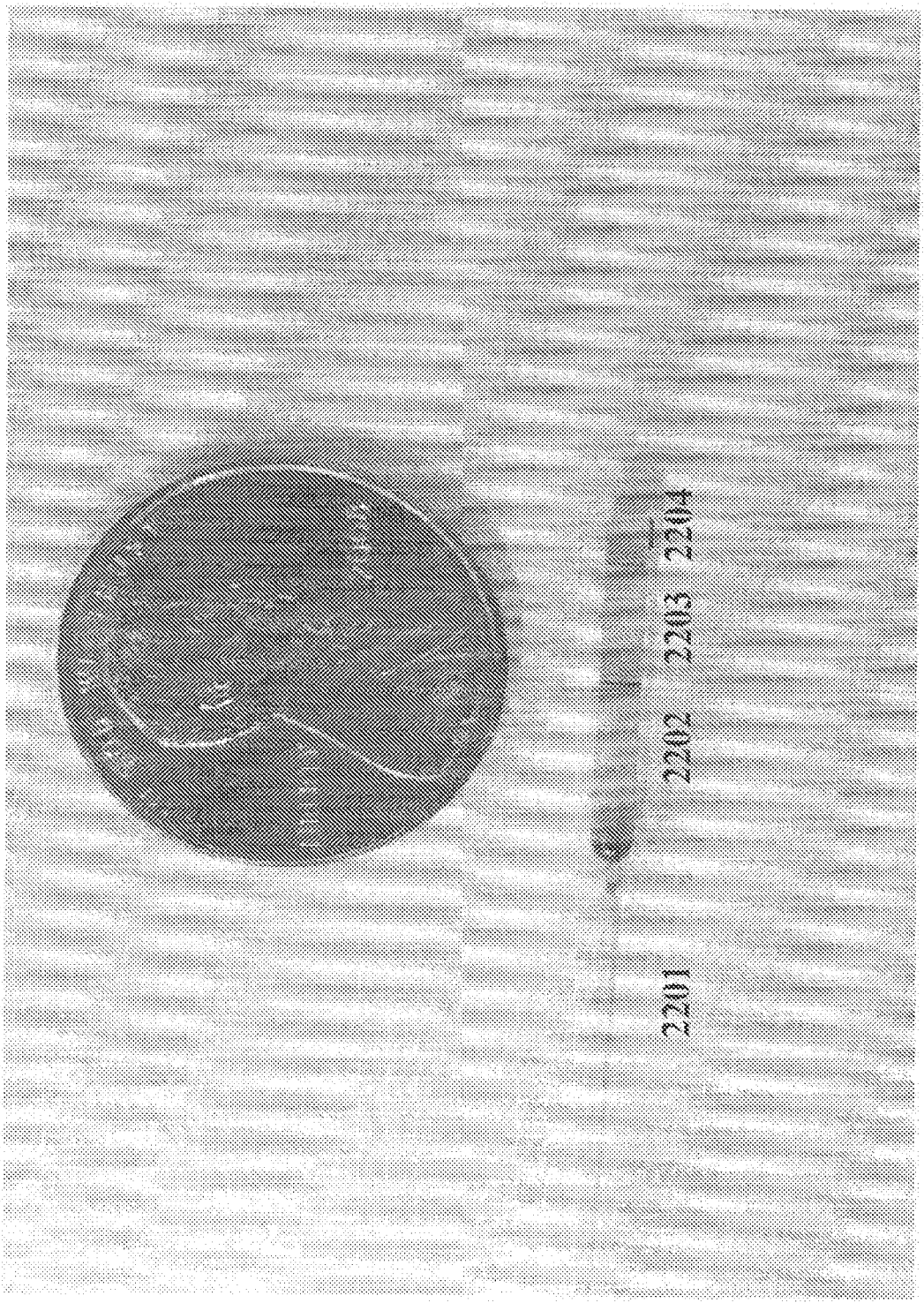
FIG. 22 is a photograph of an exemplary extended DOF fiber probe that provides pseudo-Bessel beams with working distance longer than 6.5 mm for capsule based human gastrointestinal (GI) tract OCT imaging according to another exemplary embodiment of the present disclosure which can be usable and/or incorporated into any and all other exemplary embodiments described herein.

FIG. 22 illustrates an exemplary embodiment of the self-imaging wavefront division optical system for endoscopic imaging. The exemplary system of FIG. 22 includes, e.g., a single-mode fiber (2201) for system light transmission, a multimode fiber (2202) for the generation of multiple propagation modes, a spacer (2203) for beam expansion and a GRIN lens (2204) to focus the beam. This exemplary fiber probe provides a lateral resolution of 8 μm, a DOF of 1 mm at approximately 6.5 mm distance away from distal end surface. The exemplary fiber probe has a diameter of 1.8 mm and a rigid length less than 15 mm, the dimension that is suitable to incorporate into a miniaturized endoscope system.

Figure 23:
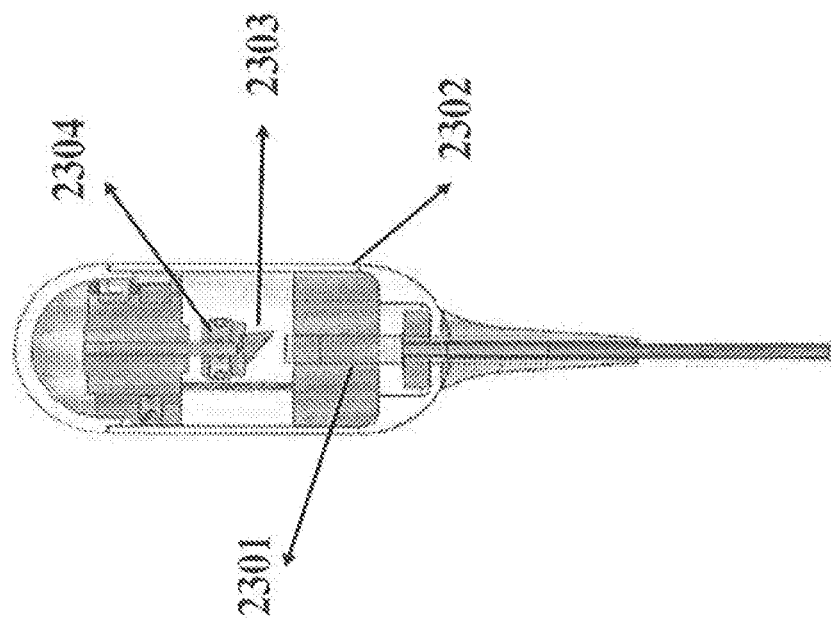
FIG. 23 is a schematic diagram of a swallowable capsule with extended DOF fiber probe and distal end micro-motor incorporated for human GI tract OCT imaging according to another exemplary embodiment of the present disclosure which can be usable and/or incorporated into any and all other exemplary embodiments described herein.

FIG. 23 shows a schematic diagram of a capsule device for GI tract imaging with a self-imaging wavefront division optical system and a distal end micro-motor incorporated, according to another exemplary embodiment of the present disclosure, and can be implemented, incorporated and/or used with the other exemplary embodiments described herein. The fiber probe (2301) is small enough to fit into a capsule device, and a right-angle prism (2303) is attached to a micro-motor (2304) for circumferential scan. The beam is focused outside the capsule wall (2302).

Figure 24A:
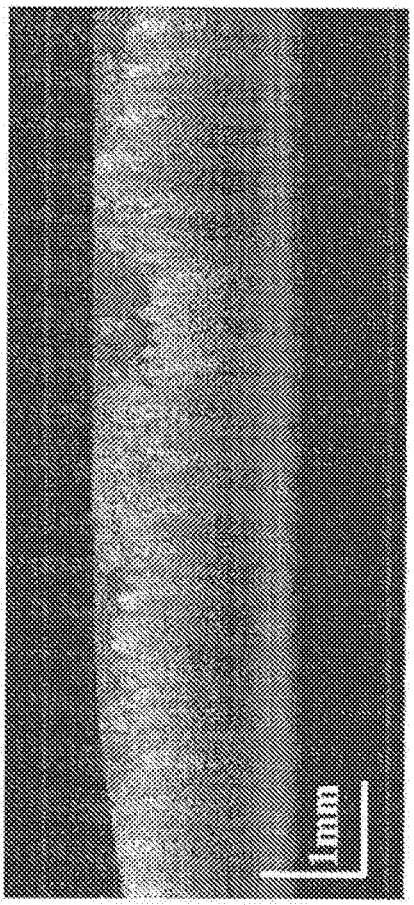
FIGS. 24(a) and 24(b) are illustrations providing a comparison of OCT B-scan images of a fresh swine small intestinal tissue acquired by (a) a Gaussian beam and (b) a pseudo-Bessel beam according to another exemplary embodiment of the present disclosure.
Figure 24B:
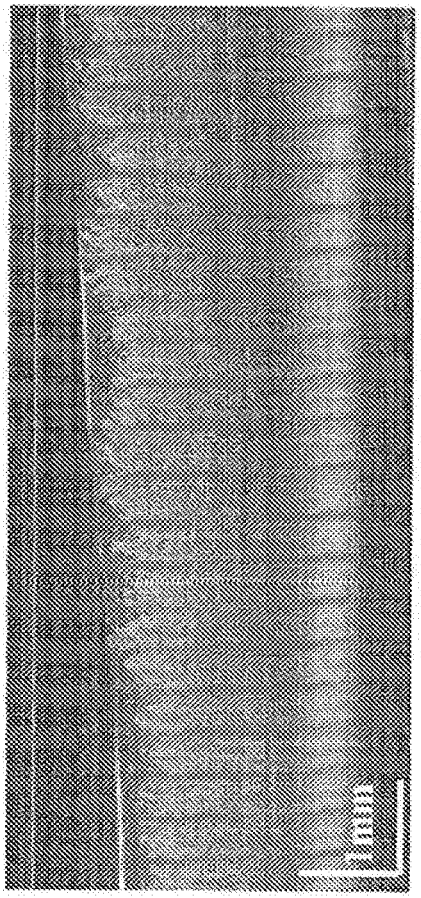

FIG. 24(a) shows an exemplary B-scan image of swine small intestinal tissue acquired by a conventional capsule probe and FIG. 24(b) illustrates the exemplary B-scan image of the same tissue sample acquired by the extended DOF fiber probe shown in FIG. 22. The comparison clearly shows that the pseudo-Bessel beam provides an image with better lateral resolution and longer DOF than Gaussian beam and it is feasible for OCT imaging.

Figure 25:
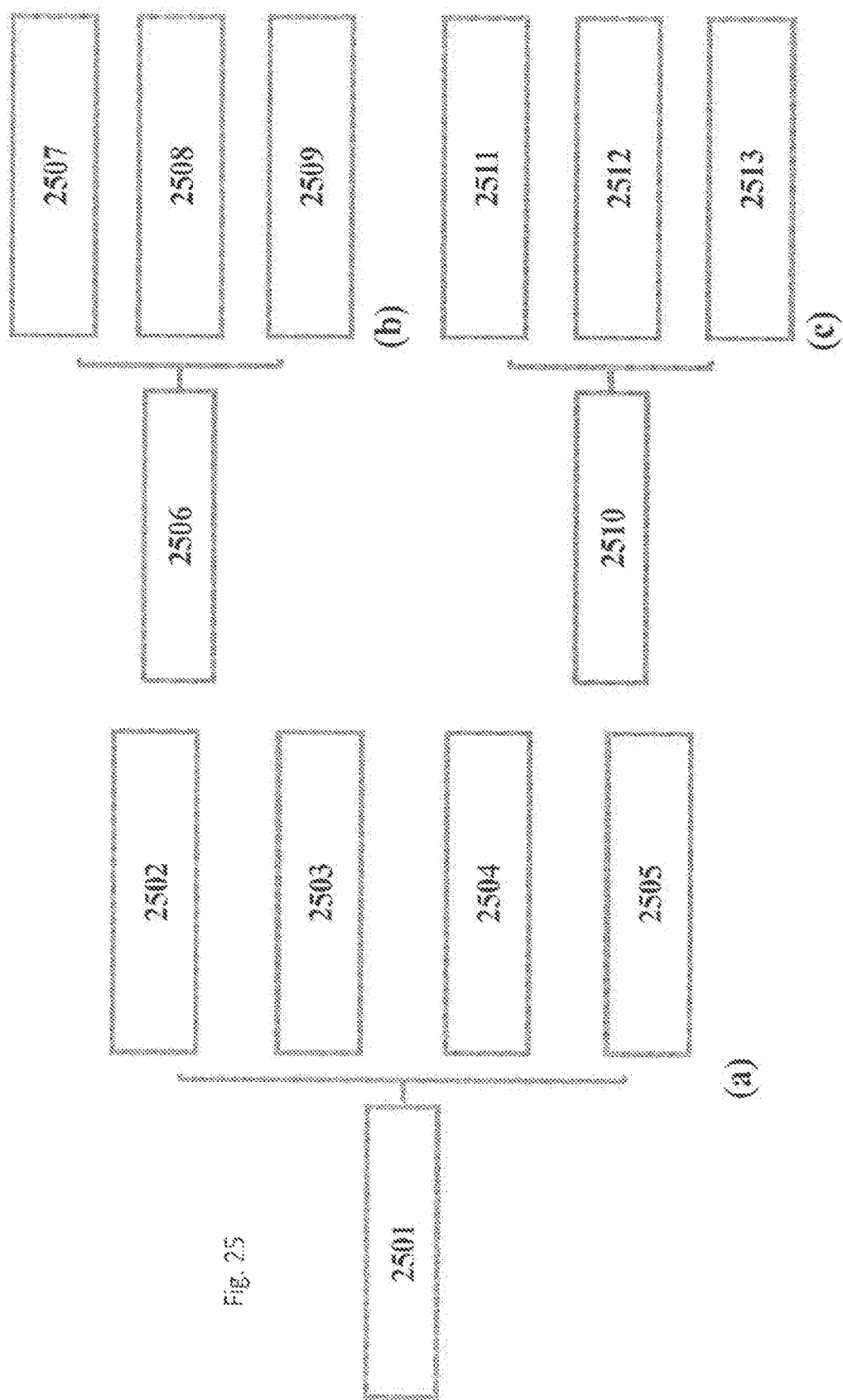
FIGS. 25(a)-25(c) are block diagrams of an exemplary design specifications, variables and system parameters for a typical self-imaging wavefront division optical system.

FIG. 25(a) shows block diagrams for design specifications (2501), FIG. 25(b) shows a block diagram for design variables (2506) and FIG. 25(c) shows a block diagram for system parameters (2510) for a self-imaging wavefront division optical system, according to an exemplary embodiment of the present disclosure. For a typical self-imaging wavefront division optical system, the design specifications include: lateral resolution (2502), DOF (2503), imaging range (2504) and working distance (2505). For example, DOF can be defined as the range within which image resolution is higher than a certain value, while imaging range is defined as the range within which field intensity is above a certain value, and the working distance is defined as the minimal distance from the last surface of the last lens of the probe to the axial position that a clear sample image can be constructed; design variables include: diameter (2507), length of cylindrical waveguide (2508) and length of spacer (2509); and system parameters include: wavelength (2511), single-mode fiber mode field diameter (2512) and refractive indices in object and image space (2513).

Figure 26:
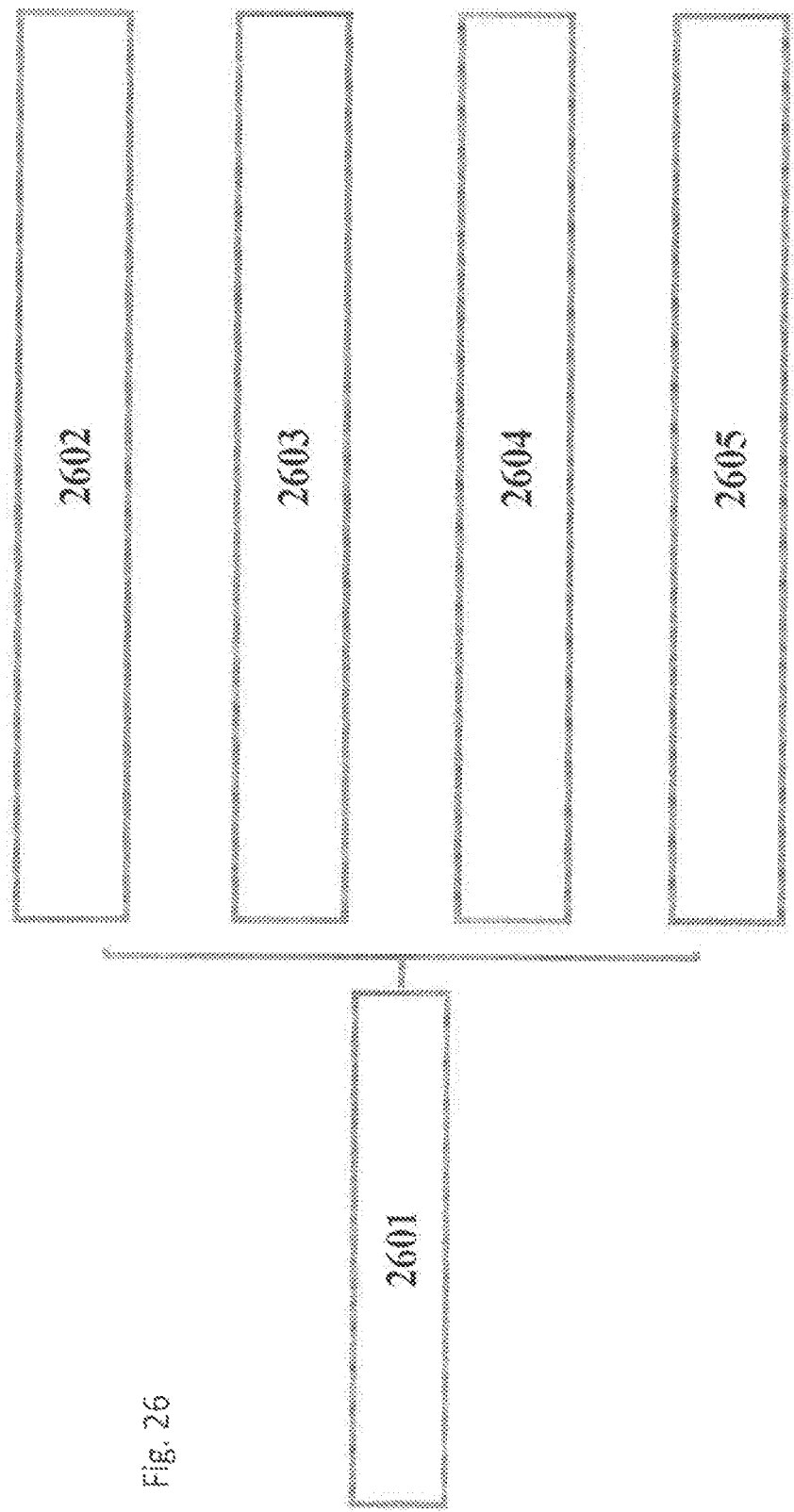
FIG. 26 is a block diagram of exemplary optimization merit function parameter configurations for a typical self-imaging wavefront division optical system.

FIG. 26 shows a block diagram for merit function parameters (2601) of a self-imaging wavefront division optical system according to an exemplary embodiment of the present disclosure. Four parameters can be used to evaluate a self-imaging wavefront division optical system: 1) percentage of the energy in high order modes (2602), which determines the energy efficiency; 2) linear expansion coefficient of the pseudo-Bessel beam (2603), which determines the beam diffraction; 3) size of the focal spot (2604), which determines the lateral resolution of the image; 4) intensity distribution uniformity in axial direction (2605), which relates to the gap width between neighboring modes. For an optimum design, we would like a high energy distribution in high order modes to increase the penetration depth and effective imaging range; a small linear expansion coefficient to reduce the beam diffraction; a small focal spot to improve image resolution; and a uniform intensity distribution to reduce the gap width between modes.

Figure 27:
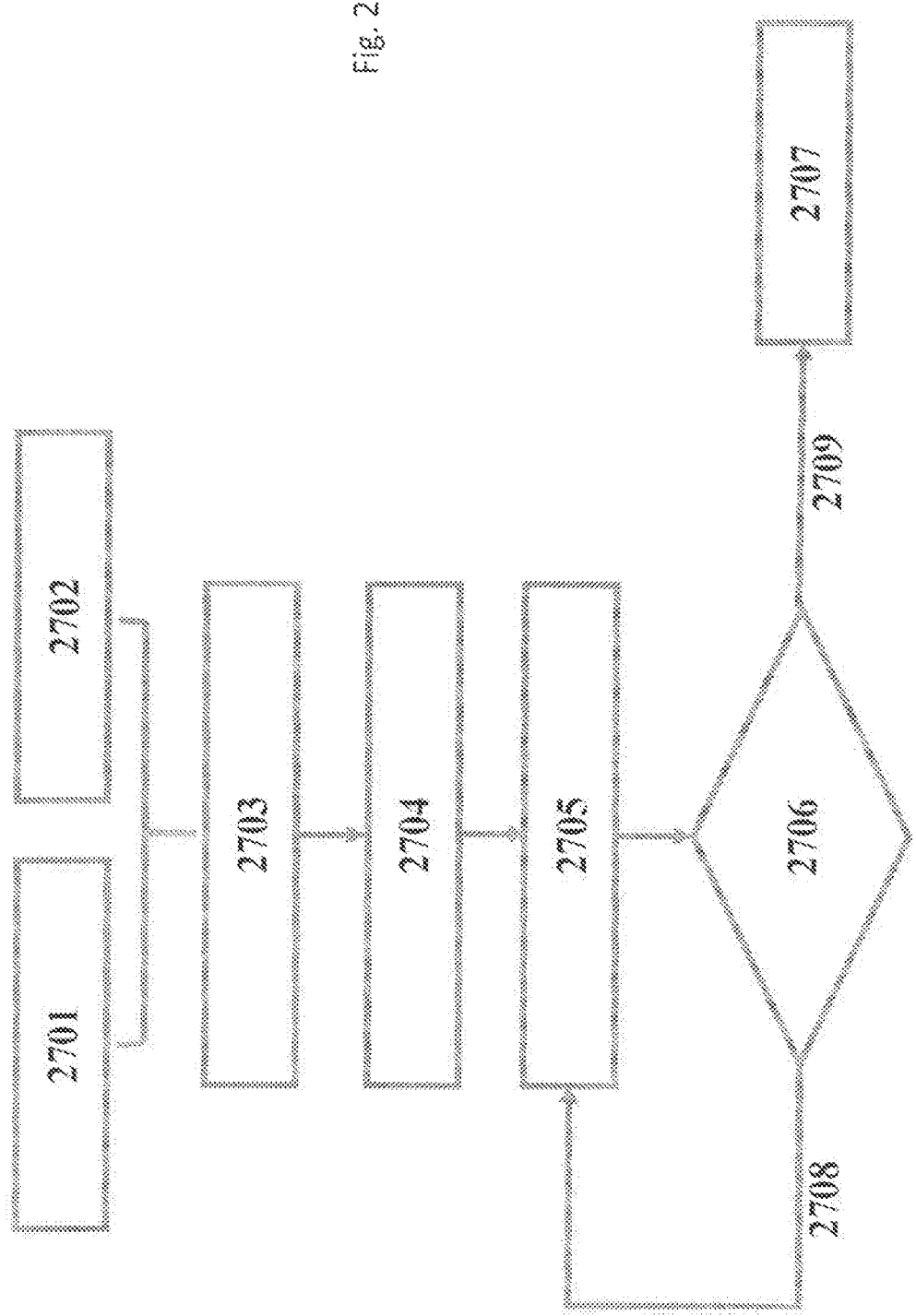
FIG. 27 is a flow diagram for designing a self-imaging wavefront division optical system according to another exemplary embodiment of the present disclosure which can be usable and/or incorporated into any and all other exemplary embodiments described herein.

FIG. 27 shows a flow diagram for a design of a self-imaging wavefront division optical system according to an exemplary embodiment of the present disclosure. The exemplary design process starts with determining the system parameters (2701) and design specifications (2702) according to the application; merit function parameters (2703) can be calculated and weighted differently to generate an overall optimization map (2704); according to the optimization map, several design candidates (2705) can be found; evaluate (2706) the candidate designs in terms of field intensity distribution, point spread function (PSF) and axial intensity profile, if it is not optimum (2708), evaluate the other candidate designs, if it is optimum (2709) the design is finalized (2707).

Figure 28:
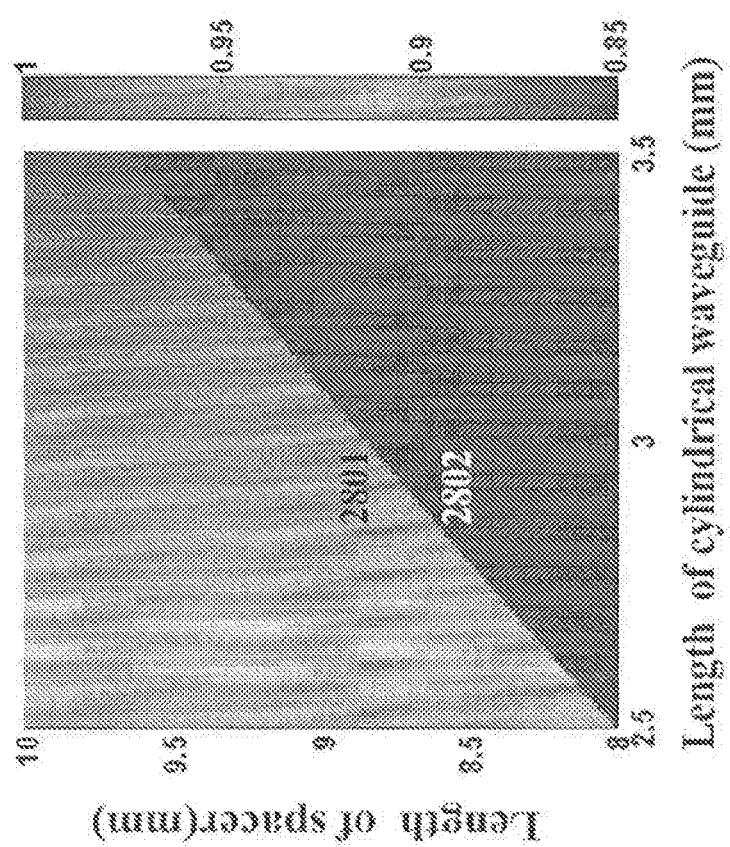
FIG. 28 is a color map showing the percentage of the energy in high order modes normalized by the maximum value in the region of interest with respect to lengths of cylindrical waveguide and spacer for a self-imaging wavefront division optical system with a 100-μm diameter waveguide designed for working distance about 8 mm from the probe distal end. 2801: no loss zone; 2802: loss zone according to another exemplary embodiment of the present disclosure.

FIG. 28 shows an exemplary graph for an exemplary design that uses the color value to represent the percentage of energy contained in high order modes normalized by the maximum value in the region of interest for the design that has cylindrical waveguide length and spacer length corresponding to horizontal and vertical axes respectively. The cylindrical waveguide is with a diameter of 100 µm. In a self-imaging wavefront division optical system, when generating pseudo-Bessel beams, the $0^{th}$ order mode would be generated simultaneously, if the $0^{th}$ order mode is not suitable for imaging, it is necessary to increase the length of cylindrical waveguide to transfer more energy into high order modes. In this graph, zone 2801 is the normal design zone, but zone 2802 is the zone corresponding to the design that has loss due to insufficient system focusing power. Zone 2801 satisfies the relations L≥L+$n_1$f, where s is the length of spacer, L is the length of cylindrical waveguide, $n_1$ is the refractive index in object spacer and f is the focal length of the lens. In zone 2802, portion of the $1^{st}$ order mode pseudo-Bessel beam diverges and is not suitable to use for imaging. One unique property of self-imaging wavefront division optical system is that it splits energy into multiple concentric rings focusing at different depth regions, thus it possesses self-reconstructing property that makes it superior than Gaussian beam when being used to image a scattering-dominant sample.

Figure 29A:
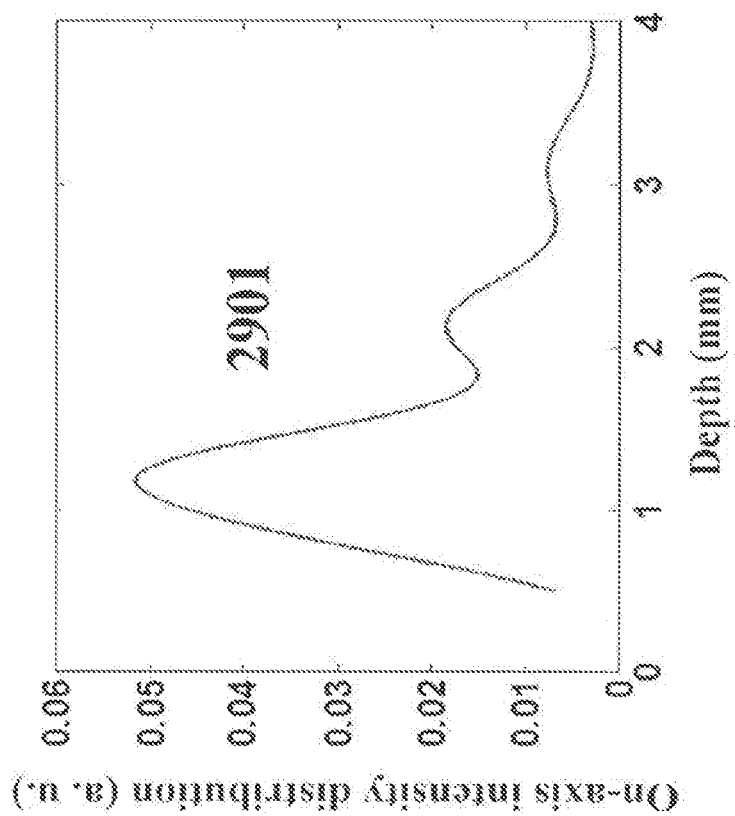
FIGS. 29(a) and 29(b) are graphs providing a comparison of on-axis intensity distribution of the first order mode pseudo-Bessel beam for designs in FIG. 29(a) with a no-loss zone (2901) and in FIG. 29(b) with a loss zone (2902) in response to 2801 and 2802 shown in FIG. 28.
Figure 29B:
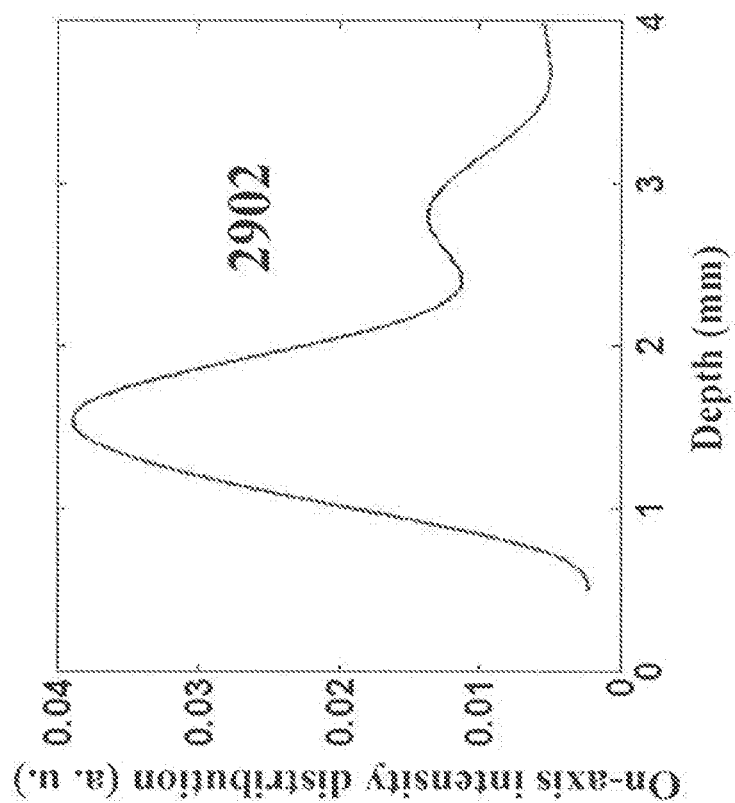

FIGS. 29(a) and 29(b) show exemplary graphs providing a comparison of the on-axis intensity distributions of the $1^{st}$ order mode pseudo-Bessel beam designed in (a) zone 2801 and (b) zone 2802 in FIG. 28, where we observe a relatively higher residual intensity at a distance of 2 mm from the intensity peak shown in FIG. 29(b) compared to the intensity peak shown in FIG. 29(a). The portion of the energy that leaks into the deeper region doesn't contribute to imaging but may interfere with higher order modes. Therefore, we want to avoid designs in zone 2802.

Figure 30:
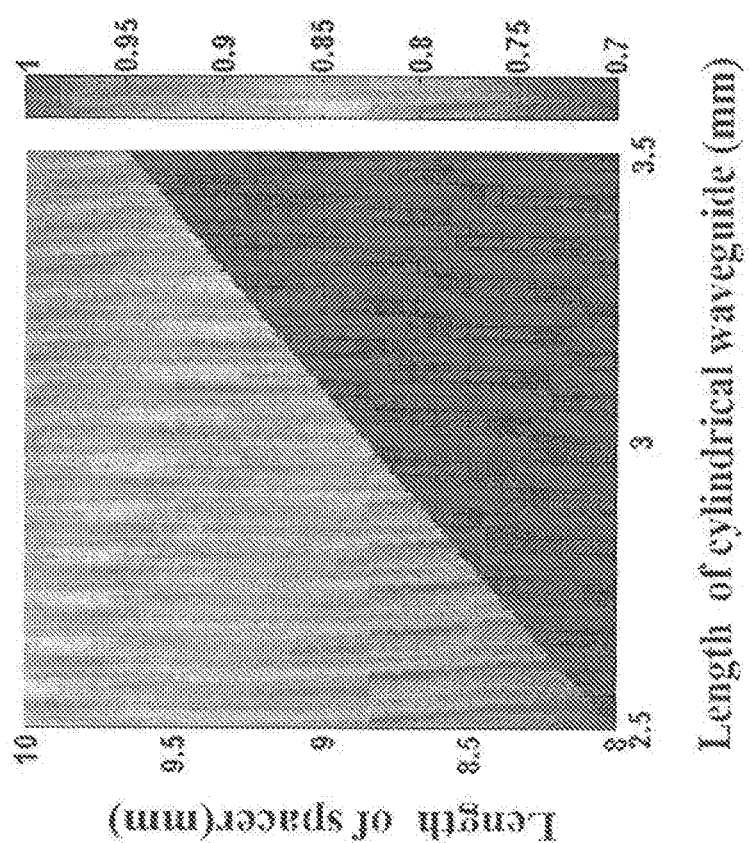
FIG. 30 is a color map of the inverse of the linear expansion coefficient of the first-order mode pseudo-Bessel beam normalized by the maximum value in the region of interest with respect to the lengths of cylindrical waveguide and spacer for a self-imaging wavefront division optical system using a 100-μm diameter waveguide designed for working distance about 8 mm from the probe distal end, according to another exemplary embodiment of the present disclosure.

FIG. 30 shows an exemplary graph for an exemplary design that uses the color value to represent the inverse of linear expansion coefficient normalized by the maximum value in the region of interest for the design that has cylindrical waveguide length and spacer length corresponding to horizontal and vertical axes respectively. The cylindrical waveguide is with a diameter of 100 µm. With a common cylindrical waveguide diameter, linear expansion coefficient increases with increasing the total length of cylindrical waveguide and spacer. The linear expansion coefficient is approximately proportional to (L+s)/md where L and s are defined as before, m is the order of mode and d is the diameter of the cylindrical waveguide.

Figure 31B:
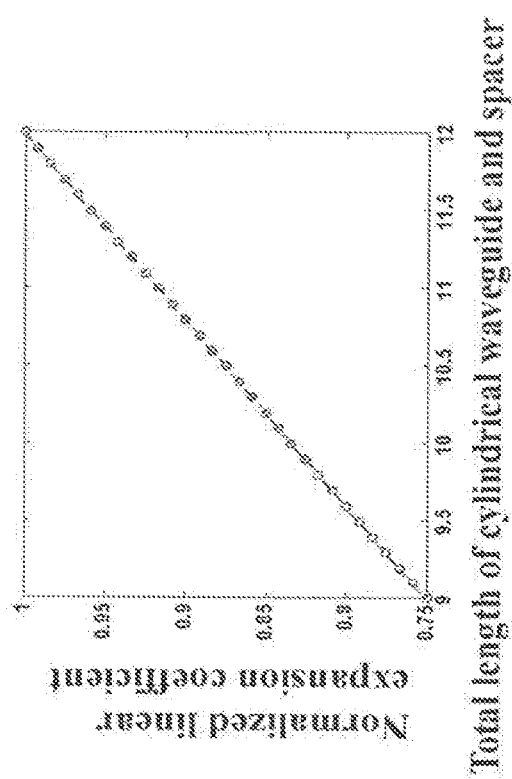
FIGS. 31(a)-31(c) are graphs describing the dependence of linear expansion coefficient on order of modes (FIG. 31(a)); total length of cylindrical waveguide and spacer (FIG. 31(b)); and a diameter of cylindrical waveguide (FIG. 31(c)), with the linear expansion coefficient being normalized by the maximum value in the region of interest, according to another exemplary embodiment of the present disclosure.
Figure 31A:
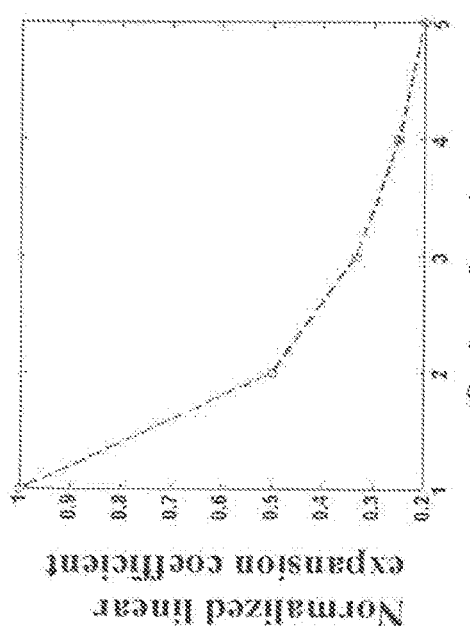
Figure 31C:
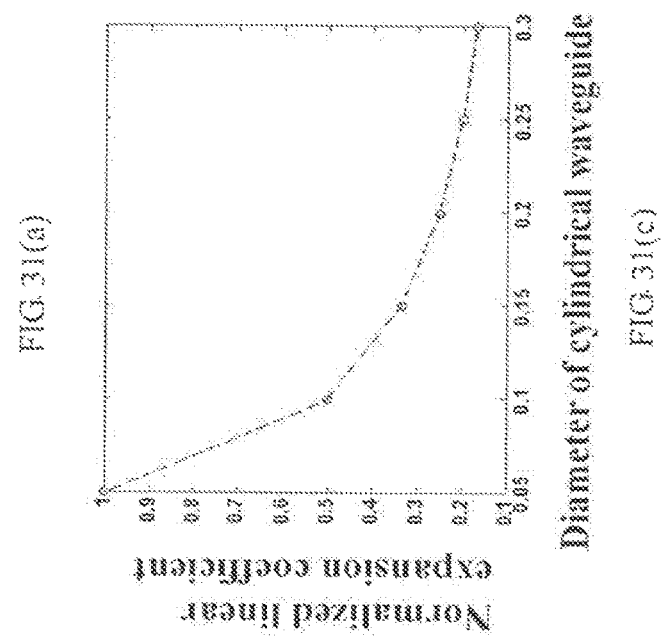

FIGS. 31(a)-31(c) show exemplary graphs indicating the dependence of linear expansion coefficient on order of mode (FIG. 31(a)), total length of cylindrical waveguide and spacer (FIG. 31(b)), and a diameter of cylindrical waveguide (FIG. 31(c)). Linear expansion coefficient decreases with increasing the order of modes, or reducing the total length of cylindrical waveguide and spacer, or increasing the diameter of cylindrical waveguide. Linear expansion coefficient is preferred to be minimized to reduce the beam diffraction.

Figure 32:
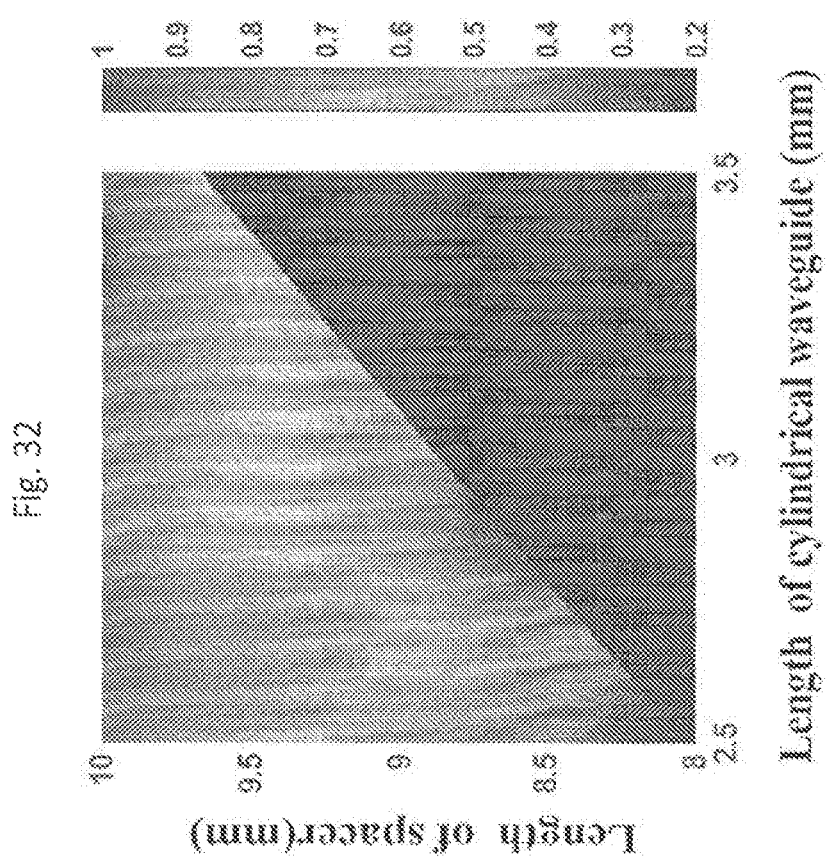
FIG. 32 is a color map of the overall on-axis intensity for high order modes normalized by the maximum value in the region of interest with respect to the lengths of cylindrical waveguide and spacer for a self-imaging wavefront division optical system using a 100-μm diameter waveguide designed for working distance about 8 mm from the probe distal end, according to another exemplary embodiment of the present disclosure.

FIG. 32 shows an exemplary graph for an exemplary design that uses the color value to represent the estimated overall on-axis intensity normalized by the maximum value in the region of interest for the design that has cylindrical waveguide length and spacer length corresponding to horizontal and vertical axes respectively. The cylindrical waveguide is with a diameter of 100 µm. Overall on-axis intensity is estimated as the total intensity on the optical axis of the beam, therefore, higher value corresponds to a design with higher lateral resolution as energy is more concentrated in the center of the beam. The lateral resolution increases by increasing spacer length.

Figure 33A:
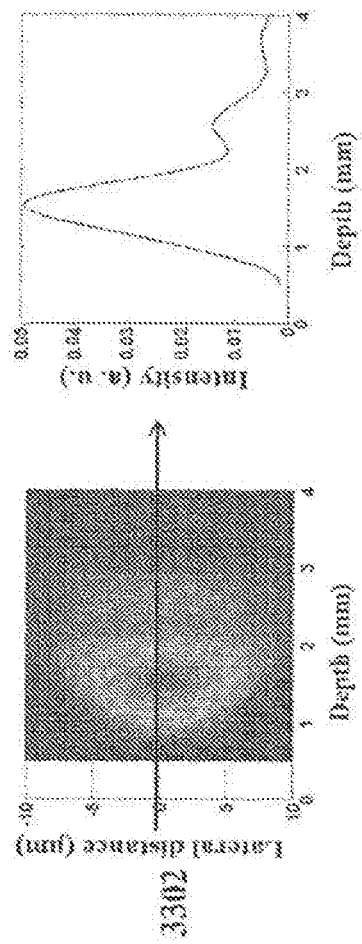
FIG. 33(a) is a plot showing the spot size vs. distance in image space for different modes in a self-image wavefront division optical system using a cylindrical waveguide with a diameter of 100 μm, a length of 3.2 mm and a spacer with a length of 9.9 mm designed for working distance about 8 mm from the probe distal end, according to another exemplary embodiment of the present disclosure.
Figure 33B:
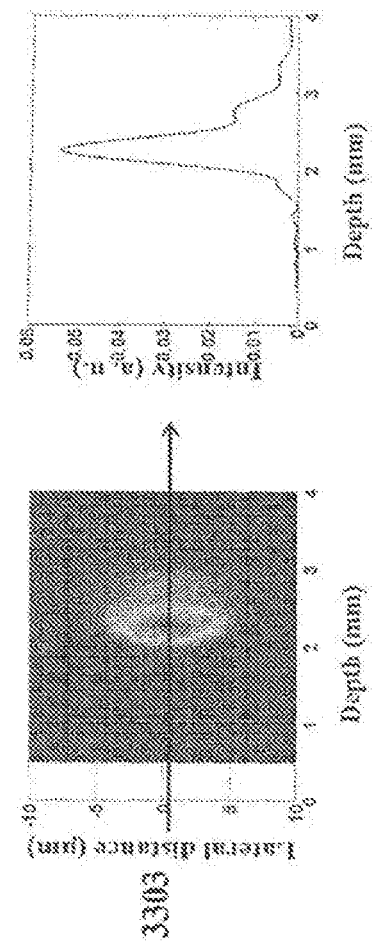
FIG. 33(b) is a graph and intensity map of a field intensity distribution for the $1^{st}$ order mode.
Figure 33C:
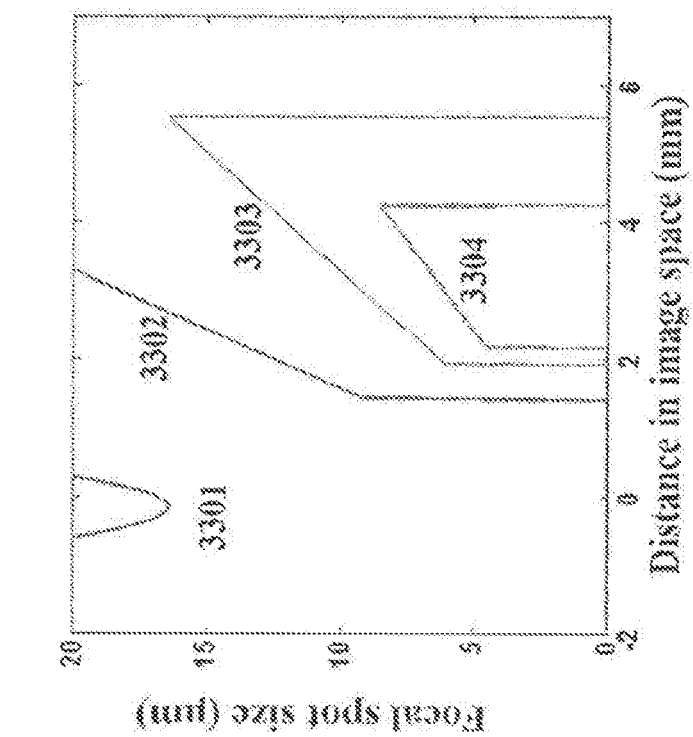
FIG. 33(c) is a graph and intensity map of field intensity distribution for the $2^{nd}$ order mode, according to another exemplary embodiment of the present disclosure.

FIG. 33(a) shows an exemplary plot for an exemplary design showing spot size vs. distance for the $0^{th}$ order mode (3301), the $1^{st}$ order mode (3302), the $2^{nd}$ order mode (3303), and the $3^{rd}$ order mode (3304) according to an exemplary embodiment of the present disclosure. FIG. 33(b) shows an exemplary field intensity distribution for the $1^{st}$ order mode according to an exemplary embodiment of the present disclosure. FIG. 33(c) shows an exemplary field intensity distribution for the $2^{nd}$ order mode according to an exemplary embodiment of the present disclosure. For example, with a proper design, the pseudo-Bessel beams exhibit higher lateral resolution and longer DOF than the $0^{th}$ order mode beam. Among pseudo-Bessel beams, the $1^{st}$ order mode has the largest focal spot and linear expansion coefficient but longest axial focusing region. Each mode's focusing region can be contained within the focusing regions of the lower order modes. The focusing region for mode order m is mathematically described as $$\left( \frac{n_2 f(2ms + L + s)}{(2ms + L + s) - 2n_1 mf - n_1 f}, \frac{n_2 f(2ms - L - s)}{(2ms - L - s) - 2n_1 mf + n_1 f} \right)$$

where $n_2$ is the refractive index in image space and other parameters are defined same as before. The intensity peak of each high order mode is located at the proximal end of its focusing region as shown in FIGS. 33(b) and 33(c), thus, the total effective imaging region of the optical system consists of focusing regions of modes separated in axial direction with minimal overlaps.

Figure 34:
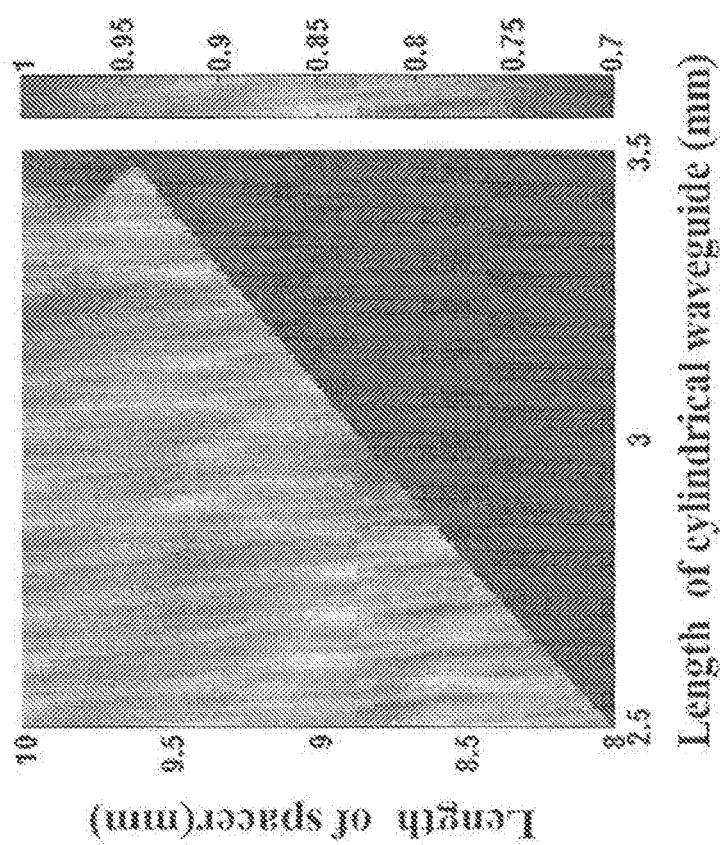
FIG. 34 is a color map of the percentage of the depth range that has on-axis intensity higher than 10% of the peak on-axis intensity normalized by the maximum value in the region of interest with respect to the lengths of cylindrical waveguide and spacer for a self-imaging wavefront division optical system using a 100-μm diameter waveguide designed for working distance about 8 mm from the probe distal end, according to another exemplary embodiment of the present disclosure.

FIG. 34 shows an exemplary graph for an exemplary design that uses the color value to represent the percentage of the depth range that has on-axis intensity higher than 10% of the peak intensity normalized by the maximum value in the region of interest for the design that has cylindrical waveguide length and spacer length corresponding to horizontal and vertical axes respectively. The cylindrical waveguide is with a diameter of 100 µm. This value indicates the intensity distribution uniformity in axial direction of the pseudo-Bessel beams. Higher value is preferred as it corresponds to a design that has smaller gap width that mitigates the image discontinuity in axial direction.

Figure 35:
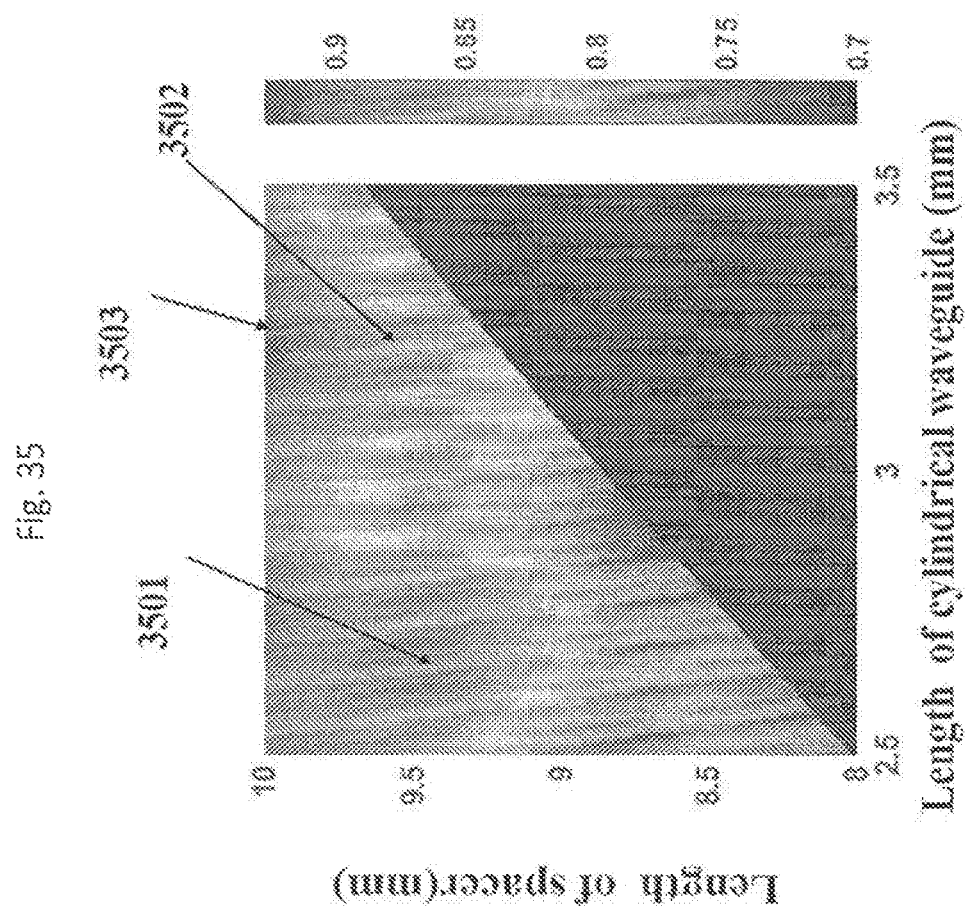
FIG. 35 is a color map of the sum of the four merit function parameters with equal weight normalized by the maximum value in the region of interest with respect to the lengths of cylindrical waveguide and spacer for an exemplary self-imaging wavefront division optical system using a 100-μm diameter waveguide designed for working distance about 8 mm from the probe distal end, according to another exemplary embodiment of the present disclosure.

FIG. 35 shows an exemplary graph for an exemplary design that uses the color value to represent the sum of four merit function parameters with equal weights normalized by the maximum value in the region of interest that has cylindrical waveguide length and spacer length corresponding to horizontal and vertical axes respectively. Merit function parameters can be weighted differently to optimize the design toward specific application. Three candidate designs are located at: (2.690, 9.495) mm (3501); (3.225, 9.495) mm (3502); and (3.215, 10.000) mm (3503), which can be considered as the potential optimum designs suitable for further evaluation.

Figure 36:
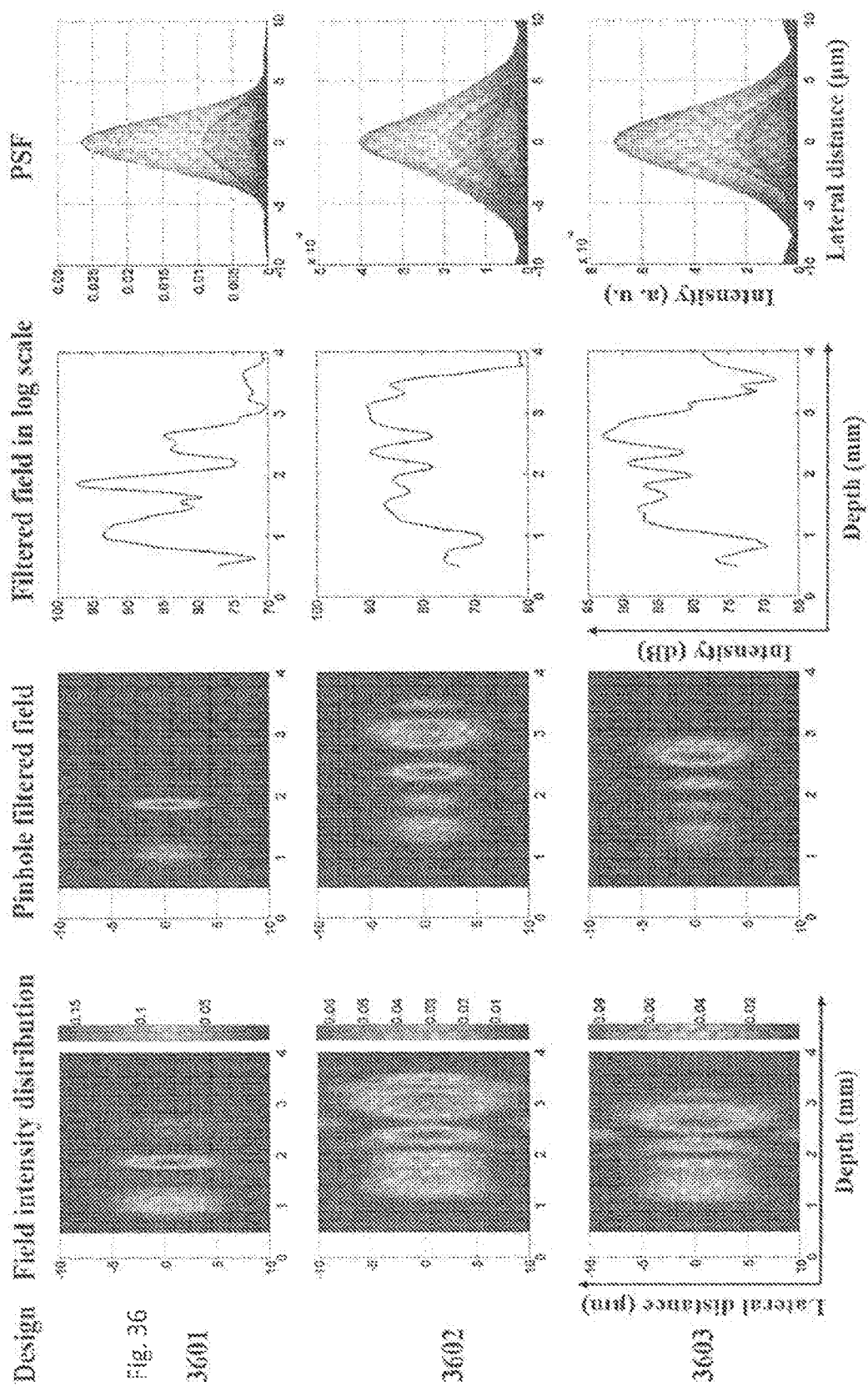
FIG. 36 is a set of intensity profiles and graphs providing a comparison of the three candidate designs shown in FIG. 35 in terms of field intensity distribution, pinhole filtered field intensity distribution, on-axis pinhole filtered field intensity in log scale, and PSFs of different modes, according to another exemplary embodiment of the present disclosure.

FIG. 36 shows illustrations to provide a comparison of the three candidate designs in FIG. 35 with cylindrical waveguide and spacer lengths as (2.690, 9.495) mm (3601), (3.225, 9.495) mm (3602), and (3.215, 10.000) mm (3603) according to an exemplary embodiment of the present disclosure. The field intensity distribution without and with pinhole filtering in linear scale, on-axis pinhole filtered field intensity in log scale, and PSFs of different modes are presented. The exemplary optimum design according to an exemplary embodiment of the present disclosure can be determined according to, e.g., resolution, imaging range, intensity gaps and/or fabrication feasibility.

Figure 37:
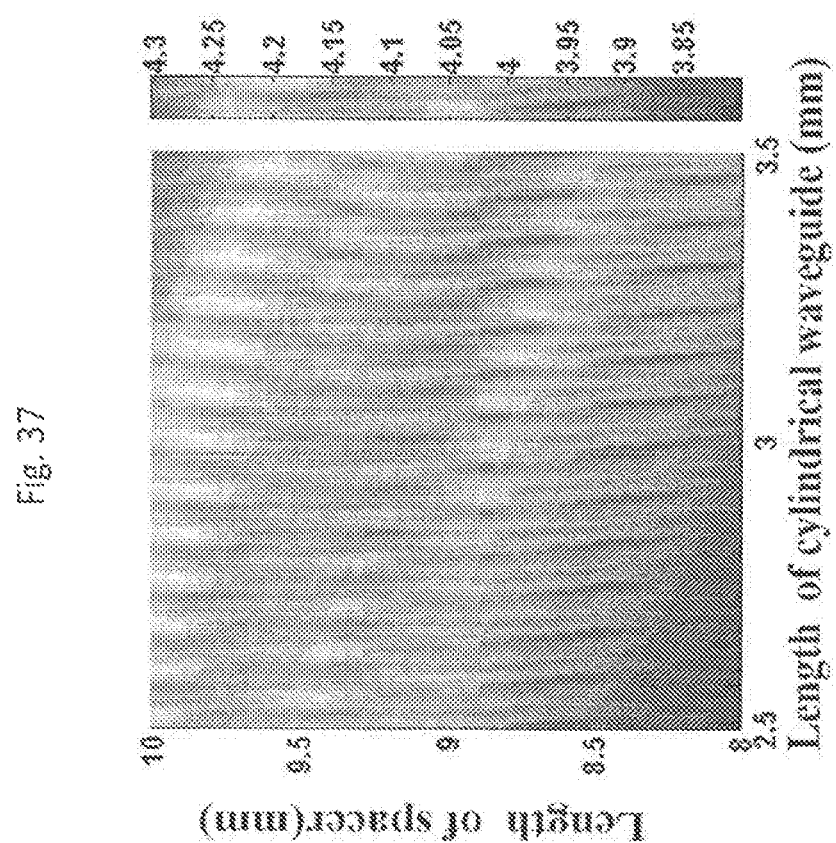
FIG. 37 is a color map of focal length of the lens with respect to the lengths of cylindrical waveguide and spacer for a self-imaging wavefront division optical system using a 100-μm diameter waveguide designed for working distance about 8 mm from the probe distal end, according to another exemplary embodiment of the present disclosure.
Figure 42A:
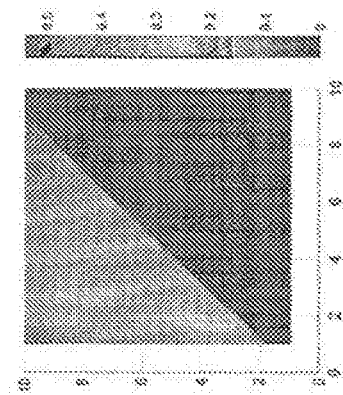
FIGS. 42(a)-42(f) are illustrations of the exemplary optimal design parameter ranges for the exemplary catheter and needle probes with imaging range 0.5-2.5 mm, rigid length less than 20 mm and aperture diameter less than 1 mm operated at wavelength 1300 nm, according to another exemplary embodiment of the present disclosure which can be implemented with any one of the exemplary embodiments of the present disclosure described herein.
Figure 42B:
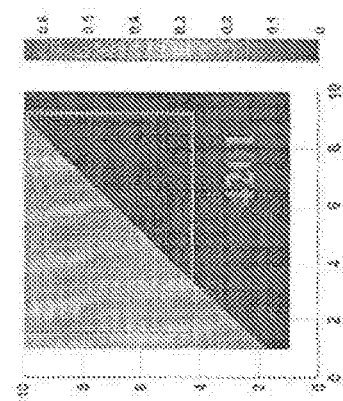
Figure 42C:
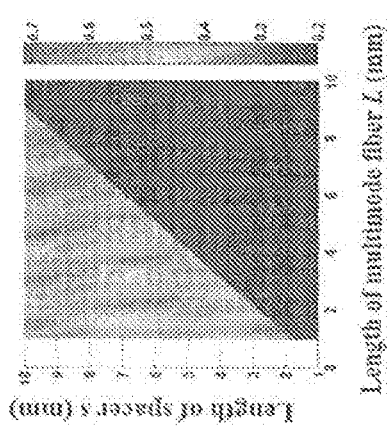
Figure 42D:
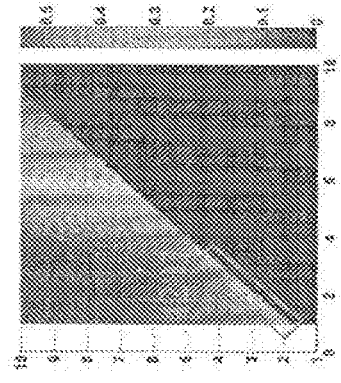
Figure 42E:
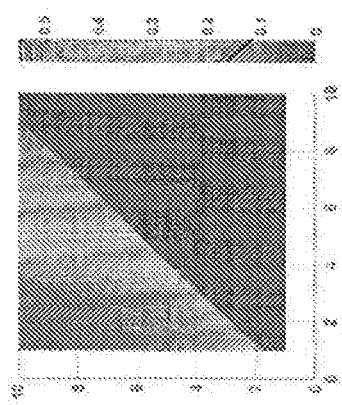
Figure 42F:
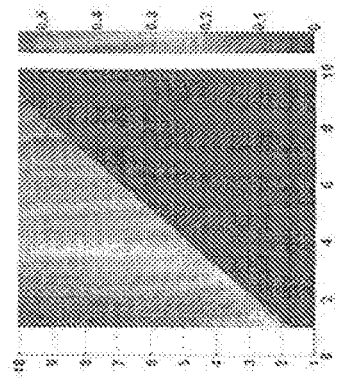
Figure 43D:
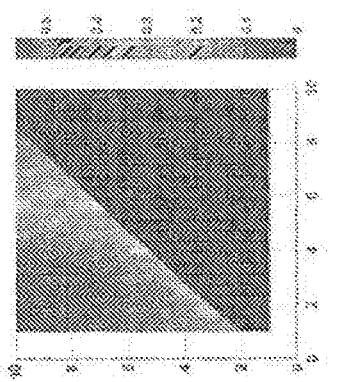
FIGS. 43(a)-43(g) are illustrations of the exemplary optimal design parameter ranges for the exemplary endoscope probes with imaging range 1-3 mm, rigid length less than 20 mm and aperture diameter less than 3 mm operated at wavelength 800 nm, according to another exemplary embodiment of the present disclosure which can be implemented with any one of the exemplary embodiments of the present disclosure described herein.
Figure 43C:
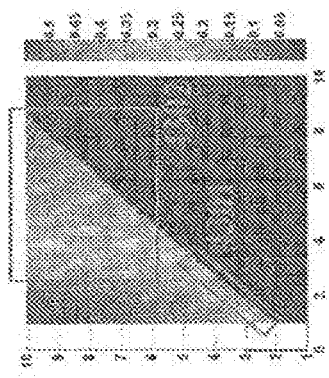
Figure 43G:
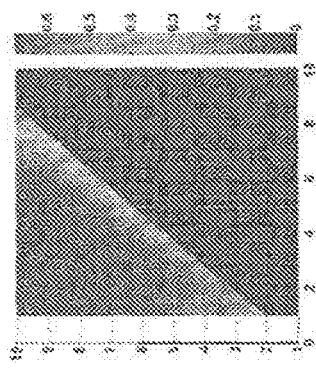
Figure 43B:
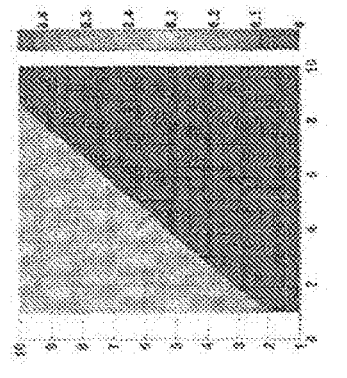
Figure 43F:
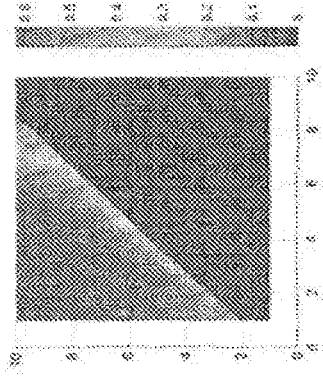
Figure 43A:
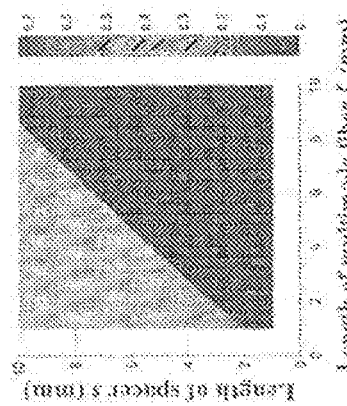
Figure 43E:
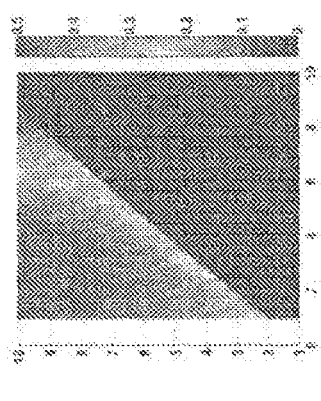
Figure 44A:
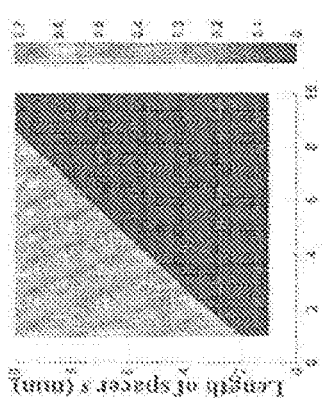
FIGS. 44(a)-44(g) are illustrations of the exemplary optimal design parameter ranges for the exemplary endoscope probes with imaging range 1-3 mm, rigid length less than 20 mm and aperture diameter less than 3 mm operated at wavelength 1300 nm, according to another exemplary embodiment of the present disclosure which can be implemented with any one of the exemplary embodiments of the present disclosure described herein.
Figure 44B:
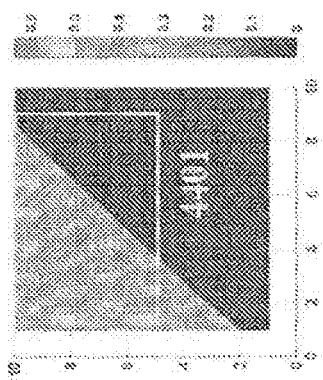
Figure 44C:
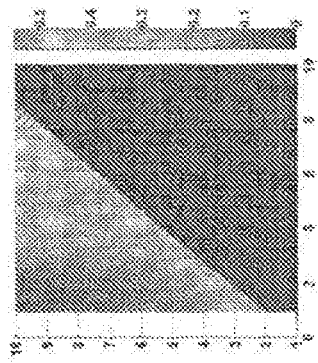
Figure 44D:
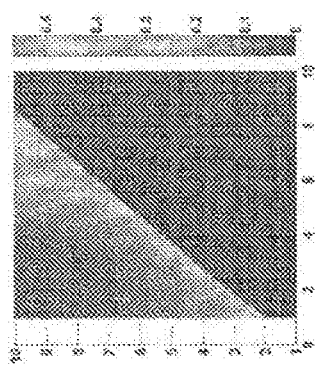
Figure 44E:
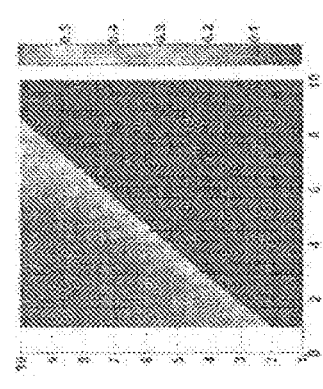
Figure 44F:
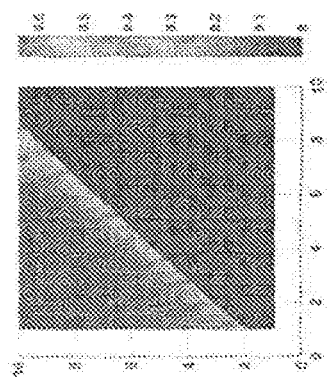
Figure 44G:
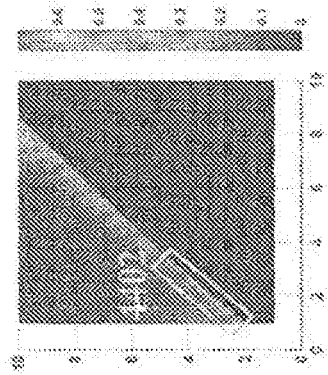

FIG. 37 shows an exemplary graph for an exemplary design that uses the color value to represent the approximate focal length of the lens for the design that has cylindrical waveguide length and spacer length corresponding to horizontal and vertical axes respectively. The cylindrical waveguide is with a diameter of 100 μm. The focal length of the lens is determined according to the required working distance (8 mm for this particular design), and it depends on the total length of the cylindrical waveguide and the spacer. When $0^{th}$ order mode is being used, the focal length f can be estimated according to lens law:

$$\frac{n_1}{L+s} - \frac{1}{f} + \frac{n_2}{WD} = 0$$

where WD refers to working distance.

FIGS. 38(*a*)-38(*f*) show illustrations of exemplary optimal design parameter ranges for probes with imaging range 0.5-2.5 mm, rigid length less than 10 mm and aperture diameter less than 0.2 mm operated at wavelength 800 nm and 1300 nm respectively, according to an exemplary embodiment of the present disclosure. The top row includes optimization color maps for designs operated at 800 nm wavelength using multimode fiber with diameters of (a) 50 μm, (b) 100 μm and (c) 150 μm; the bottom row includes optimization color maps for designs operated at 1300 nm wavelength using multimode fiber with diameters of (d) 50 μm (e) 100 μm and (f) 150 μm. Define L and s as the optical pathlength of multimode fiber and spacer. 3801: optimal design region for 800 nm wavelength, described as L≤s≤L+6 mm, 0.8 mm≤L≤5 mm; 3802: optimal design region for 1300 nm wavelength, described as L≤s≤L+6 mm, 0.8 mm≤L≤5 mm.

FIGS. 39(*a*)-39(*e*) show illustrations of the exemplary optimal design parameter ranges for probes with imaging range 0.5-2.5 mm, rigid length less than 10 mm and aperture diameter less than 0.5 mm operated at wavelength 800 nm, according to an exemplary embodiment of the present disclosure. Optimization color maps for designs operated at 800 nm wavelength using multimode fiber with diameters of (a) 50 μm, (b) 100 μm, (c) 200 μm, (d) 300 μm and (e) 400 μm are presented—3901; exemplary optimal design region 1, described as 0.8 mm≤L≤3 mm, 1.5 mm≤s≤8 mm; 3902: and exemplary optimal design region 2, described as 2.5 mm≤L≤4.5 mm, 3 mm≤s≤7 mm.

FIGS. 40(*a*)-40(*e*) show illustrations of the exemplary optimal design parameter ranges for probes with imaging range 0.5-2.5 mm, rigid length less than 10 mm and aperture diameter less than 0.5 mm operated at wavelength 1300 nm, according to an exemplary embodiment of the present disclosure. Optimization color maps for designs operated at 1300 nm wavelength using multimode fiber with diameters of (a) 50 μm, (b) 100 μm, (c) 200 μm, (d) 300 μm and (e) 400 μm are presented—4001: exemplary optimal design region 1, described as 0.8 mm≤L≤2 mm, 1.8 mm≤s≤6 mm; and 4002: exemplary optimal design region 2, described as 2 mm≤L≤4.5 mm, 2 mm≤s≤8.5 mm.

FIGS. 41(*a*)-41(*f*) show illustrations of the exemplary optimal design parameter ranges for catheter and needle probes with imaging range 0.5-2.5 mm, rigid length less than 20 mm and aperture diameter less than 1 mm operated at wavelength 800 nm, according to an exemplary embodiment of the present disclosure. Optimization color maps for designs operated at 800 nm wavelength using multimode fiber with diameters of (a) 50 μm, (b) 100 (c) 200 μm, (d) 400 μm, (e) 600 μm and (f) 800 μm are presented—4101: exemplary optimal design region 1, described as 2 mm≤L≤9 mm, 4 mm≤s≤10 mm; and 4102: exemplary optimal design region 2, described as L≤s≤L+1.5 mm, 1 mm≤L≤4 mm.

FIGS. 42(*a*)-42(*f*) show illustrations of the exemplary optimal design parameter ranges for catheter and needle probes with imaging range 0.5-2.5 mm, rigid length less than 20 mm and aperture diameter less than 1 mm operated at wavelength 1300 nm, according to an exemplary embodiment of the present disclosure. Optimization color maps for designs operated at 1300 nm wavelength using multimode fiber with diameters of (a) 50 μm, (b) 100 μm, (c) 200 μm, (d) 400 μm, (e) 600 μm and (f) 800 μm are presented—4201: optimal design region 1, described as 1.8 mm≤L≤9.5 mm, 4 mm≤s≤10 mm; and 4202: exemplary optimal design region 2, described as L≤s≤L+1.5 mm, 1 mm≤L≤4 mm.

FIGS. 43(*a*)-43(*g*) show illustrations of the exemplary design parameter ranges for endoscope probes with imaging range 1-3 mm, rigid length less than 20 mm and aperture diameter less than 3 mm operated at wavelength 800 nm, according to an exemplary embodiment of the present disclosure. Optimization color maps for designs operated at 800 nm wavelength using multimode fiber with diameters of (a) 50 μm, (b) 100 μm, (c) 500 μm, (d) 1000 μm, (e) 1500 μm, (f) 2000 μm and (g) 2500 μm are presented—4301: exemplary optimal design region 1, described as L+0.4 mm≤s≤L+1.5 mm, 1 mm≤L≤4 mm; and 4302: exemplary optimal design region 2, described as 2 mm≤L≤9 mm, 5.5 mm≤s≤10 mm.

FIGS. 44(*a*)-44(*g*) show illustrations of the exemplary design parameter ranges for endoscope probes with imaging range 1-3 mm, rigid length less than 20 mm and aperture diameter less than 3 mm operated at wavelength 1300 nm, according to an exemplary embodiment of the present disclosure. Optimization color maps for designs operated at 1300 nm wavelength using multimode fiber with diameters of (a) 50 μm, (b) 100 μm, (c) 500 μm, (d) 1000 μm, (e) 1500 μm, (f) 2000 μm and (g) 2500 μm are presented—4401: exemplary optimal design region 1, described as 1.8 mm≤L≤9 mm, 4.5 mm≤s≤10 mm; and 4402: exemplary optimal design region 2, described as L+0.4 mm≤s≤L+1.5 mm, 1 mm≤L≤4 mm.

Figures 45A, 45B, 45C, 45D:
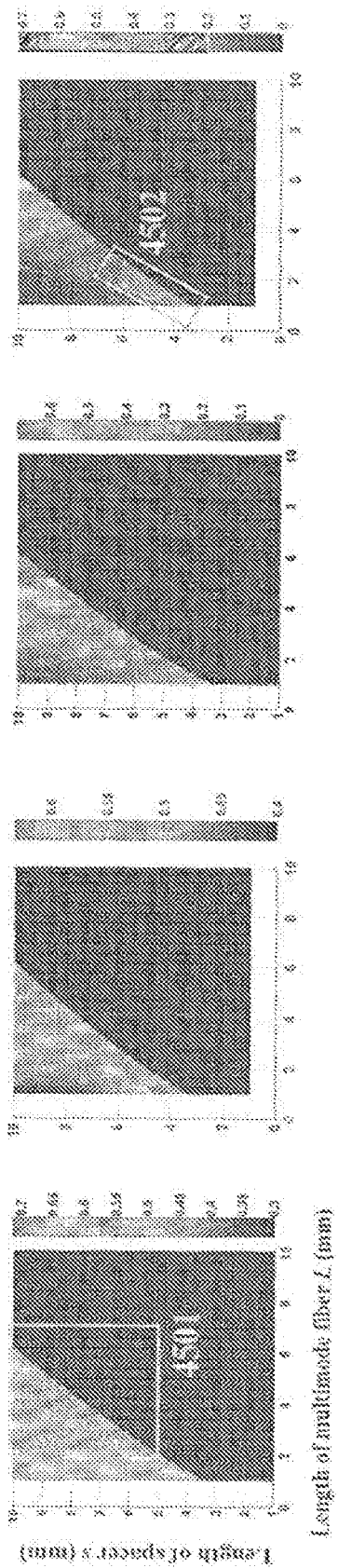
FIGS. 45(a)-45(g) are illustrations of the exemplary optimal design parameter ranges for the exemplary capsule probes with imaging range 4.5-7 mm, rigid length less than 20 mm and aperture diameter less than 3 mm operated at wavelength 800 nm, according to another exemplary embodiment of the present disclosure which can be implemented with any one of the exemplary embodiments of the present disclosure described herein.
Figures 45E, 45F, 45G:
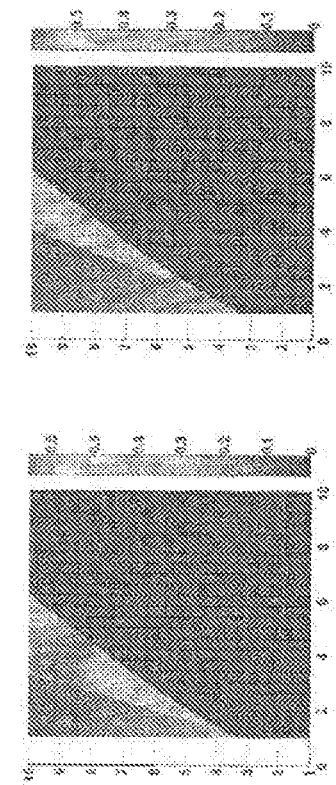
Figures 48A, 48B, 48C, 48D, 48E, 48F, 48G:
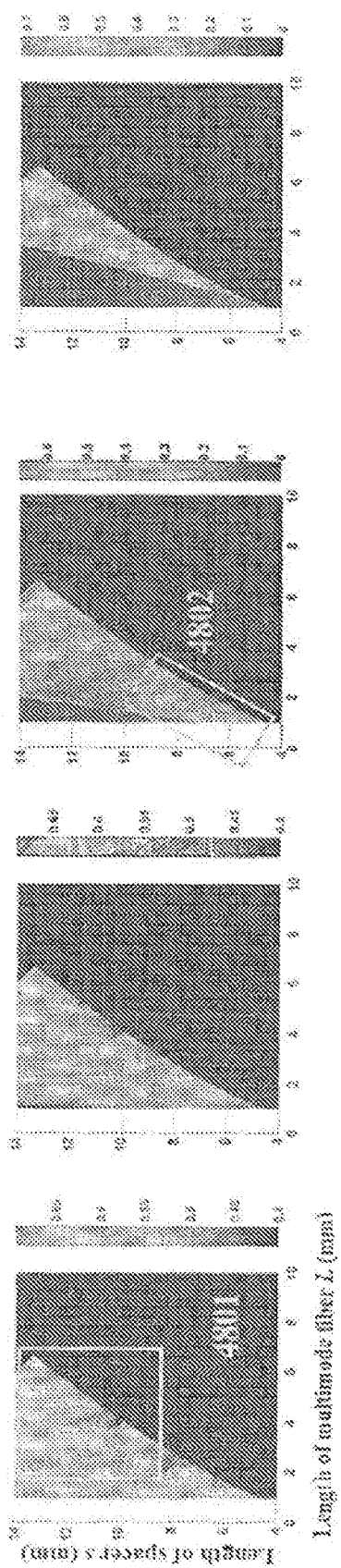
FIGS. 48(a)-48(g) are illustrations of the exemplary optimal design parameter ranges for balloon probes with imaging range 9-12 mm, rigid length less than 20 mm and aperture diameter less than 3 mm operated at wavelength 1300 nm, according to another exemplary embodiment of the present disclosure which can be implemented with any one of the exemplary embodiments of the present disclosure described herein.

FIGS. 45(*a*)-45(*g*) show illustrations of the exemplary design parameter ranges for capsule probes with imaging range 4.5-7 mm, rigid length less than 20 mm and aperture diameter less than 3 mm operated at wavelength 800 nm, according to an exemplary embodiment of the present disclosure. Optimization color maps for designs operated at 800 nm wavelength using multimode fiber with diameters of (a) 50 μm, (b) 100 μm, (c) 500 μm, (d) 1000 μm, (e) 1500 μm, (f) 2000 μm and (g) 2500 μm are presented—4501: exemplary optimal design region 1, described as L 2 mm≤L≤7 mm, 5 mm≤s≤10 mm; and 4502: exemplary optimal design region 2, described as L+2 mm≤s≤2L+2 mm, 1 mm≤L≤3 mm.

FIGS. 46(a)-46(g) show illustrations of the exemplary design parameter ranges for capsule probes with imaging range 4.5-7 mm, rigid length less than 20 mm and aperture diameter less than 3 mm operated at wavelength 1300 nm, according to an exemplary embodiment of the present disclosure. Optimization color maps for designs operated at 1300 nm wavelength using multimode fiber with diameters of (a) 50 µm, (b) 100 µm, (c) 500 µm, (d) 1000 µm, (e) 1500 µm, (f) 2000 µm and (g) 2500 µm are presented—4601: exemplary optimal design region 1, described as 1.5 mm≤L≤6.5 mm, 5.5 mm≤s≤10 mm; and 4602: exemplary optimal design region 2, described as L+2 mm≤s≤2L+2 mm, 1 mm≤L≤3.5 mm.

FIGS. 47(a)-47(g) show illustrations of the exemplary design parameter ranges for balloon probes with imaging range 9-12 mm, rigid length less than 20 mm and aperture diameter less than 3 mm operated at wavelength 800 nm, according to an exemplary embodiment of the present disclosure. Optimization color maps for designs operated at 800 nm wavelength using multimode fiber with diameters of (a) 50 µm, (b) 100 µm, (c) 500 µm, (d) 1000 µm, (e) 1500 µm, (f) 2000 µm and (g) 2500 µm are presented—4701: exemplary optimal design region 1, described as 0.8 mm≤L≤7 mm, 8 mm≤s≤14 mm; and 4702: exemplary optimal design region 2, described as 1.5L+3 mm≤s≤2L+5 mm, 1 mm≤L≤3 mm.

FIGS. 48(a)-48(g) show illustrations of the exemplary design parameter ranges for balloon probes with imaging range 9-12 mm, rigid length less than 20 mm and aperture diameter less than 3 mm operated at wavelength 1300 nm, according to an exemplary embodiment of the present disclosure. Optimization color maps for designs operated at 1300 nm wavelength using multimode fiber with diameters of (a) 50 µm, (b) 100 µm, (c) 500 µm, (d) 1000 µm, (e) 1500 µm, (f) 2000 µm and (g) 2500 µm are presented—4801: exemplary optimal design region 1, described as 1.8 mm≤L≤7 mm, 8 mm≤s≤14 mm; and 4802: exemplary optimal design region 2, described as 1.5L+3 mm≤s≤2L+5 mm, 1 mm≤L≤4 mm.

The foregoing merely illustrates the principles of the present disclosure. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system, SECM system, OBM system or other imaging systems capable of imaging in vivo or fresh tissues, and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, U.S. Patent Publication No. 2002/0122246, published on May 9, 2002, U.S. Patent Application 61/649,546, U.S. patent application Ser. 11/625,135, and U.S. Patent Application 61/589,083, the disclosures of which are incorporated by reference herein in their entireties. It will thus be appreciated that those skilled in the art will be able to devise numerous systems, arrangements and methods which, although not explicitly shown or described herein, embody the principles of the present disclosure and are thus within the spirit and scope of the present disclosure. Further, various exemplary embodiments described herein can be interchangeably used with all other exemplary described embodiments, as should be understood by those having ordinary skill in the art. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus for illuminating a sample in an optical coherence tomography (OCT) system, comprising:
    a first optical waveguide which emits light at a distal end thereof;
    a second optical waveguide which receives the light from the distal end of the first optical waveguide and emits the light toward a lens,
        the emitted light comprising a first beam and at least a second beam,
            the first beam being transmitted toward the lens without being internally reflected within the second optical waveguide, and
            the second beam being internally reflected within the second optical waveguide before being transmitted toward the lens; and
    the lens being configured to direct the first beam and the second beam toward the sample,
        the first beam forming a first beam waist at a first distance from the lens, and
        the second beam forming a second beam waist at a second distance from the lens different from the first distance.

2. The apparatus of claim 1, wherein the first distance of the first beam waist from the lens substantially coincides with a focal plane of the lens.

3. The apparatus of claim 1, wherein the second optical waveguide converts the light into a plurality of propagation modes,
    wherein the first beam corresponds to a $0^{th}$ order propagation mode, and
    wherein the second beam corresponds to a $1^{st}$ order propagation mode.

4. The apparatus of claim 3, wherein the number of propagation modes is based on a length of the second optical waveguide.

5. The apparatus of claim 1, further comprising a spacer between the second optical waveguide and the lens.

6. The apparatus of claim 1, wherein the lens comprises an optical axis, and
    wherein the first beam is emitted through a surface of the lens at a first area and forms the first beam waist along the optical axis.

7. The apparatus of claim 6, wherein the second beam is emitted through the surface of the lens at a second annular area including an outer radius that is greater than a radius of the first area, and
    wherein the second beam forms the second beam waist along the optical axis.

8. The apparatus of claim 1, wherein the second optical waveguide comprises a mirror tunnel.

9. The apparatus of claim 1, wherein the lens is disposed in a catheter.

10. The apparatus of claim 1, wherein the lens is disposed in a swallowable capsule.

11. The apparatus of claim 1, wherein the first optical waveguide is a single mode optical fiber, and wherein the second optical waveguide is a multimode optical fiber.

12. The apparatus of claim 1, further comprising:
a light source optically coupled to a proximal end of the first optical waveguide; and
an image sensor optically coupled to the proximal end of the first optical waveguide.

13. A method for illuminating a sample in an optical coherence tomography (OCT) system, comprising:
emitting light from a distal end of a first optical waveguide;
emitting, from a second optical waveguide, the light received from the distal end of the first optical waveguide toward a lens,
the emitted light comprising a first beam and at least a second beam,
the first beam being transmitted toward the lens without being internally reflected within the second optical waveguide, and
the second beam being internally reflected within the second optical waveguide before being transmitted toward the lens;
directing, by the lens, the first beam and the second beam toward the sample;
focusing, by the lens, the first beam into a first beam waist at a first distance from the lens; and
focusing, by the lens, the second beam into a second beam waist at a second distance from the lens different from the first distance.

14. The method of claim 13, wherein the first distance of the first beam waist from the lens substantially coincides with a focal plane of the lens.

15. The method of claim 13, wherein the second optical waveguide, when emitting the light received from the distal end of the first optical waveguide toward a lens, converts the light into a plurality of propagation modes,
wherein the first beam corresponds to a $0^{th}$ order propagation mode, and
wherein the second beam corresponds to a $1^{st}$ order propagation mode.

16. The method of claim 15, wherein the number of propagation modes is based on a length of the second optical waveguide.

17. The method of claim 13, wherein the second optical waveguide, when emitting the light received from the distal end of the first optical waveguide toward the lens, emits the light received from the distal end of the first optical waveguide toward the lens through a spacer disposed between the second optical waveguide and the lens.

18. The method of claim 13, wherein the lens comprises an optical axis, and
wherein the lens, when directing the first beam and the second beam toward the sample, emits the first beam through a surface of the lens at a first area and form the first beam waist along the optical axis.

19. The method of claim 18, wherein the lens, when directing the first beam and the second beam toward the sample, emits the second beam through the surface of the lens at a second annular area having an outer radius that is greater than a radius of the first area,
wherein the second beam forms the second beam waist along the optical axis.

20. The method of claim 13, wherein the second optical waveguide comprises a mirror tunnel.

21. The method of claim 13, wherein the lens is disposed in a catheter.

22. The method of claim 13, wherein the lens is disposed in a swallowable capsule.

23. The method of claim 13, wherein the first optical waveguide is a single mode optical fiber, and wherein the second optical waveguide is a multimode optical fiber.

24. The method of claim 13, further comprising:
optically coupling a light source to a proximal end of the first optical waveguide; and
optically coupling an image sensor to the proximal end of the first optical waveguide.

* * * * *

UNITED STATES PATENT AND TRADEMARK OFFICE
CERTIFICATE OF CORRECTION

PATENT NO. : 11,112,232 B2
APPLICATION NO. : 16/796103
DATED : September 7, 2021
INVENTOR(S) : Guillermo J. Tearney et al.

It is certified that error appears in the above-identified patent and that said Letters Patent is hereby corrected as shown below:

In the Specification

Please insert the following after the first paragraph in Column 1, Line 6:
--STATEMENT REGARDING FEDERALLY SPONSORED RESEARCH
This invention was made with government support under HL076398 awarded by the National Institutes of Health. The government has certain rights in the invention.--.

Signed and Sealed this
Ninth Day of May, 2023

Katherine Kelly Vidal
*Director of the United States Patent and Trademark Office*